United States Patent [19]
Mistretta et al.

[11] 3,974,386
[45] Aug. 10, 1976

[54] DIFFERENTIAL X-RAY METHOD AND APPARATUS

[75] Inventors: Charles A. Mistretta; Frederick Kelcz, both of Madison, Wis.

[73] Assignee: Wisconsin Alumni Research Foundation, Madison, Wis.

[22] Filed: Mar. 27, 1975

[21] Appl. No.: 562,668

Related U.S. Application Data

[63] Continuation-in-part of Ser. No. 488,250, July 12, 1974, abandoned.

[52] U.S. Cl............................. 250/402; 178/DIG. 5; 250/510
[51] Int. Cl.² ........................................ G03B 41/16
[58] Field of Search .......... 250/505, 510, 401, 402, 250/416, 327, 320, 321, 322, 323; 178/DIG. 5

[56] References Cited
UNITED STATES PATENTS

| | | | |
|---|---|---|---|
| 3,588,502 | 6/1971 | Greenfield...................... | 250/510 X |
| 3,854,049 | 12/1974 | Mistretta et al. .................... | 250/402 |

*Primary Examiner*—Alfred E. Smith
*Assistant Examiner*—T. N. Grigsby
*Attorney, Agent, or Firm*—Burmeister, York, Palmatier, Hamby & Jones

[57] ABSTRACT

Differential X-ray images are produced in order to improve the visibility of a contrast medium, such as iodine or xenon, having a K absorption edge at a predetermined X-ray energy. Such differential images are produced by combining first, second and third X-ray images which are individually produced by using first, second and third X-ray spectra at first, second and third X-ray energy levels. The first energy level is below the K edge energy, while the second energy level is above the K edge energy. The third energy level is above the second energy level. The second X-ray image is combined subtractively with the average of the first and third X-ray images to produce a differential X-ray image in which any image elements due to soft tissue and bone are largely cancelled out, while image elements due to the contrast medium are enhanced. In one preferred method, two versions of the second image are combined additively, and the first and third images are combined subtractively therewith. The first, second and third X-ray spectra may be produced by using a single X-ray source with first, second and third X-ray filters. When the contrast medium is iodine, such filters may contain iodine, cerium and lead, respectively. The X-ray source is preferably operated with first, second and third anode voltages when the first, second and third filters are used. The intensity level of the X-ray source may also be changed to provide three different intensity levels for the three different filters. The three X-ray images are preferably converted into television images which are combined electronically to produce the differential X-ray images. Three different gain levels may be employed in the television system for the three filters. The television system may include first and second image storage tubes to provide two stages of image subtraction. The first storage tube may be arranged to produce the differences between successive images in a four image system, in which two versions of the second X-ray image are used alternately with the first and third images. The difference signals produced by the first tube are then selectively written positively or negatively on the second tube in such a manner as to enhance and integrate the image elements due to the contrast medium, while largely cancelling out the image elements due to the soft tissue and bone.

In the television system, it is highly advantageous to provide logarithmic video amplification, so that except for constant terms the video images will be proportional to the absorption coefficients. With such logarithmic amplification, the greatest degree of cancellation of the image elements due to bone and soft tissue is achieved.

49 Claims, 27 Drawing Figures

FILTER WHEEL PHOTOTRANSISTOR PULSES

VIDEO SIGNAL AFTER LOGARITHMIC AMPLIFICATION

DEVIATION FROM TRUE LOG OUTPUT VS. TISSUE THICKNESS
⊙ OUTPUT W/ IODINE FILTER
□ OUTPUT W/ LEAD FILTER

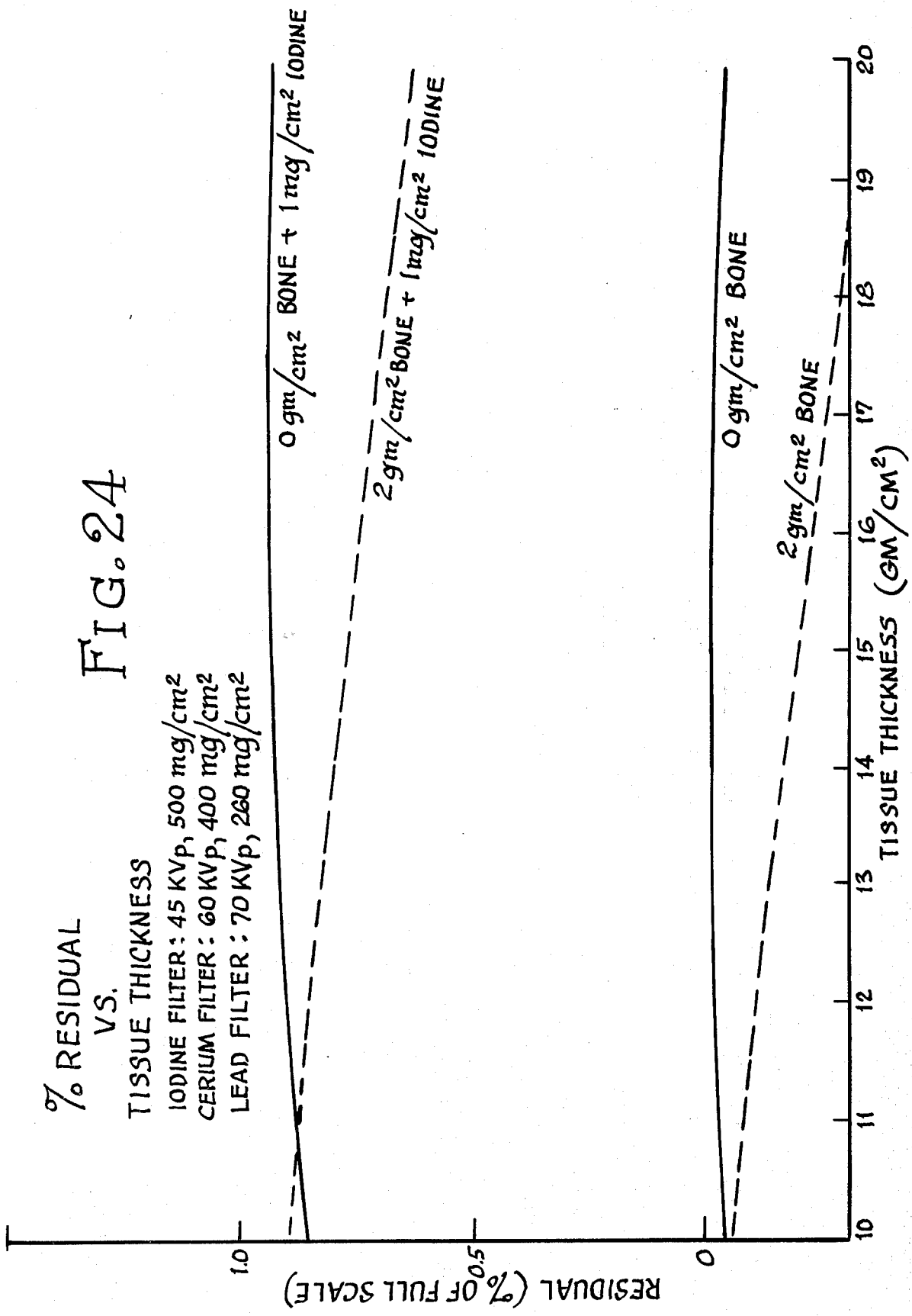

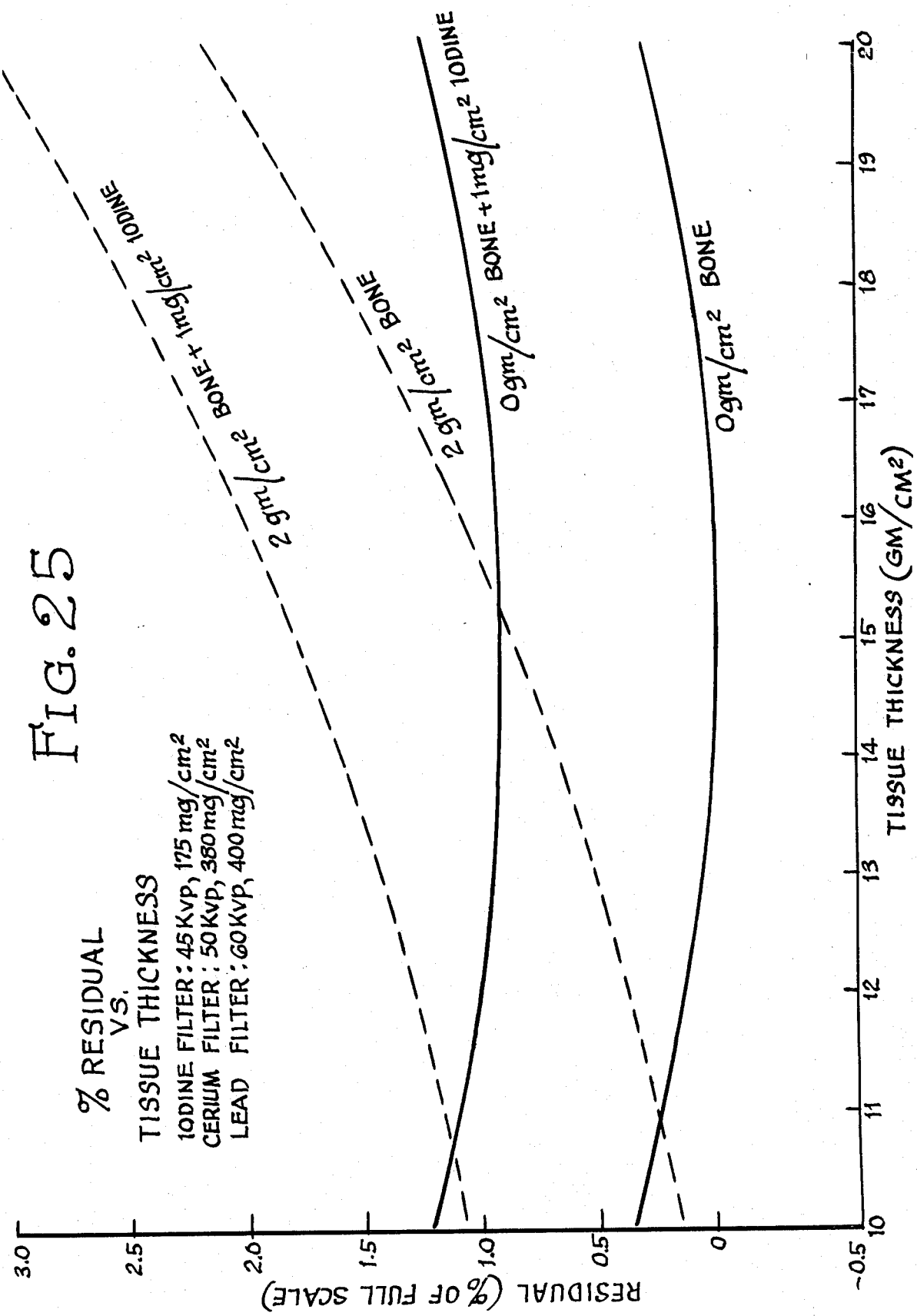

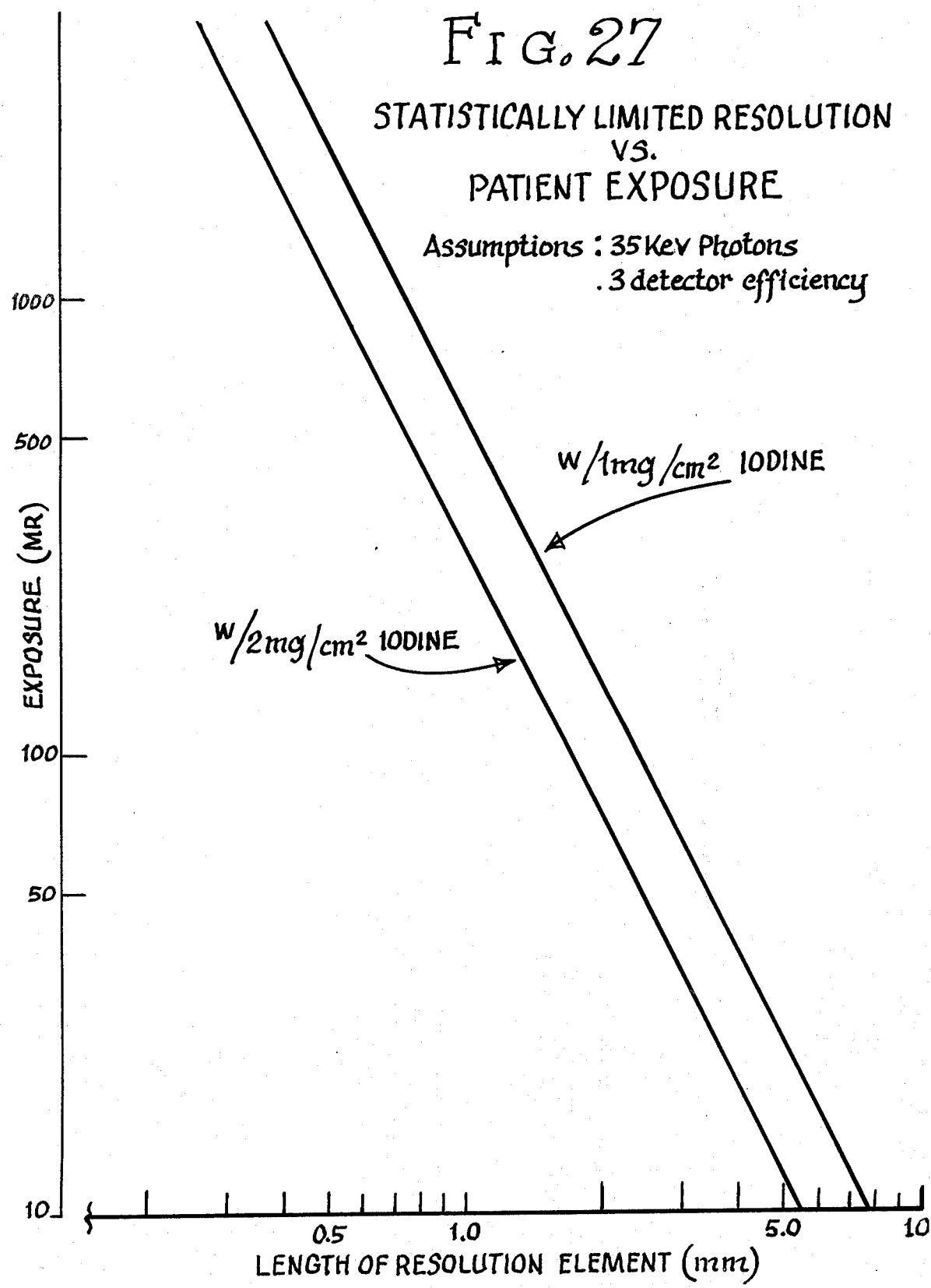

DIFFERENTIAL X-RAY METHOD AND APPARATUS

The invention described herein was made in the course of work under a grant or award from the Department of Health, Education, and Welfare.

This application is a continuation-in-part of our co-pending application, Ser. No. 488,250, filed July 12, 1974, and now abandoned.

This invention relates to a method and apparatus for producing differential X-ray images, so as to improve the visibility of a contrast medium, such as iodine, xenon or barium, for example.

Iodine is present naturally in the human body, particularly in the thyroid gland. Moreover, iodine containing solutions can be injected as a contrast medium into the blood stream. Xenon gas can be inhaled to provide a contrast medium in the lungs. Barium is commonly used as a contrast medium in the digestive track.

One object of the present invention is to enhance the visibility of a contrast medium which is present in the human body in very small concentrations. The use of small concentrations avoids the toxic effects of such contrast media.

In the method of the present invention, a contrast medium is used having a K absorption edge at a predetermined energy. At the K edge, the X-ray absorption coefficient of the contrast medium increases abruptly.

In accordance with the present invention, first, second and third X-ray images are produced, using first, second and third X-ray spectra at first, second and third energy levels. The first energy level is below the K edge energy, while the second energy level is above the K edge energy. The third energy level is above the second level. The three X-ray images are combined substractively in such a way as to produce a differential X-ray image in which the image elements due to the contrast medium are enhanced, while the image elements due to soft tissue and bone are largely cancelled out. The second X-ray image may be combined subtractively with the average of the first and third X-ray images. The subtraction of the average tends to cancel out the background image elements due to soft tissue and bone, while retaining and enhancing the image elements due to the contrast medium.

The combination of the three X-ray images may be brought about by doubling the second X-ray image, and subtracting the first and third images therefrom. This may be done by producing four X-ray images, including two versions of the second X-ray image, produced alternately with the first and third X-ray images. The differential X-ray images may be produced by additively combining the two versions of the second X-ray image and subtractively combining the first and third X-ray images therewith.

The three X-ray spectra may be produced by using first, second and third X-ray filters with a single X-ray source. When the contrast medium is iodine, the three filters may contain iodine, cerium and lead, respectively. To assist in achieving the most advantageous balance between the three spectra, it is preferred to use three different anode voltages in the X-ray source, for the three filters. Three different X-ray tube currents may also be employed to produce three different intensity levels for the three filters.

The method of the present invention may be advantageously implemented by providing a television system in which X-ray images are converted into television images, which are then combined electronically to produce the differential X-ray images.

It is advantageous to produce a series of four X-ray images by using a series of four filters, including two identical versions of the second filter, alternating with the first and third filters.

The electronic system for combining the four television images may utilize two stages of video subtraction. The first stage may include a video difference detector tube which is arranged to store each image and to produce video output signals corresponding to the difference between the successive images. The second stage of video subtraction may include a silicon storage tube capable of writing video images both positively and negatively. By alternating between positive and negative writing modes, according to which filter is being used, the silicon storage tube additively combines and integrates the image elements due to the contrast medium, while subtractively combining and thereby largely cancelling out the image elements due to soft tissue and bone. The final result is a differential video image in which the contrast medium is greatly enhanced, while the residual elements due to soft tissue and bone are minimized. This differential image can be displayed on a television monitor. Permanent photographs of the image can be made, if desired.

The method and apparatus of the present invention make it possible to visualize minute quantities of iodine in the human body, particularly in the thyroid gland and the circulatory system. Minute quantities of other contrast media can also be visualized with great clarity. Thus, xenon gas in the lungs can be rendered clearly visible. A minute quantity of a contrast medium that would initially produce an X-ray image contrast of less than 1% can be rendered clearly visible with full contrast.

Only a short X-ray exposure is sufficient to produce such enhancement of a contrast medium. Typically, the X-ray exposure will amount to only a few seconds.

Further objects, advantages and features of the present invention will appear from the following description taken with the accompanying drawings, in which.

Figure 22:
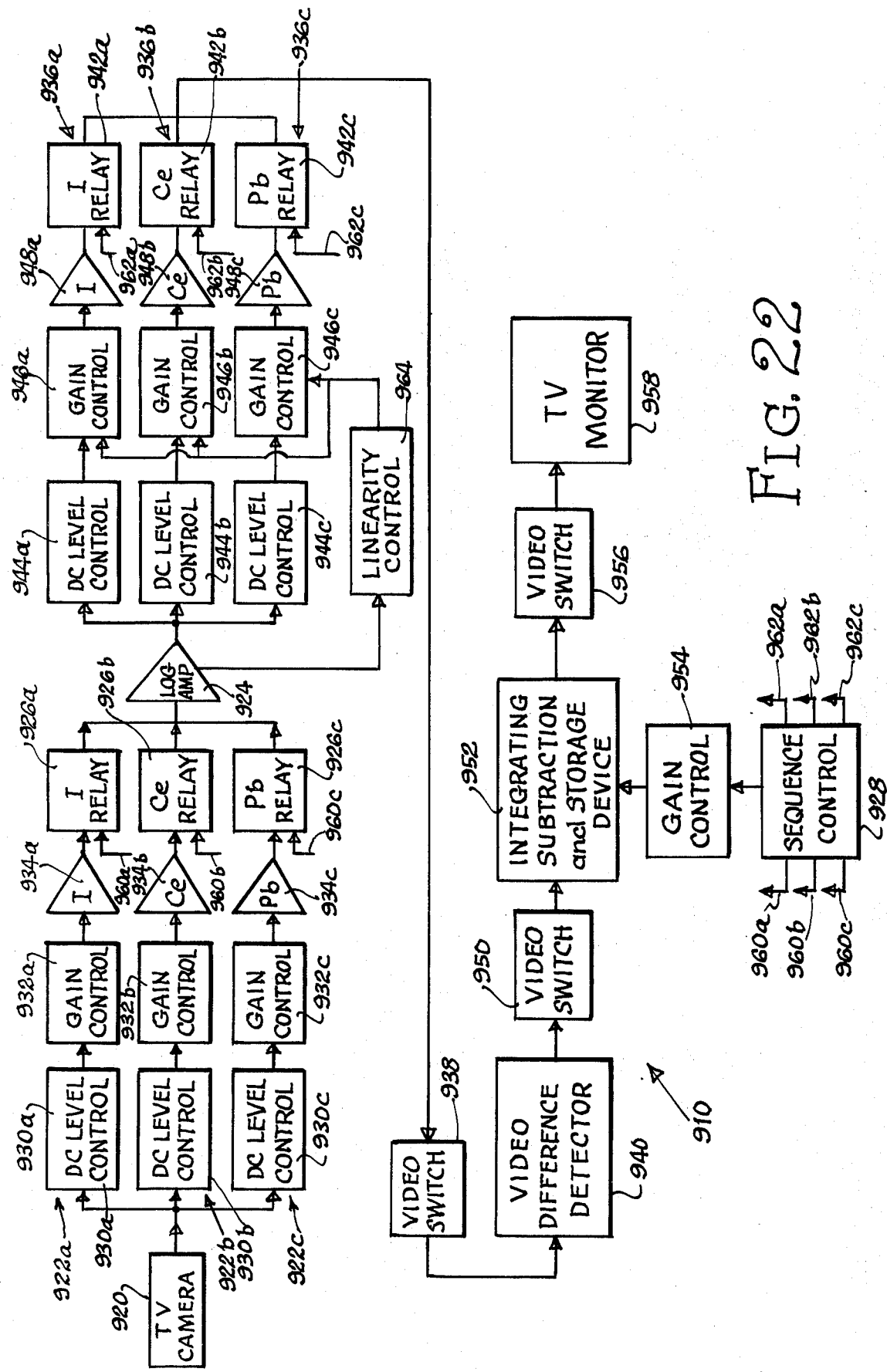
FIG. 22 is a schematic diagram of a modified differential X-ray system constituting another embodiment of the method and apparatus of the present invention.
Figure 23:
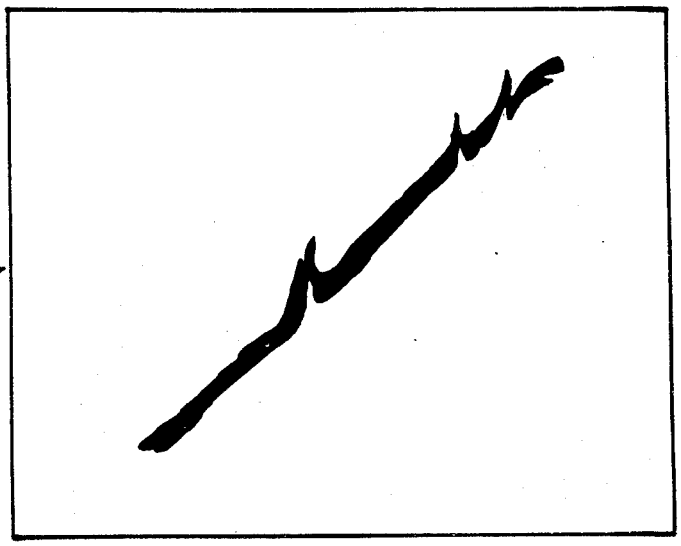

FIG. 23 is a reproduction of an oscilloscope trace representing one frame of the video signal as it appears after logarithmic amplification in the system of FIG. 22, using one of the X-ray filters with a phantom comprising a lucite wedge with a 10 cm thickness variation. The black level is at the top of this trace. The upward bumps on the trace are produced by lead (Pb) markers for 4, 9 and 14 cm of patient thickness.

FIG. 24 is a graph, produced with the system of FIG. 22, representing the residual signal, as a percentage of full scale, plotted against tissue thickness, for the following conditions of filtration:
  Iodine filter: 45KVp, 500 mg/cm$^2$;
  Cerium filter: 60KVp, 400 mg/cm$^2$;
  Lead filter: 70KVp, 260 mg/cm$^2$.

FIG. 25 is a graph similar to FIG. 24 but for the following different conditions of filtration:
  Iodine filter: 45KVp, 175 mg/cm$^2$;
  Cerium filter: 50KVp, 380 mg/cm$^2$;
  Lead filter: 60KVp, 400 mg/cm$^2$.

Figure 26:
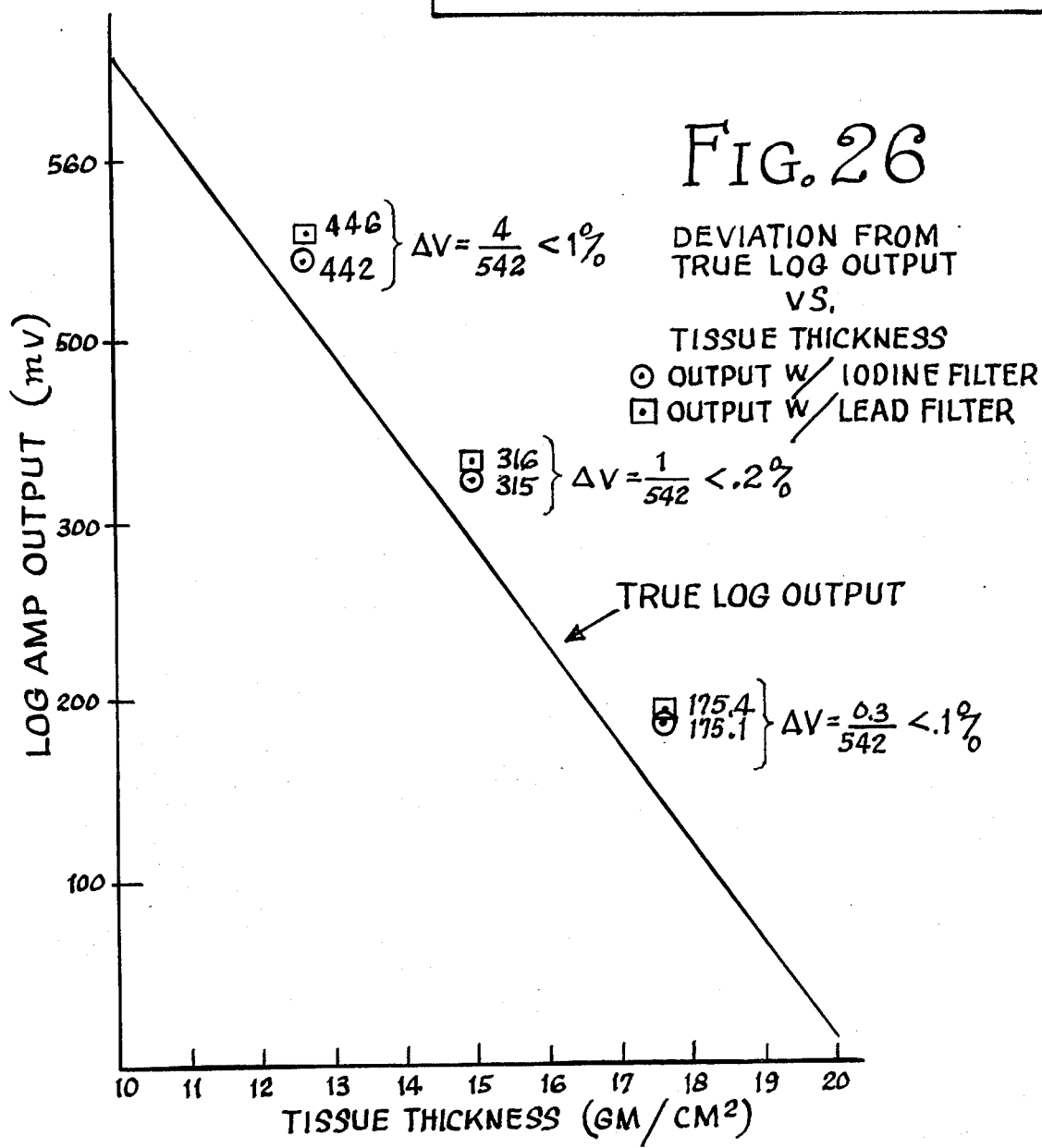

FIG. 26 is a graph illustrating the expected deviation from true logarithmic behavior, in the system of FIG. 22, due to log amplifier nonuniformity and sinusoidal areal nonuniformity in the system.

FIG. 27 is a graph showing the statistically limited resolution of the system shown in FIG. 22, plotted against patient exposure assuming the use of 35 KeV photons with 0.3 detector efficiency.

Figure 1:
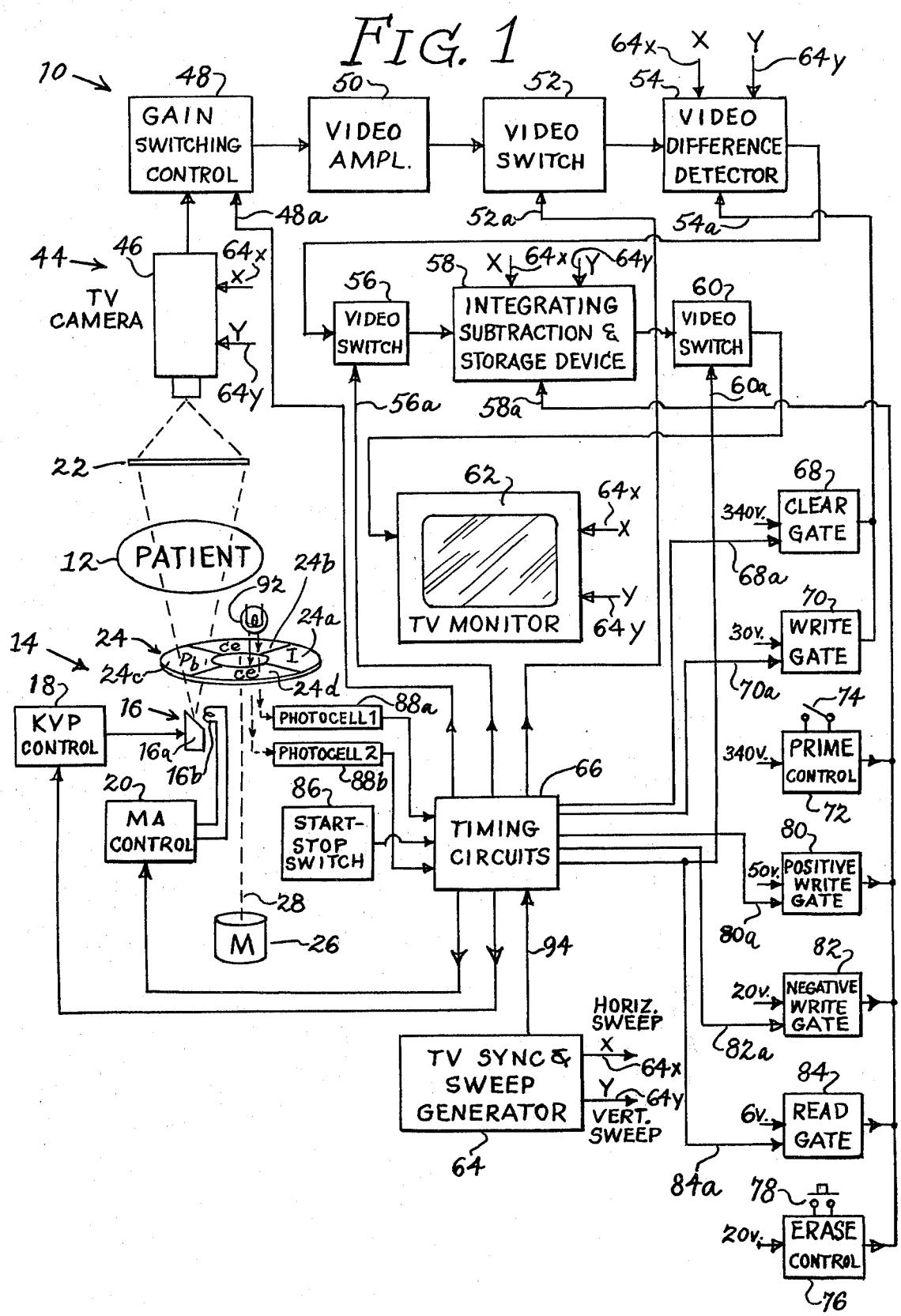
FIG. 1 is a block diagram showing an X-ray system which embodies the method and apparatus of the present invention.

It will be understood that the present invention is not limited to any particular apparatus, and that the method of the present invention can be practiced with various X-ray systems. Thus, it is merely by way of example that FIG. 1 illustrates an advantageous X-ray system or apparatus 10, to be described as an illustrative embodiment of the present invention. The system 10 is adapted to produce differential X-ray images of a patient or subject 12. In such images, the image components due to soft tissue and bone are largely cancelled out, while the image elements due to a contrast medium are enhanced and integrated. Thus, the system 10 affords automatic and effective compensation for variations in the thickness of the patient, both as to soft tissue thickness and bone thickness. Due to the cancellation of the image elements produced by ordinary soft tissue and bone, the X-ray system is largely insensitive to variations in the thickness of soft tissue and bone in the patient. This feature is highly advantageous, because the thickness of the portion of the patient to be X-rayed is subject to variation in a more or less irregular manner over the field of view. While the cross-sectional shape of the patient 12 is shown as a simple oval, it will be understood that the actual shape is more or less irregular.

The X-ray system 10 comprises an X-ray source assembly 14 for producing a plurality of different X-ray spectra, which may be either monoenergetic or quasi-monoenergetic. In this case, the source assembly 14 is adapted to produce a series of quasi-monoenergetic X-ray spectra. It is advantageous to utilize a single X-ray source which may take the form of an ordinary X-ray tube 16 having an anode 16a and a filament or cathode 16b.

In the system of FIG. 1, the anode voltage for the X-ray tube 16 is supplied by a high voltage power supply 18, which is labeled KVP CONTROL, because it is constructed to afford electronic control over the kilovolts peak (KVP), applied between the anode 16a and the cathode 16b. The time intervals during which the anode voltage is applied are also subject to electronic control.

The electron current between the cathode 16b and the anode 16a is also preferably subject to electronic control, by varying the filament current. Thus, the filament 16b is connected to a power supply 20 which is labeled MA CONTROL, because it is constructed to afford electronic control over the electron current in milliamperes (MA).

The X-ray tube 16 produces a continuous X-ray spectrum over a fairly wide band of energies. The maximum energy of the band of X-rays is determined by the maximum voltage or KVP applied to the anode 16a of the X-ray tube 16.

The X-ray beam from the X-ray source 16 is directed through the patient 12 to an image detector which may take the form of an intensification screen 22, adapted to convert the invisible X-ray image into a visible image, composed of visible light. For convenience, such visible images, corresponding to invisible X-ray images, will be referred to at times as visible X-ray images.

To produce a series of quasi-monoenergetic X-ray spectra, it is preferred to provide a plurality of selectively movable or usable X-ray filters, adapted to be moved individually into the X-ray beam, so that the X-ray beam must pass through the individual filter, as well as the patient 12.

At least three such X-ray filters are preferably employed and are mounted on a rotatable filter wheel 24. The filters produce three different X-ray spectra at different energy levels. In this case, the filter wheel 24 carries four X-ray filters 24a, 24b, 24c and 24d. The first three filters, 24a, b and c are different, but the fourth filter 24d preferably is a second version or duplicate of the second filter 24b.

It will be understood that a wide variety of X-ray filtering materials may be employed in the X-ray filters, 24a–d, depending upon various factors such as the nature of the contrast medium which is to be visualized in the differential X-ray images. When it is desired to use iodine as the contrast medium, the three filters 24a, b and c may contain iodine (I), cerium (Ce) and lead (Pb). The fourth filter 24d may also be a cerium filter, duplicating the second filter 24b.

A motor 26 is preferably provided to rotate the filter wheel 24, so that each filter in turn will be moved into the X-ray beam. The motor 26 may be connected to the filter wheel 24 by a drive shaft 28, or some other drive. The rotary speed of the filter wheel 24 may be varied widely, but, for example, may be on the order of one revolution per second.

The filters 24a–d may be in the form of hollow cells which hold solutions containing the X-ray filtering materials. Thus, the iodine filter 24a may contain a solution of iodine or an iodine compound. Similarly, the cerium filters 24b and d may contain solutions of a cerium compound while the lead filter 24c may contain a solution of a lead compound. The use of chemical solutions in the X-ray filters makes it easy to change the effective density of each filter, simply by changing the concentration of the filtering material in the solution for that particular filter.

Figure 7:
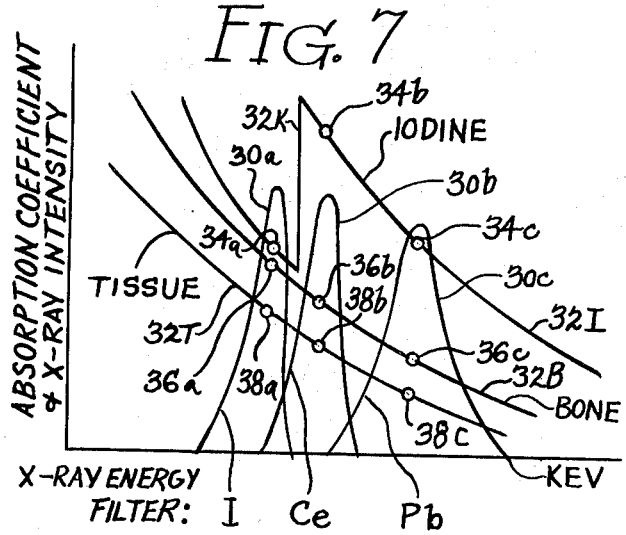
FIG. 7 is a graph illustrating the X-ray spectra produced by the X-ray filters, and also the relationship between such spectra and the absorption coefficients for soft tissue, bone and iodine, used as a contrast medium in this case.
Figure 8:
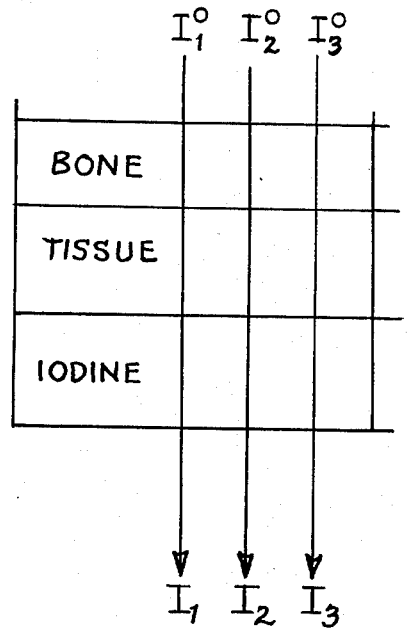
FIG. 8 is a diagram illustrating the penetration of the bone, soft tissue, and iodine by the three X-ray spectra.

FIG. 7 includes graphical representations 30a, b and c of the three quasi-monoenergetic spectra produced by the iodine, cerium and lead filters. These graphs are plots of relative X-ray intensities against X-ray energies in KEV (killo-electron volts).

FIG. 7 also includes graphs 32I, 32B and 32T, representing the absorption coefficients of iodine, bone, and soft tissue, plotted as a function of X-ray energy in KEV. It will be noted that the graph 32I for iodine includes an abrupt discontinuity or edge 32K, commonly known as the K edge for iodine. At the K edge 32K, the absorption coefficient for iodine increases abruptly. A number of materials have such K edges, at various X-ray energies. Generally, the K edge energy is different for each material. Xenon and barium, in addition to iodine, have K edges. Such materials with K edges are especially advantageous as X-ray contrast media.

In accordance with the method of the present invention, the three X-ray spectra 30a, b and c are at three different energy levels which are related to the K edge energy of the material to be employed as the contrast medium. Thus, as shown in FIG. 7, the first spectrum 30a is centered at an energy level which is below the K edge energy. The second spectrum 30b is perferably centered at an energy level which is above the K edge energy. The third spectrum 30c is centered at an energy level which is above the energy level of the second spectrum 30b. The fourth spectrum is preferably a second version or duplicate of the second spectrum 30b.

Because of the abrupt rise of the X-ray absorption coefficient for iodine at the K edge 32K, the absorption coefficient is much greater for the second spectrum 30b than for the first spectrum 30a. Moreover, the absorption coefficient for iodine is much greater for the second spectrum 30b than for the third spectrum 30c.

On the other hand, the X-ray absorption coefficients for bone and soft tissue decrease gradually with increasing X-ray energy. Thus, the absorption coefficient for bone is less for the second spectrum 30b than for the first spectrum 30a, and is still less for the third spectrum 30c. Similarly, the absorption coefficient for soft tissue is less for the second spectrum 30b than for the first spectrum 30a, and is still less for the third spectrum 30c.

The three spectra 30a, b and c are chosen and adjusted so that the absorption coefficient as to bone for the second spectrum 30b is approximately equal to the average absorption coefficient as to bone for the first and third spectra 30a and c. Similarly, the absorption coefficient as to tissue for the second spectrum 30b is approximately equal to the average absorption coefficient as to tissue for the first and third spectra 30a and c. When this relationship exists, the X-ray image components due to bone and soft tissue can be largely cancelled out by subtracting the average of the X-ray images produced by the first and third spectra from the X-ray image produced by the second spectrum. On the other hand, the X-ray image elements due to iodine are not cancelled out by this subtractive combination, thus, there is a very great relative enhancement of the image elements due to the iodine or other contrast medium.

In FIG. 7, the absorption coefficients as to iodine for the three spectra 30a, b and c are indicated by points 34a, b and c. The absorption coefficients as to bone for the three spectra 30a, b and c are indicated by the points 36a, b and c. As to soft tissue, the absorption coefficients for the three spectra 30a, b and c are indicated by points 38a, b and c.

Figure 11:
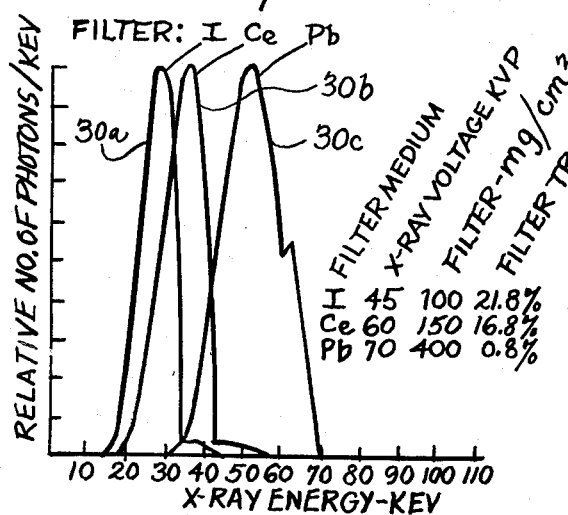
FIG. 11 is a set of graphs illustrating the X-ray spectra produced with the three different filters.
Figure 12:
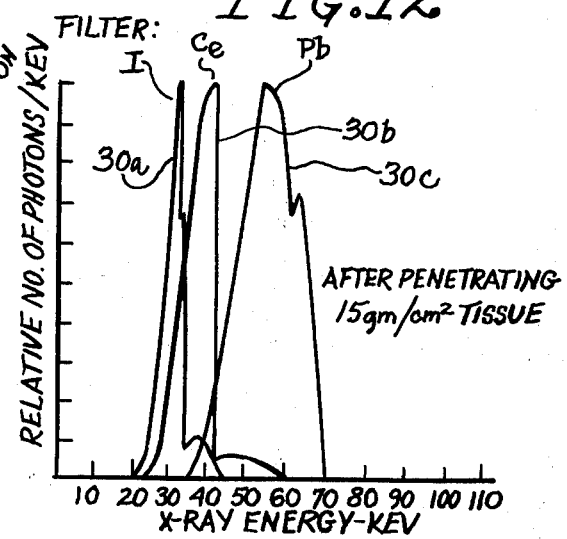
FIG. 12 is a set of graphs similar to FIG. 11 showing the modifications in the spectra after penetrating soft tissue.
Figure 13:
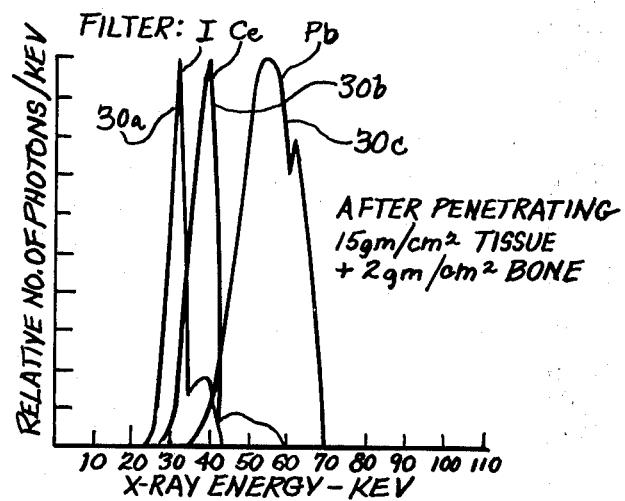
FIG. 13 is a set of graphs similar to FIG. 11, showing the modifications in the spectra after penetrating bone.

FIGS. 11, 12 and 13 show the graphical representations of the three X-ray spectra 30a, b and c in greater detail, for the specific system 10 of FIG. 1, using filters containing iodine, cerium and lead, to enhance the X-ray visibility of iodine in the patient. FIG. 11 shows the three spectra 30a, b and c after being produced by the X-ray tube 16 and passing through the iodine, cerium and lead filters 24a, b and c. Preferably, the X-ray voltage is different for each spectrum. Moreover, the concentration of the filtering medium in each filter may be different. FIG. 11 includes a table giving one set of values which have been employed successfully. The voltages used with the iodine, cerium and lead filters were 45, 60 and 70 KVP. The concentrations of the three filter media, given in milligrams per square centimeter were 100 as to iodine, 150 as to cerium, and 400 as to lead. The resulting filter transmissions were 21.8% as to iodine, 16.8% as to cerium, and 0.8% as to lead. It will be understood that these values are examples only, and are subject to wide variations.

FIG. 12 shows the three X-ray spectra 30a, b and c, produced with the use of the iodine, cerium and lead filters, after the spectra have passed through soft tissue amounting to 15 grams per square centimeter. It will be noted that all three spectra are shifted to slightly higher energy levels, and that the peaks of the spectra are sharpened. However, the relationship between the three spectra remains substantially the same as before.

FIG. 13 illustrates the three spectra 30a, b and c after the X-rays have passed through 15 grams per square centimeter of soft tissue and 2 grams per square centimeter of bone. It will be seen that the X-ray spectra 30a, b and c are shifted to still higher energy levels, and that the peaks of the spectra are sharpened. However, the relationship between the three spectra remains substantially the same as before. Thus, FIGS. 11, 12 and 13 illustrate the fact that the use of the three spectra provides effective and automatic compensation for variations in patient thickness, both as to soft tissue in the patient and as to bone. The image components as to soft tissue and bone can be largely cancelled out by subtracting the average of the images due to the first and third spectra from the image due to the second spectrum.

Figure 14:
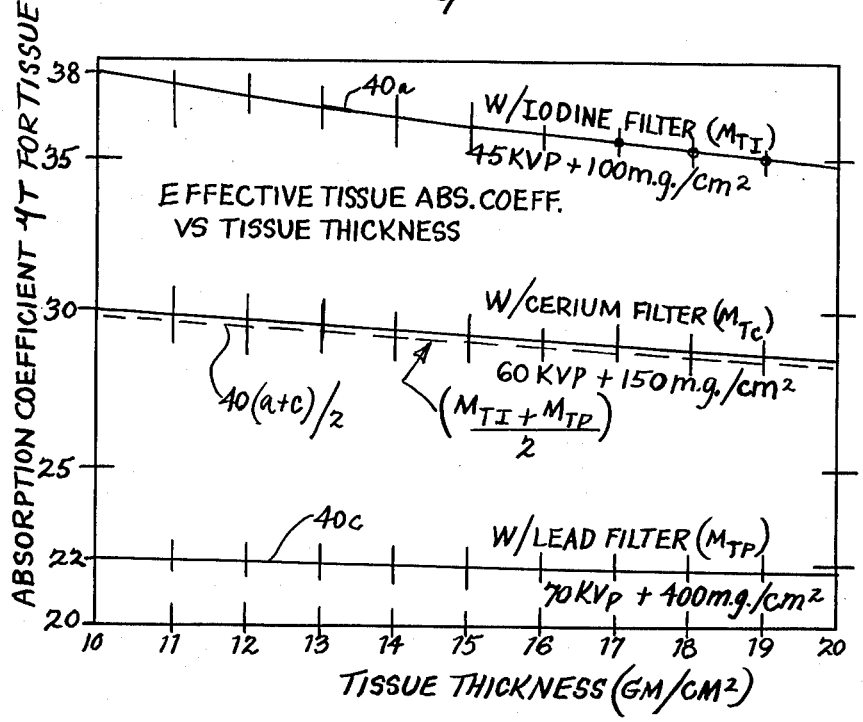
FIG. 14 is a set of graphs in which the effective X-ray absorption coefficient for soft tissue at each tissue thickness is plotted as a function of tissue thickness for the three X-ray spectra.
Figure 15:
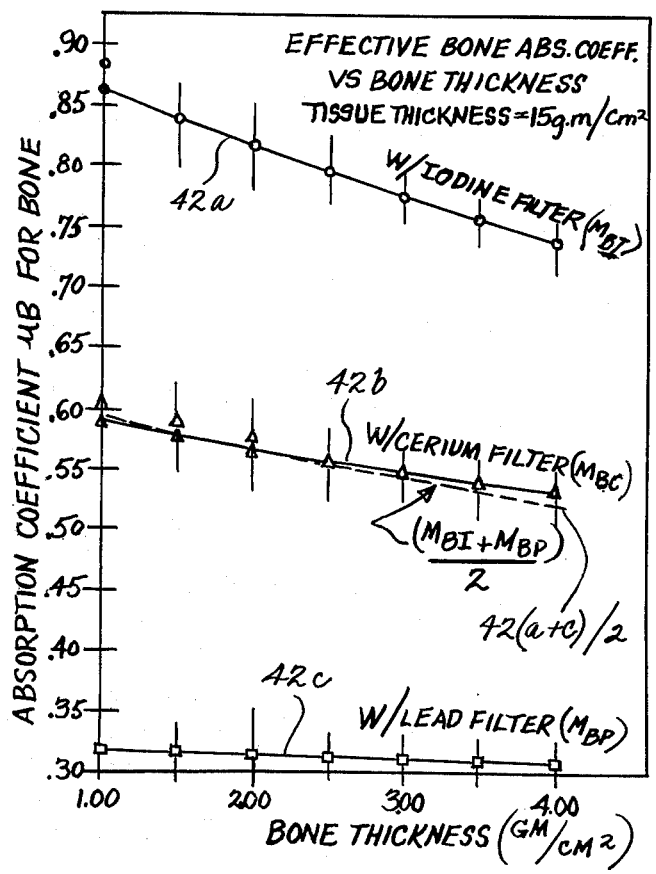
FIG. 15 is another set of graphs in which the effective X-ray absorption coefficient for bone at each bone thickness is plotted as a function of bone thickness for the three X-ray spectra.

The patient thickness compensation of the present invention is illustrated even more clearly in FIGS. 14 and 15. It will be seen that FIG. 14 includes graphs 40a, b and c which are plots of the effective absorption coefficient for soft tissue, as to the three spectra 30a, b and c, produced with the use of the iodine, cerium and lead filters. In each case, the absorption coefficient is plotted as a function of tissue thickness in grams per square centimeter. It will be seen that the effective absorption coefficient decreases gradually with increasing tissue thickness. This is due to the hardening effect upon the X-ray beams as they penetrate increasing quantities of soft tissue. The graph 40a for the iodine filter is higher than the graph 40b for the cerium filter. On the other hand, the graph 40c for the lead filter is lower than the graph 40b for the cerium filter.

FIG. 14 also includes a broken line graph representing the average of the graphs 40a and c for the iodine and lead filters. Such broken line graph is designated 40(a+c)/2. It will be noted that the broken line or average graph runs close to the graph 40b for the cerium filter throughout the range of tissue thickness represented by FIG. 14. Thus, if the average graph 40(a+c)/2 is subtracted from the second graph 40b, in accordance with the method of the present invention, the results will be close to 0. This indicates that the subtraction of the average of the first and third X-ray images from the second X-ray image will largely cancel out the portions of the images due to soft tissue. Thus, the method of the present invention is automatically compensated for variations in the amount or thickness of soft tissue in the patient's body.

FIG. 15 comprises graphs 42a, b and c representing the effective absorption coefficient for bone, plotted as a function of bone thickness, in grams per square centimeter, for the three sprectra, produced with the iodine, cerium and lead filters. FIG. 15 also includes a broken line graph representing the average of the first and third graphs 42a and c, such average graph being designated 42(a+c)/2. Here again, the average graph runs very close to the second graph 42b. If the average graph is subtracted from the second graph, the result will be close to 0, indicating that the bone components of the X-ray images can largely be cancelled out by subtracting the average of the first and third X-ray images from the second X-ray image.

Figure 9:
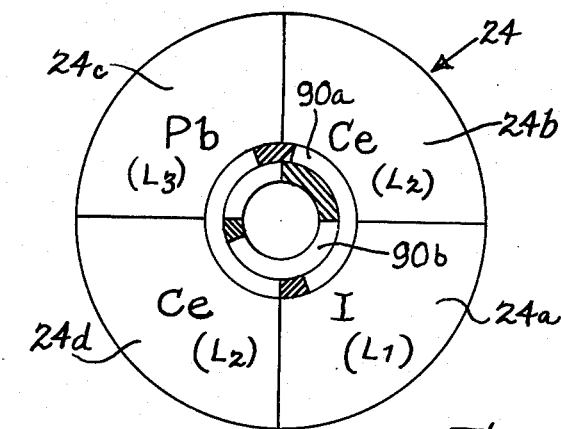
FIG. 9 is a diagrammatic representation of the filter wheel of FIG. 1, showing the four X-ray filters.

FIG. 9 is a diagrammatic illustration of the filter wheel 24, showing the four filters, comprising the iodine filter 24a, the cerium filter 24b, the lead filter 24c, and the second version of the cerium filter 24d. As shown, the filters occupy four equal sectors of the filter wheel 24.

In carrying out the method of the present invention, it is advantageous to employ four filters, rather than three. The fourth filter is a second version or duplicate of the second filter. Four successive X-ray spectra are produced by moving the four filters successively into the X-ray beam. The fourth X-ray spectrum is a duplicate of the second spectrum. Four successive X-ray images are produced by using the four X-ray spectra. The fourth X-ray image is a second version or duplicate of the second image. It is easy to make a subtractive combination of the four images, in a manner which is equivalent to subtracting the average of the first and third X-ray images from the second X-ray image. The equivalent combination is achieved by additively combining the second and fourth images, while subtracting the first and third images therefrom. This procedure results in the production of a differential X-ray image in which the image elements due to the contrast medium are enhanced, while the image elements due to ordinary soft tissue and bone are largely cancelled out.

FIG. 1 illustrates a television system 44 for selectively combining the X-ray images so as to produce a differential X-ray image. However, it will be understood that various methods may be employed to combine the X-ray images, not necessarily involving a television system. Nevertheless, the television system is advantageous, because the television system makes it possible to combine the X-ray images very rapidly and accurately. The speed of the system minimizes the X-ray exposure to which the patient is subjected.

As shown in FIG. 1, the visible X-ray images on the intensification screen 22 are converted into video X-ray images by a TV camera 46, which may be of any known or suitable construction. The details of such TV cameras are well known to those skilled in the art.

The video signals from the TV camera 46 are fed through a gain switching control circuit 48 to a video amplifier 50. The gain switching control circuit 48 is arranged so that the gain or amplification can be switched to three different levels for the three different X-ray spectra, produced by the use of the iodine, cerium and lead filters. By thus changing the gain, it is possible to compensate for the differences in the average intensities of the three X-ray spectra.

From the output of the video amplifier 50, the video signals are fed through a video switch or gate 52 to a video difference detector 54. The video switch 52 makes it possible to supply the video signals to the video difference detector 54 on a selective basis, for the desired portions of the timing cycle. The video switch 52 is controlled by pulse signals received over a control line 52a. The video difference detector 54 is also under the selective control of signals supplied over a control line 54a.

The four video image signals are supplied sequentially to the video difference detector 54, which is constructed and arranged to produce output video signals corresponding very closely to the differences between the successive signals in the sequence of four video image signals. Thus, the video difference detector 54 produces four successive video difference signals, each representing the difference between two successive X-ray images.

The video difference signals from the output of the video difference detector 54 are fed through a second video switch or gate 56 to an integrating subtraction and storage device 58. The video switch 56 makes it possible to supply the video difference signals on a selective basis to the integrating subtraction and storage device 58, preferably under the control of timing pulses supplied over a control line 56a. The operation of the storage device 58 is also controlled by timing signals received over a control line 58a.

The integrating subtraction and storage device 58 is arranged to write and store electronic signals corresponding to the input video difference signals. In producing the electronic images, the input video signals can be written in either a positive or a negative sense. It is preferred to alternately write positively and negatively, in accordance with which X-ray filter is being used. In this way, the image elements due to the contrast medium, such as iodine, are additively written four times, and thus are effectively multiplied by four, while the background elements of the images, due to ordinary soft tissue and bone, are very largely cancelled out.

It is highly advantageous to employ logarithmic video amplification in the video amplifier 50, so that except for constant terms the four video images will be proportional to the absorption coefficients. With logarithmic amplification, it is possible to achieve much better cancellation of the image elements due to ordinary soft tissue and bone.

The differential portions of the video difference signals, due to the contrast medium, are integrated by the storage device 58. By operating the system through a plurality of cycles of the filter wheel, the differential image element due to the constrast medium are progressively integrated to higher and higher levels, so that the visibility of the contrast medium is greatly enhanced.

The integrating subtraction and storage device 58 can be read to produce output video signals representing the integrated image stored in the storage device. These output video signals are supplied through another video switch 60 to a television monitor 62 which produces a visible display of the differential X-ray image, as stored in the storage device 58. In such image, the differential features or elements due to the contrast medium are greatly enhanced so that they become clearly visible, even though they may have been scarcely visible or even invisible in the original X-ray images. Differential features having an original contrast of less than 1% can be enhanced to have much greater contrast, corresponding approximately to the full contrast range of the television system.

The television system 24 includes a TV sync and sweep generator 64, adapted to supply television synchronizing pulses and sweep signals to the television camera 46, and also to the video difference detector 54 and the integrating subtraction and storage device 58. Thus, horizontal and vertical sweep signals are supplied by the generator 64 over signal lines 64x and 64y to the TV camera 46, the video difference detector 54 and the storage device 58. The television sweep and sync generator 64 may be of any known or suitable construction. Such generators are well known to those skilled in the art.

Timing circuits 66 are provided to coordinate the operation of the television system, particularly the video difference detector 54, the integrating subtraction and storage device 58, and the associated components. Thus, the timing circuits 66 supply control signals to the gain switching control 48, over one or more control lines 48a. Control signals for the video switch 52 are supplied from the timing circuits 66 over the control line 52a. The second video switch 56 is supplied with control signals from the timing circuits 66 over the control line 56a. The control signals for the video switch 60 are supplied from the timing circuits 66 over a control line 60a.

The video difference detector 54 is operated in different modes during different portions of the timing cycle. In this case, the video difference detector 54 is operated in a clear mode or a write mode. For the clear mode, a relatively high operating voltage is supplied to the video difference detector 54 over the control line 54a by a clear gate 68. Timing pulses to control the clear gate 68 are supplied by the timing circuits 66 over a control line 68a.

During the write mode, a relatively low operating voltage is supplied to the video difference detector 54 over the control line 54a by a write gate 70. Timing signals to control the operation of the write gate 70 are supplied by the timing circuits 66 over a control line 70a.

In preparation for operation, the integrating subtraction and storage device 58 is preferably operated in a prime mode, during which a relatively high operating voltage is supplied to the storage device 58 over the control line 58a by a prime control circuit 72. The prime mode may be controlled either automatically or manually. In this case, a manually operable prime switch 74 is connected to the prime control circuit 72 to control the prime mode.

In further preparation for normal operation, it is preferred to operate the storage device 58 in an erase mode, during which a moderately low operating voltage, such as 20 volts, for example, is supplied to the storage device 58 over the supply line 58a by an erase control circuit 76, which may be controlled either automatically or manually. In this case, a manually operable erase control switch 78 is connected to the erase control circuit 76, to control the erase mode.

During normal operation, the storage device 58 is operated in either a positive write mode or a negative write mode. During the positive write mode, a moderate operating voltage, such as 50 volts, for example, is supplied to the storage device 58 over the control line 58a by a positive write gate 80, which is controlled by timing signals received from the timing circuits 66 over a control line 80a. During the negative write mode, a lower operating voltage is supplied to the storage device 58 over the supply line 58a by a negative write gate 82, which is supplied with control signals by the timing circuits 66 over a control line 82a.

When the storage device 58 is not in a positive write mode or a negative write mode, it is switched into a read mode, under the control of a read gate 84, which supplies a low operating voltage, such as 6 volts, for example, to the storage device 58 over the control line 58a. The read gate 84 is controlled by signals received from the timing circuits over a control line 84a.

In the system 10 of FIG. 1, a start-stop switch 86 is connected to the timing circuits 66 to start and stop the processing of the television signals. The start-stop switch 86 may be operated either automatically or manually. In this case it is operated manually.

Figure 5:
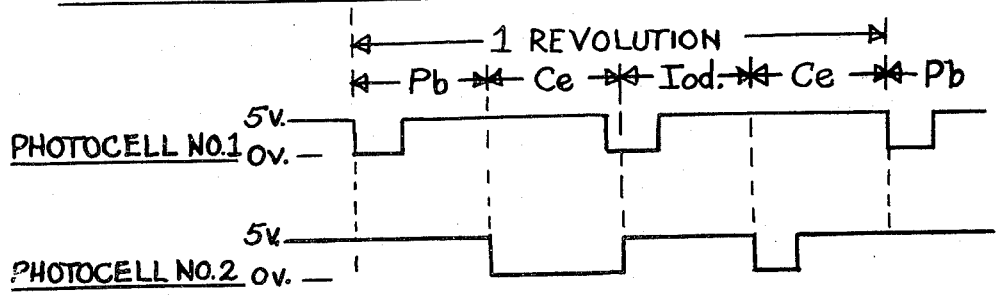
FIG. 5 is a diagram illustrating the control tracks for the photocells which are employed in the system of FIG. 1 to coordinate the timing circuits with the rotation of the X-ray filter wheel.

It is desirable to coordinate the operation of the timing circuits 66 with the rotation of the filter wheel 24. In this case, such coordination is achieved by providing first and second photocells 88a and b having their outputs connected to the timing circuits 66. The photocells 88a and b are operated by timing tracks 90a and b on the filter wheel 24. Light from lamp 92 shines through the timing tracks 90a and b to the photocells 88a and b. The details of the timing tracks 90a and b are shown in FIG. 9. In addition, FIG. 5 is a diagrammatic view showing the wave form of the signals produced by the photocells 88a and b. The wave form corresponds to the shape of the timing tracks 90a and b.

For synchronizing purposes, the vertical synchronizing pulses for the television system 44 are supplied to the timing circuits 66 over a control line 94, extending from the TV sync and sweep generator 64.

The video difference detector 54 may employ various electronic storage tubes and other difference detecting devices. In the system 10 of FIG. 1, it is preferred to employ an electronic storage tube 96 of the general type illustrated in FIG. 2. The storage tube 96 is of a type which has been used as a moving target indicator for radar systems or other surveillance systems. Tubes of this type are manufactured by Princeton Electronic Products, Inc. and Hughes Aircraft Company. A storage tube type PEP-700, made by Princeton Electronic Products, Inc. has been used successfully.

Figure 2:
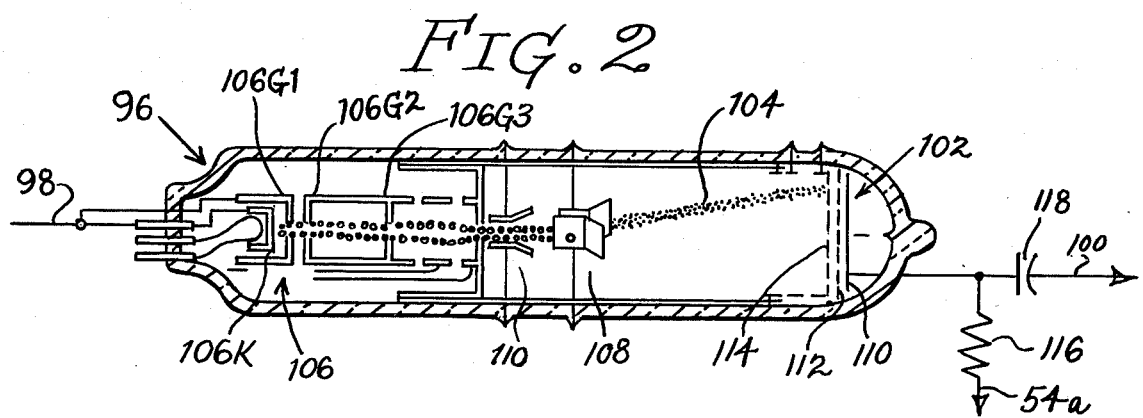
FIG. 2 is a diagrammatic longitudinal section showing a video difference detector tube employed in the system of FIG. 1.

As shown, the storage tube 96 of FIG. 2 is employed in an operating circuit including a video input line 98 and a video output line 100. The video signals from the TV camera 46, arriving through the video amplifier 50 and the video switch 52, are applied to the input line 98. During the first TV frame, similar video signals appear on the output line 100. However, the magnitude of the output video signals decreases with each passing TV frame, as the tube 96 comes toward equilibrium. Any changes in the input video signals from frame to frame are transmitted with full magnitude, but the unchanged or non-differential portions of the video signals from frame to frame are largely cancelled out as the tube approaches equilibrium.

The storage tube 96, as illustrated in FIG. 2, has a special target 102 but otherwise may be similar in construction to a conventional vidicon cathode ray camera tube, used in TV cameras. The target 102 is scanned by an electron beam or cathode ray 104, produced by a conventional electron gun 106, which may include a cathode 106K and three grids 106G1, 106G2 and 106G3. The input line 98 is preferably connected to the cathode 106K, and also preferably to the first grid 106G1. Thus, the electron beam 104 is modulated by the video input signals.

Means are provided to deflect the electron beam 104 in the storage tube 96 of FIG. 2. Either magnetic or electrostatic deflection may be employed. For illustrative purposes, the storage tube 96 is shown as having horizontal and vertical deflection plates 108 and 110, which may be supplied with horizontal and vertical sweep or scanning signals from the TV sweep generator 64 of FIG. 1. However, magnetic deflection coils can be emloyed instead of the deflection plates. One or more magnetic focusing coils may also be employed.

The target 102 of the storage tube 96, shown in FIG. 2, may take the form of an electrically conductive backplate or signal plate 110 having a thin dielectric layer or facing 112 thereon. A collector electrode 114 is provided adjacent the target 102.

The conductive backplate 110 may be made of doped silicon, while the dielectric facing 112 may comprise a thin layer of silicon dioxide ($SiO_2$) grown thereon. The dielectric layer 112 is adapted to be charged electrostatically by the electron beam 104, so that electrostatic television images can be written electrostatically on the layer 112 by the electron beam 104.

In the illustrative arrangement of FIG. 2, a load in the form of a resistor 116 is connected between the backplate 110 and the control line 54a, to which different power supply voltages may be applied by the clear gate 68 and the write gate 70. If desired, a coupling capacitor 118 may be connected between the backplate 110 and the video output line 100.

There is capacitive coupling only between the charged front surface of the dielectric layer 112 and the backplate 110. During the operation of the system 10 of FIG. 1, it is generally preferred to operate the first storage tube 96 in the clear mode for one TV frame, prior to writing the first video X-ray image on the tube. In the clear mode, the target backplate 110 is raised to a fairly high positive voltage, such as 100 to 340 volts, while the electron beam is operated without modulation. This has the effect of spraying electrons uniformly over the front face of the dielectric layer 112. The positive voltage thus imparted to the front face of the dielectric layer is on the order of 1 volt or so.

Following the single TV frame in the clear mode, the first storage tube 96 is switched to the write mode, in which a relatively low positive voltage is applied to the target backplate 110. Such target voltage may be approximately 1 to 30, for example. A brief waiting interval is generally provided, before the first video X-ray image is written on the tube 96. This waiting interval may amount to two or more TV frames, during which the high voltage applied to the X-ray tube 16 has time to stabilize. The waiting interval also allows time for the TV camera 46 and the gain switching control circuits 48 to stabilize.

The video signals corresponding to the first X-ray image are then applied to the input line 98. In this way, the first video X-ray image is written by the electron beam 104 on the front face of the dielectric layer 112. This image may be the one produced with the use of the iodine filter 24a. The image is written by the electron beam 104 in the form of electrostatic charges on the dielectric layer 112 of the target 102 in the storage tube 96. During the first television frame in the write mode, the electron beam 104 distributes charges on the dielectric layer 112, corresponding to the video signals. Due to the capacitive coupling through the thin dielectric layer 112, the charging of the layer 112 produces displacement currents to the backplate 110 through the load resistor 116, so that video signals are supplied to the output line 100. During subsequent TV frames, a state of equilibrium tends to be established between the video voltages on the cathode 106K and the voltages due to the charges on the front surface of the dielectric layer 112. As the state of equilibrium is approached, the charging currents along the electron beam tend to drop to zero, so that the video output currents also tend to drop zero. Thus, the image elements which do not change from frame to frame tend to be cancelled out.

Before full equilibrium is established, the first storage tube 96 is generally operated for one TV frame in the clear mode. As before, this operation sprays electrons uniformly over the entire front surface of the dielectric layer 112. Because the secondary electron emission is greater than the primary electron current, the entire front surface of the dielectric plate goes slightly more positive by a volt or so. Following the clear, there is generally a waiting interval of two or more TV frames, to allow time for the high voltage supplied to the X-ray tube 16 to stabilize. Meanwhile, the tube 96 is switched to the write mode, during which the target backplate 110 is operated at a low positive voltage of approximately 1 to 30 volts. After the waiting interval, the video signals corresponding to the second X-ray image are applied to the input line 98. This may be the X-ray image produced with the cerium filter 24b.

At the beginning of the second writing interval, the first electrostatic image is still on the front face of the dielectric layer 112, offset by a volt or so. Thus, only the differences between the second X-ray image and the first X-ray image result in video signal currents along the electron beam 104. Thus, the output video signals on the output line 100 correspond to the differences between the second X-ray image and the first X-ray image. The one volt clear results in a direct current offset which gradually dissipates. The effects of the direct current offset are cancelled by the alternate positive and negative writing of the second storage tube 120.

Thus, the first storage tube 96 produces differential video output signals corresponding to the differences between the second and the first X-ray images. The nondifferential features of these images are largely cancelled out. Because full equilibrium is not achieved in the writing of the video images, the cancellation is not complete. It is desirable to avoid reaching full equilibrium, because with only partial equilibrium, it is possible to detect video signal changes which are both positive and negative in sign.

The third and fourth X-ray images are similarly written on the first storage tube 96 when the lead filter 24c and the second cerium filter 24d move into the X-ray beam. In each case, the first storage tube 96 produces output video signals corresponding to the differences between the successive X-ray images. This subtracting action produces a great enhancement of the portions of the X-ray images which are caused by the iodine or other contrast medium.

After passing through the video switch 56, the output video signals from the first storage tube 96 are combined and integrated by the integrating subtraction and storage device 58 of FIG. 1. Such storage device 58 may comprise a second electronic storage tube. It will be understood that storage tubes of various types may be employed. However, it is preferred to employ an electronic storage tube 120 of the general type shown in FIG. 3. The illustrated tube is of the silicon storage type, such as the type PEP-400, manufactured by Princeton Electronic Products, Inc., which has been found to be satisfactory.

Figure 3:
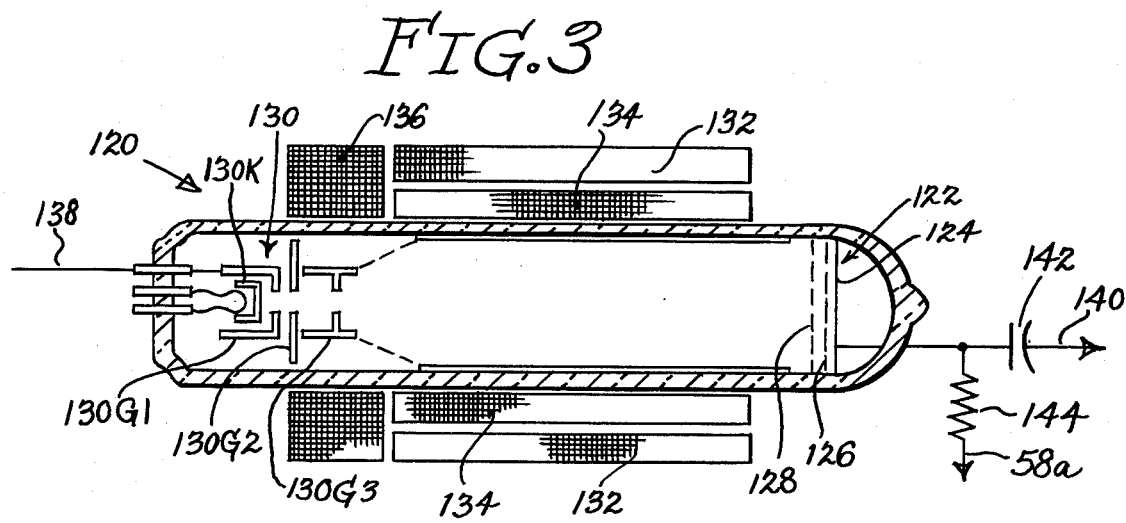
FIG. 3 is a diagrammatic longitudinal section showing a silicon storage tube employed in the second video subtraction stage of the system shown in FIG. 1.

The silicon storage tube 120 of FIG. 3 has a special target 122 comprising an electrically conductive backplate or or signal plate 124 with a mosaic 126 thereon of dielectric islands. Preferably, the backplate 124 is made of doped silicon, while the mosaic 126 comprises islands of silicon dioxide ($SiO_2$) selectively grown thereon.

Aside from the target 122, the second storage tube 120 may be similar to a conventional vidicon cathode ray camera tube as used in television cameras. A collector electrode 128 is provided adjacent the target 122.

The mosaic 126 on the target 122 is scanned by an electron beam or cathode ray produced by a conventional electron gun 130 having a cathode 130K and three grids 130G1, 130G2 and 130G3. Either magnetic or electrostatic deflection may be employed. In this case, deflection coils 116 are provided to produce magnetic deflection. Alignment coils 134 and a focusing coil 136 may also be provided.

The differential video signals from the first storage tube 96 may be supplied to the second storage tube 120 by way of the output line 100, the video siwtch 56 and an input line 138, which in this case is connected to the first grid 130G1 of the second storage tube 120. Thus, the electron beam current is modulated by the differential video signals.

The output of the second storage tube 120 is preferably derived from the backplate 124 of the target 122. Thus, the backplate 124 is coupled to an output line 140, preferably through a coupling capacitor 142. In the illustrated arrangement, a load in the form of a resistor 144 is connected between the backplate 124 and the control line 58a, also shown in FIG. 1. It will be recalled that the various power supply voltages are applied to the lead 58a by the prime control 72, the positive write gate 80, the negative write gate 82, the read gate 84, and the erase control 76.

The second storage tube 120 is employed to write electrostatic images on the mosaic 126 of the target 122, corresponding to the differential video signals from the first storage tube 96, by applying such differential video signals to the input line 138, which transmits the signals to the first grid 130G1 of the storage tube 120. The video images can be written in either a positive or a negative sense, depending upon the voltage which is supplied to the backplate 124.

Figure 4:
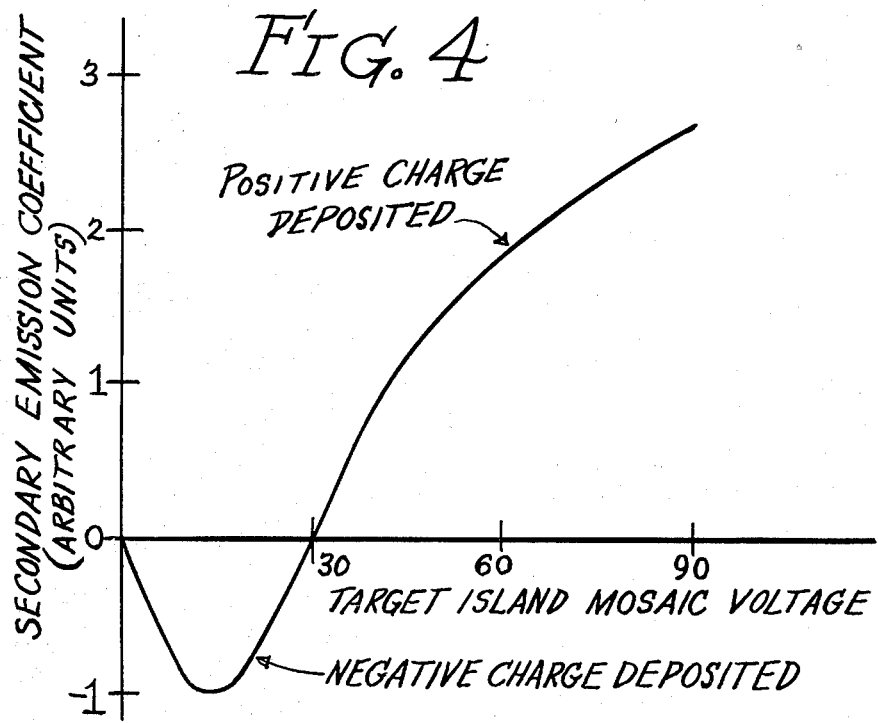
FIG. 4 is a graph representing the writing characteristics of the silicon storage tube of FIG. 3, such graph being effective to illustrate how images can be written either positively or negatively on such storage tube.

The ability to write either positively or negatively is illustrated by the characteristic curve of FIG. 4, in which the secondary emission coefficient of the target island mosaic 126 is plotted as a function of the target island mosaic voltage. When the electron beam impinges upon the target islands of the mosaic 126, secondary electrons are emitted by the target islands in increasing numbers with increasing target island voltage, above a crossover voltage of about 30 volts.

As plotted in FIG. 4, the secondary emission coefficient is the net number of secondary electrons emitted for each primary electron supplied by the electron beam. When the coefficient is greater than zero, the electron beam writes images with positive charges on the target mosaic 110 because each primary electron from the electron beam causes the emission of more than one secondary electron from the target island mosaic 126. When the coefficient is negative, the electron beam writes images with negative charges, because each primary electron causes the emission of less than one secondary electron on the average. The backplate voltage at which the coefficient is zero may be called the crossover voltage. Above crossover, which is about 30 volts for the characteristic curve shown in FIG. 4, the electron beam causes a net deposit of positive charges on the islands of the mosaic 110. Below crossover, the electron beam causes a net deposit of negative charges.

The second storage tube 120 is caused to alternate between positive writing and negative writing, while successive X-ray images are being produced by the use of the filters 24a–d. Thus, for example, while the first X-ray filter is being used to produce the first X-ray spectrum, the second storage tube 120 may be caused to write positively. When the second X-ray filter is being used to produce the second X-ray spectrum, the second storage tube 120 may be caused to write negatively. When the third X-ray filter is being employed to produce the third X-ray spectrum, the second storage tube 120 may be caused to write positively. When the fourth X-ray filter is being employed to produce the fourth X-ray spectrum, the second storage tube may be operated to write negatively. This cycle may be repeated for two or more revolutions of the filter wheel 24.

The effect of this cycle is to write the image elements due to the contrast medium, iodine, additively during all four portions of the cycle, while the image elements due to soft tissue and bone are alternately written additively and subtractively, so that they cancel out almost completely. The second storage tube 120 integrates the positively written image elements due to the contrast medium, during successive complete cycles of the filter wheel. This integrating action still further enhances the image elements due to the contrast medium.

For positive writing, the voltage of the backplate 126 in the second storage tube 120 is switched to a positive value above the crossover voltage of about 30 volts. The positive writing backplate voltage may be about 50 volts, for example. For negative writing, the backplate voltage is switched below 30 volts. For example, a backplate voltage of about 10 volts has been found to be satisfactory. When it is desired to read the integrated image on the target mosaic 126 of the second storage tube 120, the target voltage may be switched to a low value, such as about 6 volts, for example. The target mosaic 126 is then scanned with the electron beam. This reading procedure produces video signals on the backplate 124, because the electrical charges on the target mosaic 126 modulate the electron beam as it passes the mosaic island on its way to the backplate 124. At the low target voltage of only about 6 volts, the electron beam causes very little change in the charges on the target mosaic 126.

It will be understood that the backplate voltage of 6 volts for the read mode is given by way of example only, and that this voltage may be varied over a considerable range. The read voltage is supplied to the backplate 124 by the read gate 84, which is normally activated when the second storage tube is not in any other mode, such as write, prime or erase.

During the reading operation, the video signals from the backplate 124 of the second storage tube 120 are supplied to the television monitor 62 over the output line 140 and the video read switch 60. The visible image produced by the monitor 62 corresponds to the differential X-ray image on the target mosaic 126 of the second storage tube 120.

Before beginning the operation of the television system 44 of FIG. 1, it is generally desirable to operate the second storage tube 120 in the prime mode for one TV frame, and then in the erase mode for one or more TV frames. These operations remove any residual image from the target mosaic 126. During the prime mode, the voltage of the target backplate 124 is switched to a relatively high positive level, such as 140 volts, for example, by the prime control circuit 72. At the same time, the electron beam is allowed to scan the target mosaic 126 without any modulation. As a result, electrons are sprayed uniformly over the target mosaic 126.

When the storage tube 120 is switched to the erase mode, the voltage of the target backplate 124 is reduced below crossover, while the electron beam is caused to scan the target mosaic 126 without beam current modulation. For example, the target backplate 124 may be switched to about 20 volts by the erase control circuit 76. During the erase operation, the electron beam writes negatively over the entire target mosaic 126 at a uniform rate, so that the target mosaic comes to a uniform negative voltage, which tends to establish an equilibrium condition between the target mosaic and the cathode 130K. Any previous electrostatic image is wiped off the target mosaic 126.

The details of the electronic circuits for the X-ray system are subject to wide variation. Those skilled in the art will be able to construct appropriate electronic circuits, based on the foregoing description. However, by way of example, detailed electronic circuits are shown in FIGS. 16–21.

Figure 16:
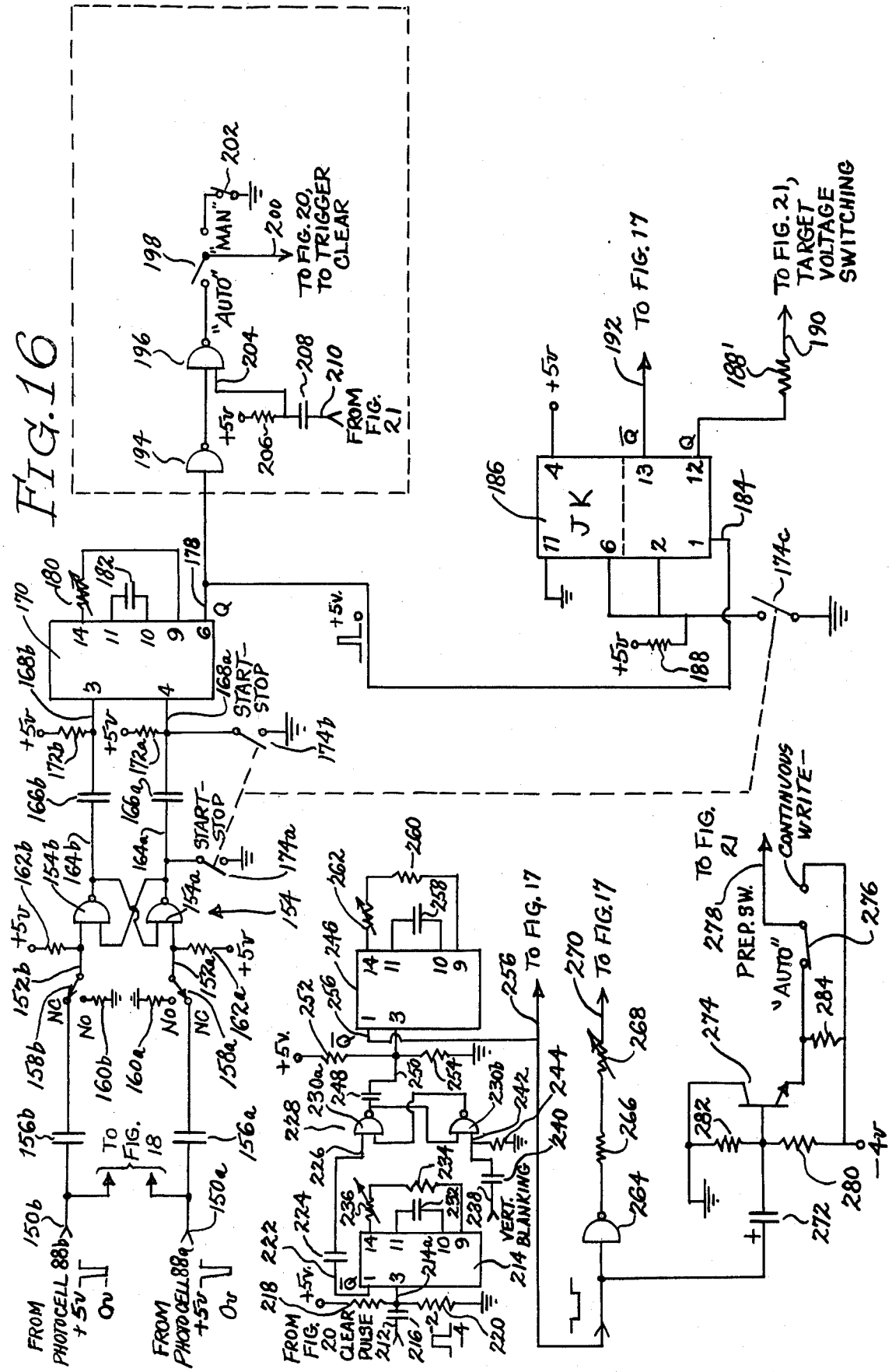
FIG. 16 is a schematic diagram showing timing circuits for the X-ray system of FIG. 1.

With reference to FIG. 16, means are preferably provided to coordinate the timing of the television system with the rotation of the X-ray filter wheel 24. The outputs of the photocells 88a and b are connected to input lines 150a and b, as shown in FIG. 16. The input lines 150a and b are connected to the inputs 152a and b of an RS flip-flop 154, utilizing cross-connected NAND gates 154a and b through coupling capacitors 156a and b and switches 158a and b. As shown in FIG. 16, the switches 158a and b are in their normal operating positions. For manual simulation of the operation of the photocells, the switches 158a and b may be alternately moved to normally open positions, in which the switches 158a and b connect the inputs 152a and b to ground through resistors 160a and b. In this case, a bias source, such as +5 volts, or some other suitable voltage, is supplied to the inputs 152a and b through resistors 162a and b.

The gates 154a and b have outputs 164a and b which are connected through coupling capacitors 166a and b to the inputs 168a and b of a monostable 170, which may be in the form of a commercially available integrated circuit, Type 74121. The inputs 168a and b are connected through resistors 172a and b to a bias source, such as +5 volts.

Three start-stop switches 174a, b and c are preferably provided for use in starting and stopping the operation of the television system. As shown, the switch 174a is connected between the flip-flop output 164a and ground. In the start position, the switch 174a is open. In the stop position, the switch 174a is closed, so as to short circuit the output 164a to ground.

The second start-stop switch 174b is connected between the monostable input 168a and ground. The switch 174b is closed in its stop position and open in its start position. The connection of the third start-stop switch 174c will be described presently. It will be understood that the three switches 174a, b and c are preferably ganged together for simultaneous operation.

In its stop position, the switch 174a sets the flip-flop output 164a to zero. When the switches 174a, b and c are opened, the flip-flop output 164a remains at zero until the iodine filter is moved into the X-ray beam, whereupon the photocell signals cause the flip-flop 154 to reverse, so that the output 164a goes high. This triggers the monostable 170, which produces a timed pulse at its Q output 178. The length of the pulse 178 is determined by a variable resistor 180 and a capacitor 182 connected to the monostable 170. The output pulse from the monostable 170 is fairly brief, being considerably less than one TV frame, but is sufficiently long to insure that the subsequent functions triggered by this pulse will be reliably initiated.

The brief pulse from the monostable output 178 goes to the clock input 184 of a JK flip-flop 186, which may be in the form of a commercially available integrated circuit, Type 7473. The third start-stop switch 174c is connected between the presetting inputs of the flip-flop 186 and ground. Such presetting inputs are also connected through a resistor 188 to a bias source, such as +5 volts. In its stop position, the switch 174c is closed so as to prevent the flip-flop 186 from firing. In its start position, the switch 174c is open so as to enable the flip-flop 186 to fire. The flip-flop 186 keeps track of which filter is positioned in the X-ray beam, and is effective to trigger subsequent circuits, as will be described in detail presently. The Q output of the flip-flop 186 is connected through a resistor 188' to an output line 190 which extends to the circuits of FIG. 21, for controlling the operation of the second storage tube 120. The $\overline{Q}$ output of the flip-flop 186 is connected to an output line 192 which goes to FIG. 17, to control the video input to the first storage tube 96.

Figure 20:
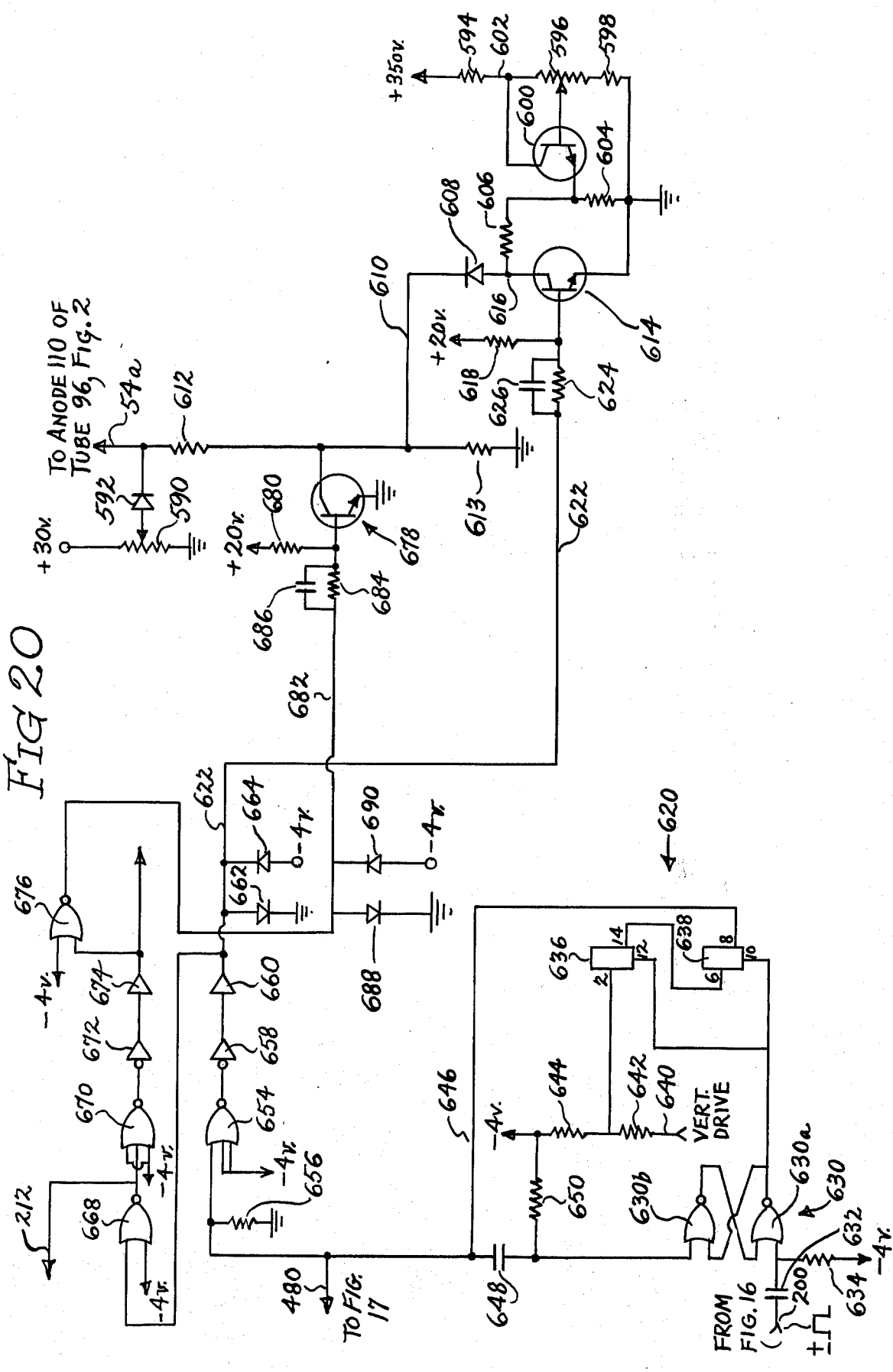
FIG. 20 is a schematic diagram showing control circuits for the first video storage tube.

The Q output 178 of the monostable 170 is also connected through two successive NAND gates 194 and 196 and a changeover switch 198 to an output line 200 which extends to FIG. 20 and provides a brief pulse to control the operation of the first storage tube 96. The switch 198 has an automatic position in which the output of the gate 196 is connected to the output line 200, and a manual position, in which the line 200 is connected to ground through a control switch 202.

The gate 196 has an input 204 which is connected through a resistor 206 to a bias source, such as +5 volts. The input 204 is also connected through a coupling capacitor 208 to an input line 210 which is connected to the circuits of FIG. 21 and is adapted to supply a pulse whenever the second storage tube 120 is switched into its erase mode. This produces a pulse at the output line 200.

The pulse at the output line 200 causes the first storage tube 96 to go into a clear mode, which is timed by the circuits of FIG. 20. Generally, the clear mode lasts for one TV frame. The circuits of FIG. 20 supply a clear pulse corresponding in duration to the clear mode. This clear pulse is supplied to an input line 212 in FIG. 16. Means provided to insert a delay, or a waiting interval, after the end of the clear pulse, before the first storage tube 96 is switched into a write mode. In the circuits of FIG. 16, such a delay is provided by a monostable 214, which may be in the form of a commercially available integrated circuit, Type 74122. The input line 212 is connected through a coupling capacitor 216 to the input of the monostable 214. The monostable input 214a is connected through a resistor 218 to a bias source, such as +5 volts. A resistor 220 is connected between the input 214a and ground.

A timed pulse is supplied by the $\overline{Q}$ output 222 of the monostable 214 through a coupling capacitor 224 to one input 226 of an RS flip-flop 228, comprising cross-connected NAND gates 230a and b. The duration of the monostable output pulse is determined by a capacitor 232 and two resistors 234 and 236 connected in series, the resistor 236 being variable. Generally, the duration of the monostable output pulse is adjusted to at least two TV frames, and more often to several frames. This pulse provides a delay which allows time for the high voltage to the X-ray tube to stabilize. Moreover, this delay allows the TV camera 46 to stabilize when presented with the new X-ray image.

The flip-flop 228 is set by the delay pulse from the monostable 214. After the end of the delay pulse, the flip-flop 228 is reset by the next vertical blanking pulse from the TV sync generator 64. The TV blanking pulses are supplied to an input line 238, which is connected through a coupling capacitor 240 to the input 242 to the NAND gate 230b. A resistor 244 is connected between the input 242 and ground. The resetting of the flip-flop 228 by the blanking pulses insures that the delay will be terminated at the end of a TV frame.

Means are provided to time the write mode of the first storage tube 96. In the circuits of FIG. 16, this is done by a monostable 246, which may take the form of a commercially available integrated circuit, Type 74121. The output of the gate 230a is connected through a coupling capacitor 248 to the input 250 of the monostable 246. In this case, the input 250 is connected through a resistor 252 to a bias source, such as +5 volts. A resistor 254 is connected between the input 250 and ground.

The monostable 246 supplies a timed pulse at its $\overline{Q}$ output 256. The duration of the pulse is determined by a capacitor 258 and two resistors 260 and 262 connected in series, the resistor 262 being variable. Generally, the monostable output pulse extends for several TV frames, such as six frames, for example.

Figure 17:
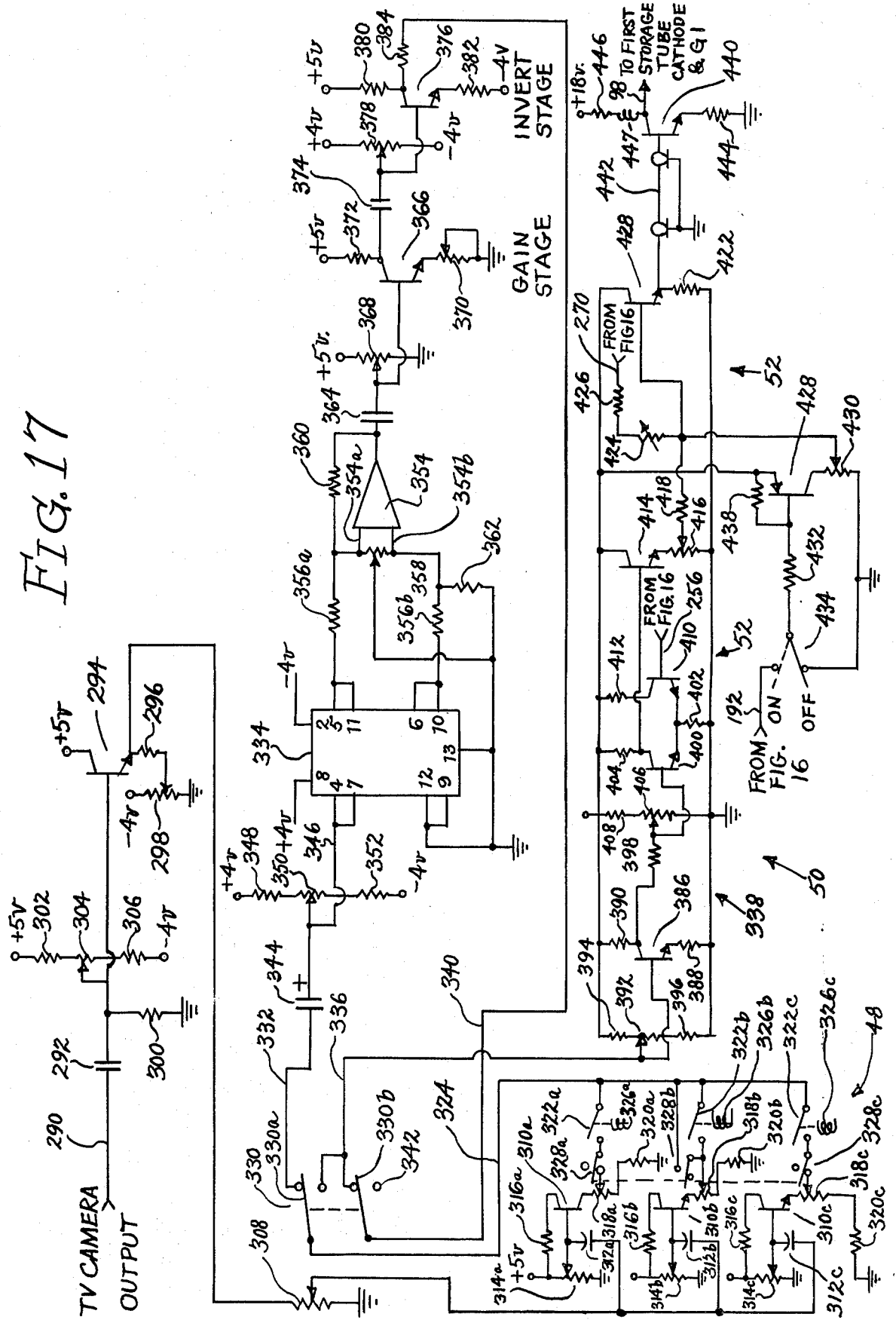
FIG. 17 is a schematic diagram showing video amplification and switching circuits.

In this case, the $\overline{Q}$ output 256 is connected through a NAND gate 264, a fixed resistor 266 and a variable resistor 268 to an output line 270 which extends to FIG. 17 and is employed to control the video signals supplied to the first storage tube 96.

The $\overline{Q}$ monostable output 256 is also connected through a coupling capacitor 272 to the base of a transistor 274 having its emitter connected through a preparatory switch 276 to an output line 278. In this case, the output line 278 extends to FIG. 21 and controls the write mode of the second storage tube 120.

The base of the transistor 274 is connected through a resistor 280 to a bias source, such as −4 volts. A resistor 282 is connected between the base and ground. The collector of the transistor 274 is connected to ground, while the emitter is connected through a load resistor 284 to a power source, such as −4 volts.

In this case the preparatory switch 276 is movable between an automatic position, in which the output line 278 is connected to the emitter of the transistor 274, and a continuous write position, in which the output line 278 is connected to −4 volts. The continuous write position is used when the second storage tube 120 is being primed.

FIG. 17 shows details of the gain switching control circuits 48, the video amplifier 50 and the video switch 52, which are connected between the TV camera 46 and the first storage tube 96 in the video difference detector 54. Thus, the output of the TV camera 46 is supplied to an input line 290 in FIG. 17. The input line 290 is connected through a coupling capacitor 292 to the base of a transistor 294 which is employed as a sync clipper. The collector of the transistor 294 may be connected directly to a power source, such as +5 volts. The emitter of the transistor 294 is connected through a load resistor 296 to the slider of a potentiometer 298 having its opposite ends connected to −4 volts and ground. The adjustment of the potentiometer 298 regulates the sync clipping action.

As shown in FIG. 17, a resistor 300 is connected between the base of the transistor 294 and ground. A variable operating bias for the base of the transistor 294 is provided by a fixed resistor 302, a potentiometer 304 and another fixed resistor 306, connected in series between +5 volts and −4 volts. The slider of the potentiometer 304 is connected to the base of the transistor 294.

The gain switching circuit 48 acts as a three channel multiplexer and provides a separate gain control for each channel, so that the gain can be adjusted separately when each of the three different filters is being used. The output from the emitter of the transistor 294 is connected to a potentiometer 308 which acts as a master gain control and is connected between the emitter and ground. The gain switching circuit 48 utilizes three transistors 310a, b and c, one for each channel. The slider of the potentiometer 308 is connected to the bases of the transistors 310a, b and c through coupling capacitors 312a, b and c. The bases of the transistors 310a, b and c are supplied with biasing voltages by potentiometers 314a, b and c, each of which is connected between +5 volts and ground, the slider of each potentiometer being connected to the corresponding transistor base. The emitters of the transistors 310a, b and c are connected to +5 volts by resistors 316a, b and c.

The emitters of the transistors 310a, b and c are connected to gain control potentiometers, 318a, b and c which are connected in series with resistors 320a, b and c to ground. Selector switches 322a, b and c are interposed between the sliders of the potentiometers 318a, b and c and a common output line 324. In this case, the selector switches 322a, b and c are in the form of relay contacts operated by relay coils 326a, b and c. These relay coils 26a, b and c are operated by the circuits of FIG. 18, in accordance with the movement of the three different X-ray filters into the X-ray beam. Thus, for example, the relay coils 326a, b and c may be operated for the iodine, cerium and lead filters.

In FIG. 17, three manually operable changeover switches 328a, b and c are also provided to changeover between three channel and single channel operation. The three switches may be ganged together for simultaneous operation. As shown, the changeover switches 328a and c are connected in series with the selector switches 322a and c and are adapted to be closed for three channel operation, while being open for single channel operation. The opening of these switches disables the first and third channels. The second changeover switch 328b is connected in parallel with the second selector switch 322b and is adapted to be open for three channel operation while being closed for single channel operation. When closed, the switch 328b short circuits the selector switch 322b, so that the second channel is always in the circuit for single channel operation.

In FIG. 17, the output line 324 goes to a changeover switch 330 which selects between logarithmic and linear video amplification. The switch 330 has two switch sections 330a and b. The first switch section 330a switches the output line 324 between an input line 332 extending to a logarithmic video amplifier 334, and an input line 336, extending to a linear video amplifier 338. The second switch section 330b is connected to a line 340 extending from the output of the logarithmic video amplifier 334, and is effective to switch the output line 340 between the input line 336 and an unconnected contact point 342. It is generally advantageous to employ the logarithmic video amplifier 334, which may take the form of a commerically available integrated circuit, Type SN76502. As shown, the input line 332 is connected through a coupling capacitor 334 to the input 346 of the logarithmic amplifier 334. The input 346 is also connected to a biasing circuit, comprising a fixed resistor 348, a potentiometer 350 and another resistor 352, connected in series between bias sources, such as +4 volts and −4 volts. The slider of the potentiometer 350 is connected to the input 346.

As shown in FIG. 17, the outputs of the logarithmic amplifier 334 are connected to the inputs of an operational amplifier 354, through resistors 356a and b. The operational amplifier 354 is employed as a video amplifier and may take the form of a commercially available integrated circuit, Type 733. A balancing potentiometer 358 is connected between the inputs 354a and b of the amplifier 354, the slider of the potentiometer 358 being grounded. In this case, a feedback resistor 360 is connected between the input 354a and the output of the amplifier 354. A balancing resistor 362 is connected between the input 354b and ground.

The output of the amplifier 354 may be connected through a capacitor 364 to the base of a transistor 366, employed in a gain adjusting stage. The base of the transistor 366 is biased by a potentiometer 368 connected between ground and a voltage source, such as +5 volts, the base being connected to the slider of the potentiometer. A gain adjusting variable resistor 370 is connected between the emitter of the transistor 366 and ground. The collector is connected through a load resistor 372 to a voltage source, such as +5 volts.

The output of the transistor 366 is taken from the collector, which is connected through a coupling capacitor 374 to the base of a transistor 376, which is employed as an inversion stage. The base is connected to the slider of a biasing potentiometer 378 which is connected between positive and negative voltage sources, such as +4 and −4 volts. The collector of the transistor 376 is connected through a load resistor 380 to a voltage source, such as −5 volts. The emitter is connected through a resistor 382 to a voltage source, such as −4 volts. The output of the transistor 376 is supplied through a resistor 384 to the output line 340, which, as previously described, is connected to the switch 330b. The switch 330b is adapted to connect the output line 340 to the input line 336 of the linear video amplifier 338.

It will be understood that the construction of the video amplifier 338 may be varied. In this case, the input line 336 is connected to the base of a transistor 386 having an emitter resistor 388 connected to ground, and a collector resistor 390 connected to a voltage source, such as +5 volts. The base is connected to the slider of a biasing potentiometer 392, connected in series with resistors 394 and 396 between +5 volts and ground. The output of the transistor 386 is taken from the collector and is supplied through a resistor 398 to the base of a transistor 400, having an emitter resistor 402 connected to ground, and a collector resistor 404 connected to +5 volts. The base of the transistor 400 is connected to the slider of a biasing potentiometer 406, connected in series with a resistor 408 between +5 volts and ground.

In FIG. 17, a video switching transistor 410 is also provided, having its emitter connected to the emitter of the transistor 400. A resistor 412 is connected between the collector of the transistor 410 and a voltage source, such as +5 volts.

The base of the switching transistor 410 is connected to the signal line 256 extending from FIG. 16. It will be recalled that the line 256 is supplied with a timed pulse, derived from the monostable 246, and extending for the duration of the writing interval on the first storage tube 96. This pulse may have a duration of about six TV frames, for example. When the pulse is received, the switching transistor 410 is essentially nonconductive, while the transistor 400 is conductive. When the pulse is not received, the switching transistor 410 is conductive, so as to render the transistor 400 nonconductive. In this way, the video signals are switched off, so that they do not reach the input to the first storage tube 96.

The output from the transistor 400 is taken from the collector, which is connected directly to the base of a transistor 414 having an emitter potentiometer 416 connected between the emitter and ground. In this case, the collector is connected directly to the voltage source, such as +5 volts.

The potentiometer 416 acts as a variable gain control, having its slider connected through a resistor 418 to the base of a transistor 420. The emitter of the transistor 420 is connected through a resistor 422 to ground, while the collector is connected directly to a voltage source, such as +5 volts. The base of the transistor 420 is also connected through a variable resistor 424 and a fixed resistor 426 to the output line 270, which extends from FIG. 16. It will be recalled that the line 270 is supplied with a pulse derived from the monostable 246 and having a duration corresponding to the entire writing interval of the first storage tube 96, generally about six TV frames. The switching action afforded by this pulse allows video signals to appear on the cathode of the first storage tube 96 for the length of the pulse. In the absence of the pulse, the cathode of the storage tube 96 is at a resting "off" dc level.

The circuit of FIG. 17 preferably includes another switching transistor 428 having its emitter connected to a power source, such as +5 volts. In this case, the collector is connected through a potentiometer 430 to ground. The slider of the potentiometer is connected to the base of the transistor 420. The base of the transistor 428 is connected through a resistor 432 and a selector switch 434 to the control line 192 extending from FIG. 16. It will be recalled that the control line 192 is connected to the Q output of the JK flip-flop 186. It will be recalled that this output is supplied with a pulse during the use of every other filter. When the switch 434 is on, this pulse is transmitted to the base of the transistor 428, and then to the base of the transistor 420, where the pulse causes the cathode dc level on the first storage tube 96 to shift slightly on alternate filters. It has been found that this shifting produces improved images. When the switch 434 is off, the base of the transistor 428 is connected to ground through the resistor 432. Another resistor 438 is connected between the base and the emitter to afford a biasing action.

The output from the emitter of the transistor 420 is supplied to the base of an output transistor 440, preferably along a coaxial cable 442. A resistor 444 is connected between the emitter of the transistor 440 and ground. A load resistor 446 is connected in series with an inductor or coil 447 between the collector of the transistor 440 and a voltage source, such as +18 volts. The coil 447 may have any suitable inductance, such as 100 microhenries. The output of the transistor 440 is supplied from the collector to the first storage tube 96, and preferably is supplied to the cathode and the first grid. Thus, the collector may be connected to the input line 98 to the first storage tube 96 of FIG. 2.

Figure 18:
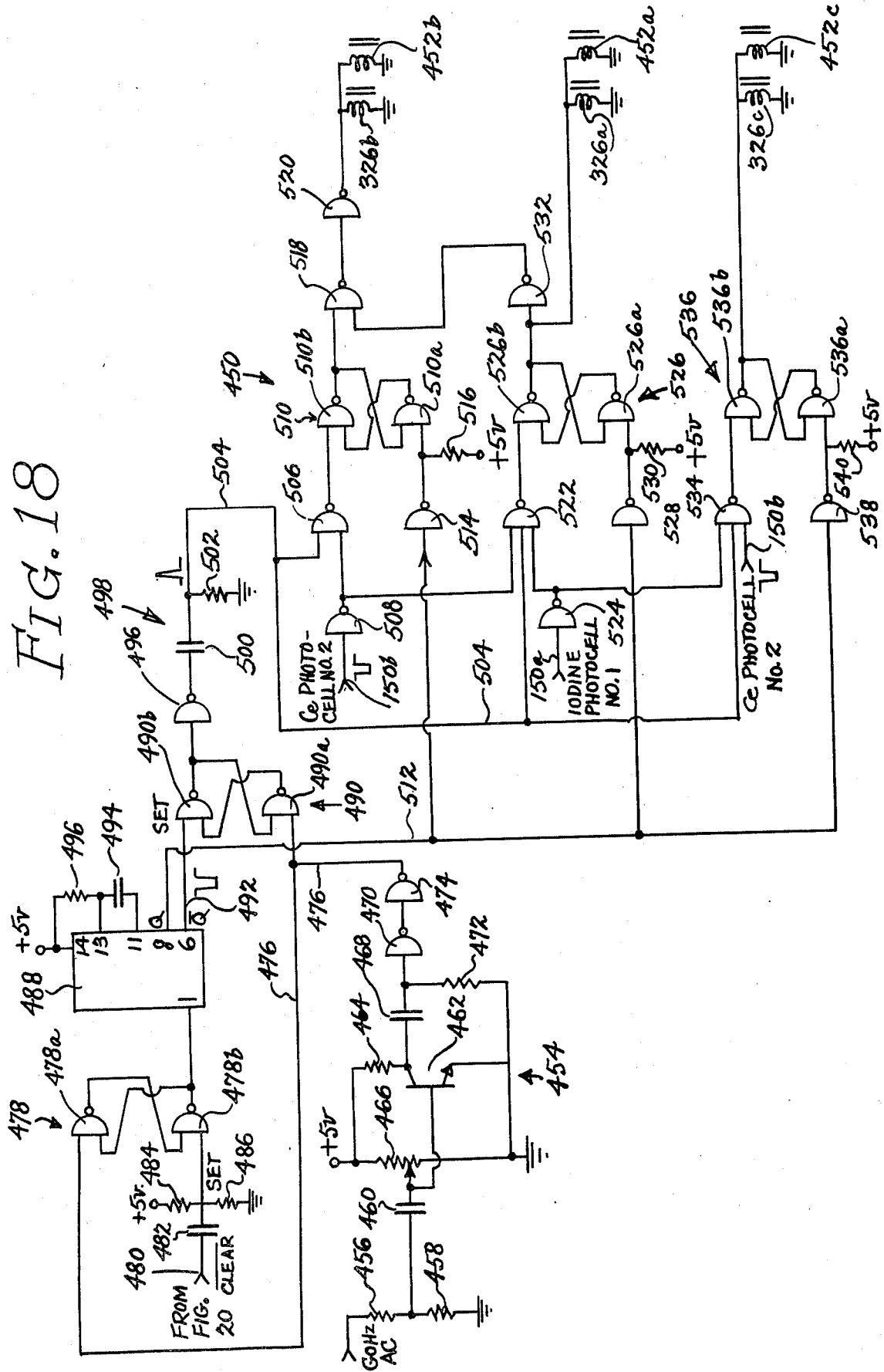
FIG. 18 is a schematic diagram showing logic circuits whereby the operation of the video storage tubes is coordinated with the rotation of the filter wheel in FIG. 1.

FIG. 18 illustrates the logic circuits which are operated by the signals from the photocells 88a and b, so as to bring about the switching of the high voltage supplied to the X-ray tube 16, the gain switching in the video amplifier circuits, as described in connection with FIG. 17, and also the switching of the electron current in the X-ray tube, if desired.

The signal lines 150a and b from the photocells 88a and b, described in connection with FIG. 16, also extend into FIG. 18. The signals from these lines are processed by a logic network 450, which analyzes the photocell signals to provide three separate output signals when the iodine, cerium and lead filters 24a, b and c are being used. These output signals are supplied to the relay coils 326a, b and c, described in connection with FIG. 17, for switching the gain of the video amplifier. The output signals may also be supplied to additional relay coils 452a, b and c, which may be employed to switch the high voltage supplied to the X-ray tube 14, and also the X-ray tube current, as will be described in greater detail in connection with FIG. 19. The relay coils 452a, b and c may be either in parallel with or in series with the coils 326a, b and c.

It is advantageous to carry out the high voltage switching operations at zero crossings of the alternating current power supply. To bring this about, the circuits of FIG. 18 include a zero crossing detector 454, which produces output pulses corresponding to positive-going zero crossings. The zero crossing detector 454 receives its input from the alternating current power supply by way of voltage dividing resistors 456 and 458. The junction between these resistors is connected through a coupling capacitor 460 to the base of a transistor 462 having its emitter grounded. A load resistor 464 is connected between the collector and a voltage source, such as +5 volts. The base is connected to the slider of a biasing potentiometer 466, connected between ground and a voltage source, such as +5 volts.

The output of the transistor 462 is taken from the collector, which is connected through a coupling capacitor 468 to the input of a NAND gate 470. A resistor 472 is connected between the input and ground, to provide a differentiating action. The output of the NAND gate 470 is supplied to the input of a second NAND gate 474 which delivers the zero crossing pulses at its output 476.

The circuits of FIG. 18 include means for coordinating the switching operations with the clear interval for the first storage tube 96. For this purpose, the circuits of FIG. 18 include an RS flip-flop 478 including cross-connected NAND gates 478a and b. The input of the gate 478b is supplied with an inverted clear pulse, extending for the duration of the clear cycle. This inverted clear pulse is derived from the circuits of FIG. 20 and is supplied to an input line 480. It will be seen that the line 480 is connected through a coupling capacitor 482 to the input of the gate 478b. To afford a biasing voltage for the input of the gate 478b, a resistor 484 is connected between the input and a voltage source, such as +5 volts. Another resistor 486 is connected between the input and ground.

The beginning of the inverted clear pulse sets the flip-flop 478, so that it will be responsive to the next zero crossing pulse, which is supplied to the input of the gate 478a over the line 476. The output of the gate 478b is supplied to the input of a monostable 488 which is fired when the flip-flop 478 is reset by the first zero crossing pulse. The monostable 488 supplies a timed output pulse to a second RS flip-flop 490, comprising cross-connected gates 490a and b. The Q output 492 of the monostable 488 is connected to the input of the gate 490b. The Q pulse at the output 492 sets the flip-flop 496, so that it is sensitive to the next zero crossing pulse, which is the second zero crossing pulse in the sequence. The zero crossing pulses are supplied to the input of the gate 490a over the line 476.

The monostable 488 may take the form of a commercially available integrated circuit, Type 74122. The duration of the pulse produced by the monostable is determined by a capacitor 494 and a resistor 496. The pulse may have a duration on the order of 12 milliseconds.

The output of the gate 490b is connected through a NAND gate 496 to a differentiating circuit, comprising a series capacitor 500 working into a shunt resistor 502. A sharp status pulse appears across the resistor 502. This status pulse is synchronized with the second zero crossing after the start of the clear for the first storage tube 96.

This status pulse is used to trigger the logic circuit 450.

It will be seen that the status pulse from the resistor 502 is supplied over a line 504 to one input of a NAND gate 506 having its other input supplied with the second photocell pulse by way of a NAND gate 508. The output line 150b from the second photocell is connected to the input of the gate 508, which has an inverting function.

The output of the gate 506 is supplied to one input of an RS flip-flop 510, comprising cross-connected NAND gates 510a and b. The output of the gate 506 goes to the input of the gate 510b. The input of the gate 510a is supplied with a reset signal which is derived from the Q output of the monostable 488. The Q output is supplied over a line 512 to the input of a NAND gate 514, having its output connected to the input of the gate 510a. A biasing voltage is supplied to the input of the gate 510a by a resistor 516 connected to a power source, such as +5 volts. The output of the gate 510b is connected to one input of a NAND gate 518 having its output connected to the input of a NAND gate 520. The relay coils 326b and 452b are connected to the output of the gate 520. These relay coils are energized when the cerium filter is moved into the X-ray beam.

The status pulse is also supplied over the line 504 to one input of a triple input NAND gate 522, having another input connected to the output of the NAND gate 508. Thus, the second photocell signal is received from the gate 508.

The first photocell signal is supplied to the circuits of FIG. 18 over the line 150a, which extends from FIG. 16. The line 150a is connected to the input of a NAND gate 524, having its output connected to the third input of the NAND gate 522.

The output of the triple input NAND gate 522 is connected to one input of another RS flip-flop 526, comprising cross-connected NAND gates 526a and b. The input of the gate 526b is connected to the output of the gate 522. The input of the gate 526a is supplied with a reset signal by a gate 528, having its input connected to the line 512 which carries the Q signal from the output of the monostable 488. A biasing voltage is supplied to the input of the gate 526a by a resistor 530, connected to a voltage source, such as +5 volts.

The output of the gate 526b is connected to the relay coils 326a and 452a, which are energized when the iodine filter is moved into the X-ray beam. In addition, the output of the gate 526 is supplied to the input of a gate 532 having its output connected to the second input of the gate 518.

The sharp status pulse is also supplied over the line 504 in FIG. 18 to one input of a triple input NAND gate 534, having another input connected to the output of the gate 524, whereby an inverted signal corresponding to the number one photocell signal is supplied to the gate 534. The number two photocell signal is supplied to the third input of the gate 534 over the line 150b, which extends from FIG. 16.

The output of the triple NAND gate 534 is connected to one input of another RS flip-flop 536, comprising cross-connected NAND gates 536a and b. The output of the gate 534 is connected to the input of the gate 536b. A reset pulse is supplied to the input of the gate 536a by a gate 538, having its input supplied with the Q output of the monostable 488, over the line 512. A biasing voltage for the input of the gate 536a is supplied by a resistor 540, connected to a voltage source, such as +5 volts.

It will be seen from FIG. 18 that the output of the gate 536b is connected to the relay coils 326c and 452c, which are operated when the lead filter is moved into the X-ray beam.

As previously indicated, the relay coils 326a, b and c also appear on FIG. 17 and are employed to switch the gain to an individual setting for each of the three X-ray spectra produced with the use of the iodine, cerium and lead filters.

Figure 19:
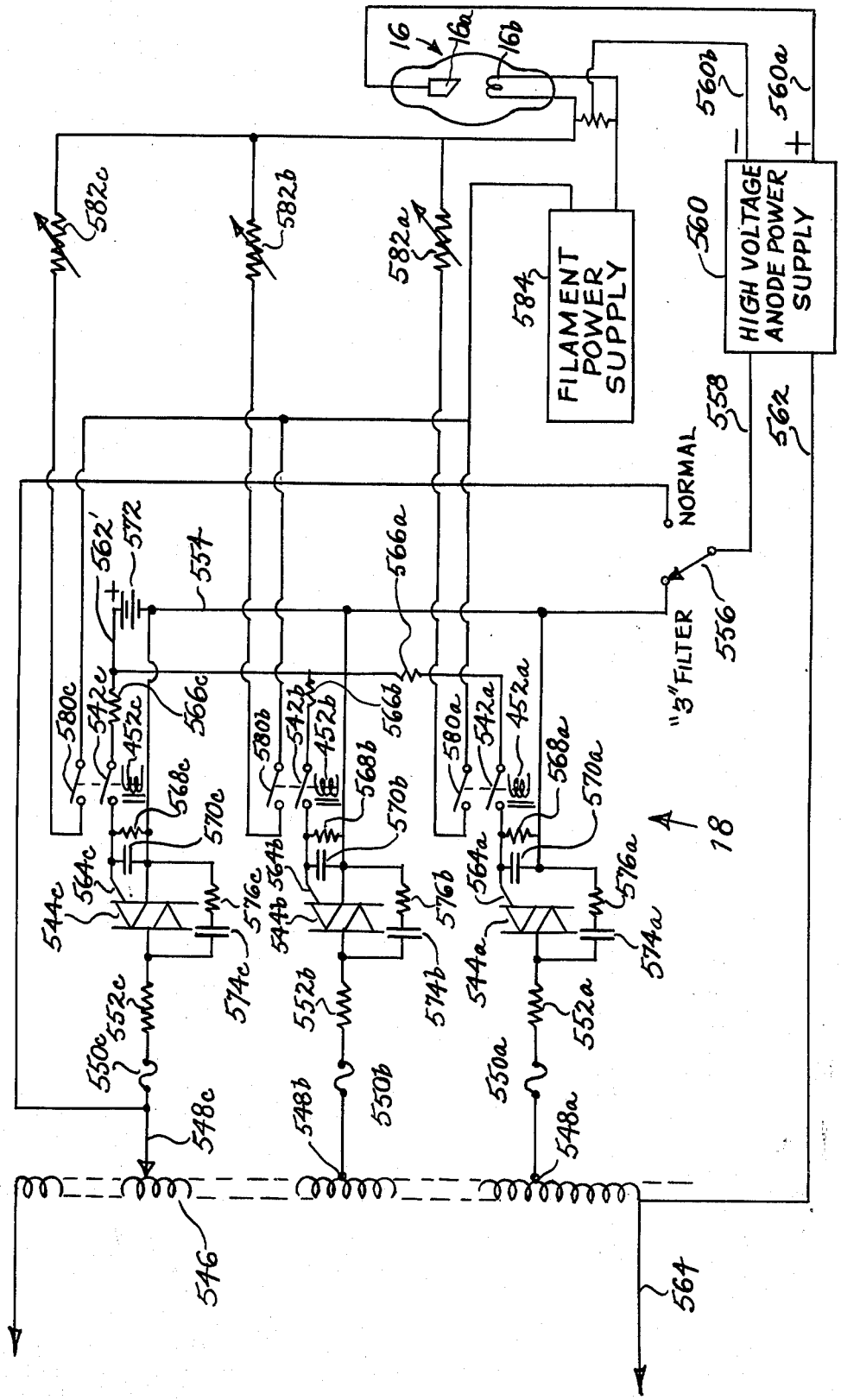
FIG. 19 is a schematic diagram showing control circuits for changing the anode voltage of the X-ray tube, and also the tube current, as the filters are changed.

The relay coils 452a, b and c also appear in FIG. 19 and are employed to switch to high voltage to the X-ray tube 14, so that a different high voltage can be employed to produce each of the three X-ray spectra. It will be seen that the relay coils 452a, b and c operate contacts or switches 542a, b and c. It is preferred to employ the contacts 542a, b and c to trigger electronic switching devices, such as the illustrated triacs 544a, b and c.

The triacs 544a, b and c receive alternating current power from an autotransformer winding 546 having three different taps 548a, b and c which are connected to the inputs of the triacs through individual fuses 550a, b and c and resistors 552a, b and c.

The outputs of the triacs 544a, b and c are connected to a common line 554 which goes through a changeover switch 556 to one input line 558 of a high voltage anode power supply 560. The other input line 562 goes to the return line 564 of the alternating current supply.

The high voltage anode power supply 560 has positive and negative high voltage output lines 560a and b which go to the anode and cathode 16a and b of the X-ray tube 16.

The changeover switch 556 has a three filter position in which the input line 558 is connected to the line 554 from the triacs 544a, b and c, and a normal position, in which the input line 558 is connected to the tap 548c. It will be understood that the taps 548a, b and c may be adjusted to provide the desired KVP to the X-ray tube to produce the three X-ray spectra.

The relay contacts 542a, b and c are connected into the triggering circuits for the triacs 544a, b and c. Thus, the contacts 542a, b and c are connected between a positive power supply lead 562' and the triggering electrodes 564a, b and c of the respective triacs 544a, b and c. Resistors 566a, b and c are connected in series with the contacts 542a, b and c. It will be seen that resistors 568a, b and c and capacitors 570a, b and c are connected between the triggering electrodes 564a, b and c and the outputs of the triacs 544a, b and c. The positive power supply lead 562 extends to a power supply 572 having its negative side connected to the output line 554 leading to the outputs of the triacs 544a, b and c.

It is preferred to connect capacitors 574a, b and c in series with resistors 576a, b and c between the inputs and the outputs of the triacs 544a, b and c.

The closure of the relay contact 542a causes the triac 544a to be conductive, so that the appropriate primary voltage is supplied to the high voltage power supply 560. Accordingly, the appropriate anode voltage is supplied to the X-ray tube 16.

FIG. 19 also illustrates circuits for switching the beam current in the X-ray tube 16 to three different values for the three different X-ray spectra. This can be done by changing the heating current through the filamentary cathode 16b. Changing the heating current changes the number of electrons emitted by the cathode, so that the beam current is changed accordingly.

The circuit of FIG. 19 comprises three additional relay contacts or switches 580a, b and c which may be operated by the relay coils 452a, b and c, or by separate relay coils, if desired. The contacts 580a, b and c are connected in series with individually variable resistors 582a, b and c. The relay contacts 580a, b and c and the resistors 582a, b and c form three alternative circuits which can be switched in series with the filament 16b of the X-ray tube. The current to heat the filament 16b is supplied by a filament power supply 584.

When the iodine filter is moved into the X-ray beam, the relay contacts 580a are closed. This connects the variable resistor 582a in series with the filament 16b. The resistor 582a is adjusted to provide the desired anode current in the X-ray tube 16 for the X-ray spectrum which is produced with the iodine filter.

Similarly, the variable resistors 582b and c are switched into the filament circuit for the X-ray spectra produced by the cerium and lead filters. The resistors 582b and c are adjusted to provide the desired anode currents for these X-ray spectra.

FIG. 20 illustrates the circuits for controlling the operation of the first storage tube 96. These circuits control the operating voltage of the anode or backplate 110. During the clear mode, the anode voltage is switched to a relatively high value from 100 to 340 volts, for example. During the write mode, the anode voltage is switched to a relatively low value, such as 1 to 30 volts. The sequence of operations is illustrated in FIG. 5.

In FIG. 2, as previously described, the control line 54a leads to the anode or backplate 110. This control line also appears in FIG. 20.

The write voltage of about 1 to 30 volts is applied to the control line 54a whenever the clear voltage is not applied. As shown in FIG. 20, the write voltage is derived from a potentiometer 590 connected between ground and a voltage source, such as +30 volts. The slider of the potentiometer 590 is connected to the control line 54a through a diode rectifier 592. The potentiometer 590 is adjusted to the desired write voltage, from 1 to 30 volts, for example. The voltage from the potentiometer is applied to the line 54a by the diode 592, except when a higher voltage is applied to the line 54a during the clear mode, in which case the diode 592 becomes non-conductive and thus acts as a gate.

The higher clear mode voltage is derived from a voltage divider, comprising a resistor 594, a potentiometer 596, and another resistor 598, connected in series between a voltage source, such as +350 volts and ground. As shown, the slider of the potentiometer 596 is connected to the base of a transistor 600 having its collector connected to the junction 602 between the resistor 594 and the potentiometer 596. A resistor 604 is connected between the emitter of the transistor 600 and ground. It will be seen that the emitter is connected through a resistor 606 and a diode rectifier 608 to a line 610, which is connected to the control line 54a by a resistor 612. A resistor 613 is connected between the line 610 and ground.

The transistor 600 acts as an emitter follower, so that the output voltage on the emitter follows the input voltage on the base. Thus, the clear mode voltage can be adjusted by moving the slider of the potentiometer 596.

Another transistor 614 is provided to switch the clear voltage on and off. The emitter of the transistor 614 is connected to ground, while the collector is connected to the junction 616 between the resistor 606 and the diode 608. When the transistor 614 is conductive, it effectively short circuits the clear mode voltage.

A bias voltage for the base of the transistor 614 is derived by connecting a resistor 618 between the base and a voltage source, such as +20 volts.

A negative clear pulse, extending for the length of the clear mode, is generated by a clear pulse circuit 620 and is supplied to the base of the transistor 614 over a clear gate line 622, which is connected to the base through a resistor 624 in parallel with a capacitor 626.

The clear pulse circuit 620 generates the clear pulse, which generally extends for one TV frame. However, it can be longer, if desired. The clear pulse circuit 620 is triggered by a pulse derived from the circuits of FIG. 16, over the control line 200, which appears in both FIG. 16 and FIG. 20. The trigger pulse is derived from the monostable 170 and is relatively brief, considerably less than one TV frame.

In the clear pulse circuit 620 of FIG. 20, the pulse from the line 200 is employed to trip a flip-flop 630, comprising cross-connected NOR gates, 630a and 630b. The input line 200 is connected to the input of the gate 630a through a coupling capacitor 632. The input is also connected to a bias source, such as −4 volts, through a resistor 634.

The output of the gate 630a is connected to the enable inputs of two counters 636 and 638, which may take the form of a commercially available integrated circuit, Type MC790P.

The input of the first counter 636 is supplied with vertical drive pulses, arriving over a signal line 640 from the TV sync and sweep generator 64 of FIG. 1. The line 640 is connected to the input of the counter 636 through a resistor 642. The input of the counter 636 is also connected to a bias source, such as −4 volts, through a resistor 644.

The output of the counter 636 is connected to the input of the counter 638, while the output of the counter 638 is supplied to a signal line 646, from which a coupling capacitor 648 is connected back to the input of the gate 630b in the flip-flop 630. The input of the gate 630b is also connected to a bias source, such as −4 volts, by a resistor 650.

After the flip-flop 630 has been tripped by the clear trigger pulse from the line 200, the counters 636 and 638 are enabled, whereupon the counter 636 is triggered by the next vertical blanking pulse from the line 640. The counter 638 is triggered in synchronism with the second blanking pulse and is retriggered in synchronism with the fourth blanking pulse. Thus, the counter 638 produces an output pulse corresponding in length to one TV frame. This pulse is used to time the clear mode. At the end of this clear pulse, the flip-flop 630 is reset to its original state, with the result that the counters 636 and 638 are disabled.

The clear pulse is supplied over the line 646 to one input of a NOR gate 654 having its other inputs connected to a voltage source, such as −4 volts. A resistor 656 is preferably connected between the line 646 and ground. The output of the gate 654 is fed into an amplifier 658 which in turn feeds its output into a second amplifier 660. These amplifiers may take the form of commerically available integrated circuits, Type MC788P. The output of the amplifier 660 is connected to the line 622, extending to the transistor 614 which switches the backplate 110 of the first storage tube 96 between its write voltage, of 1 to 30 volts, and its clear voltage, of 100 to 340 volts.

In this case, a diode 662 is connected between the line 622 and ground, to prevent any substantial positive voltage from developing on the line 622. A second diode 664 is reversely connected between the line 622 and a negative voltage source, such as −4 volts. The diode 664 limits the negative voltage on the line 622 to approximately −4 volts. Thus, the clear pulse on the line 622 is in the form of a pulse going from zero to −4 volts. This pulse is sufficient to render the transistor 614 nonconductive so that the clear mode anode voltage of 100 to 340 volts is applied to the line 610, and then through the resistor 612 to the line 54a, extending to the anode or backplate 110 of the first storage tube 96. In the absence of this clear pulse, the transistor 614 is conductive, so that the high voltage of 100 to 340 volts is substantially short circuited by the transistor 614.

In the circuits of FIG. 20, the clear pulse from the line 622 is supplied to one input of a NOR gate 668 having its other input connected to a voltage source, such as −4 volts. The output of the NOR gate 668 is supplied to one input of another NOR gate 670 having its other input connected to −4 volts. The output of the NOR gate 670 goes to the input of an amplifier 672 having its output connected to the input of another amplifier 674. The amplifier 672 and 674 may take the form of a commercially available integrated circuit, Type MC788P.

The output of the amplifier 674 may be connected to one input of a NOR gate 676 having its other input connected to a voltage source, such as −4 volts. The output of the NOR gate 676 is employed to operate another switching transistor 678 having its collector connected to the line 610. The emitter of the transistor 678 is grounded. Thus, when the transistor 678 is conductive, the line 610 is grounded so that any voltage thereon is effectively short circuited. The base of the transistor 678 is connected through a resistor 680 to a voltage source, such as +20 volts. Thus, in the absence of an input signal, the transistor 678 is conductive so that the line 610 is effectively grounded. In this state, the only voltage that can get to the line 54a is the write voltage of about 1 to 30 volts, which is protected from being grounded by the resistor 612.

The output of the NOR gate 676 is connected to a line 682 which is connected to the base of the transistor 678 by a resistor 684 in parallel with a capacitor 686. A diode 688 is connected between the line 682 and ground. This diode prevents any substantial positive voltage from appearing on the line 682. Another diode 690 is reversely connected between the line 682 and a negative voltage source, such as −4 volts. Thus, the negative voltage on the line 682 is limited to about 4 volts.

The negative clear pulse of about −4 volts on the line 682 renders the transistor 678 nonconductive during the clear mode, so that the high anode voltage of about 100 to 340 volts can be supplied to the backplate 110 of the first storage tube 96.

It will be seen that the signal line 212 is connected to the output of the gate 688. This signal line 212 extends to the circuits of FIG. 16 and is employed to trigger the monostable 214 at the end of the clear pulse. The clear pulse on the line 212 is inverted with respect to the clear pulse on the line 622.

The signal line 480, extending to the circuits of FIG. 17, may be connected to the line 646. It will be recalled that the inverted clear pulse on the line 480 sets the flip-flop 478 in the circuits for determining the status of the filter wheel 24.

Figure 21:
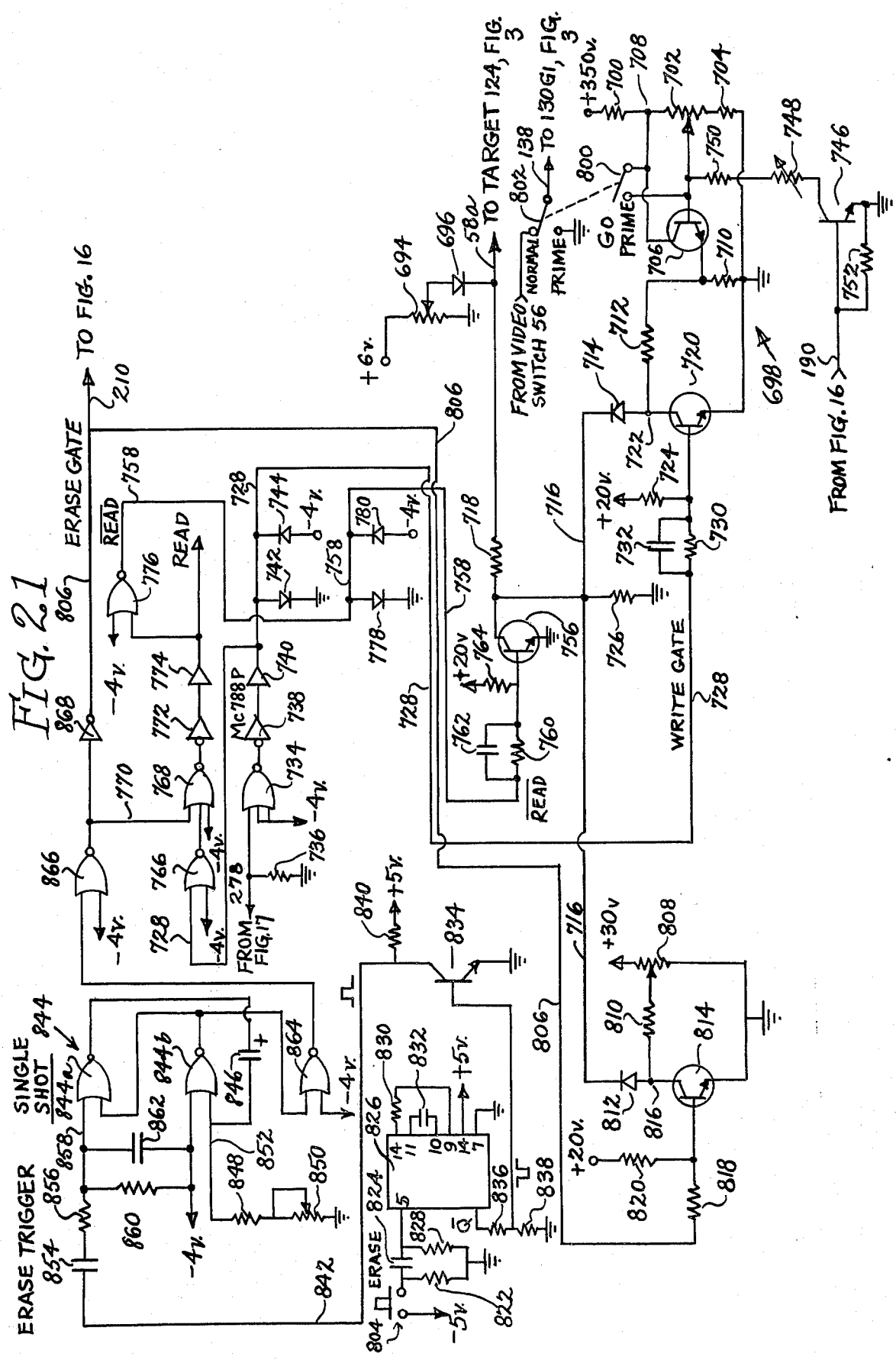
FIG. 21 is a schematic diagram showing control circuits for the second storage tube.

FIG. 21 illustrates the circuits for controlling the operation of the second storage tube 120. The circuits of FIG. 21 are adapted to supply the anode or target voltages to the second storage tube 120 for the modes designated read, positive write, negative write, erase and prime.

As shown in FIG. 3, the line 58a is adapted to supply the operating voltage to the target or anode backplate 124. This line 58a also appears in FIG. 21.

In the circuits of FIG. 21, the read voltage of about 6 volts is supplied by a potentiometer 694, connected between a voltage source, such as +6 volts, and ground. The slider of the potentiometer 694 is connected through a diode 696 to the line 58a which extends to the target 124 of the second storage tube 120 in FIG. 3. The diode 696 effectively disconnects the read voltage if the voltage on the line 58a exceeds the read voltage.

The positive and negative write voltages are produced by a circuit 698 and are derived from a voltage source, such as +350 volts, through a voltage divider, comprising a resistor 700, a potentiometer 702, and a resistor 704, connected between +350 volts and ground. The slider of the potentiometer 702 is connected to the base of a transistor 706 having its collector connected to the junction 708 between the resistor 700 and the potentiometer 702. A resistor 710 is connected between the emitter and ground. The emitter of the transistor 706 is also connected to the line 58a through a resistor 712, a diode 714, a line 716, and another resistor 718. The voltage on the emitter corresponds to that on the base, and thus is determined by the setting of the potentiometer 702. For example, the potentiometer 702 may be set to provide about +50 volts for the positive write mode.

This voltage is adapted to be switched on and off by a switching transistor 720 having its emitter grounded. Its collector is connected to the junction 722 between the resistor 712 and the diode 714. A biasing voltage to render the transistor 720 conductive is supplied to the base of the transistor by a resistor 724 connected to a voltage source, such as +20 volts. When the transistor 720 is conductive, it effectively short circuits the voltage at the collector of the transistor 706.

In this case, a resistor 726 is connected between the line 716 and ground.

A write gate line 728 is connected to the base of the transistor 720 by a resistor 730 in parallel with a capacitor 732.

The application of the write gate pulse to the line 728 is controlled by the write pulses received over the line 278 from FIG. 17. In FIG. 21, the line 278 is connected to one input of a NOR gate 734 having its outer inputs connected to a voltage source, such as −4 volts. A resistor 736 may be connected from the line 278 to ground.

The output of the NOR gate 734 is connected to the input of an amplifier 738 having its output connected to the input of a second amplifier 740. The output of the amplifier 740 is connected to the write gate line 728.

It will be seen that a diode 742 is connected between the line 728 and ground. A reversely connected diode 744 is preferably connected between the line 728 and a voltage source, such as −4 volts. Thus, the write gate pulse appears on the line 728 as a pulse ranging from approximately zero to approximately −4 volts. When this write gate pulse appears, it causes the transistor 720 to be nonconductive, so that the write voltage is supplied to the line 716, and through the resistor 718 to the target line 58a.

The circuit 698 is switched between the positive write voltage of about 50 volts and the negative write voltage of about 10 volts by a transistor 746 which serves as the negative write gate. The emitter of the transistor 746 is grounded, while the collector is connected to the base of the transistor 706 by a variable resistor 748 in series with a fixed resistor 750. When the transistor 746 is conductive, the series combination of the resistors 748 and 750 is shunted between the base of the transistor 706 and ground, so that the base voltage is reduced to the negative write voltage. The variable resistor 748 is employed to adjust the negative write voltage.

The signals to control the switching transistor 746 are supplied from the circuits of FIG. 16 by the line 190, which extends from the Q output of the JK flip-flop 186 and is connected to the base of the transistor 746 in FIG. 21. In this case, a resistor 752 is connected between the base and ground.

The JK flip-flop 186 in FIG. 16 produces a pulse on the line 190 when every other filter is moved into the X-ray beam. Thus, alternate filters cause the transistor 746 to become conductive so that the negative write voltage is produced. When the transistor 746 is nonconductive, the positive write voltage is produced.

In the circuits of FIG. 21, a read gate switching transistor 756 has its collector connected to the line 716, while its emitter is grounded. When the transistor 756 is conductive, it effectively short circuits the line 716 to ground, so that no voltage can get from the line 716 to the line 58a which extends to the target 124 of the second storage tube 120. An inverted read pulse is supplied to the base of the transistor 756 by an inverted read gate line 758, connected to the base by a resistor 760 in parallel with a capacitor 762. A biasing voltage is supplied to the base by a resistor 764 connected to a voltage source, such as +20 volts. Thus, the transistor 756 is conductive unless a negative pulse is supplied to the base of the transistor 756.

An inverted read pulse is supplied to the line 758 whenever the second storage tube is not in a write, erase or prime mode. This is done by a logic chain beginning with a NOR gate 766 having one input connected to the write gate line 728. The other input of the gate 726 is connected to a voltage source, such as −4 volts. The output of the NOR gate 766 is connected to one input of a triple input NOR gate 768 having its second input connected to a voltage source, such as −4 volts. The third input of the gate 768 is connected to the erase gate chain by a line 770, as will be described in greater detail presently.

The output of the gate 768 is connected to the input of an amplifier 772, having its output connected to the input of a second amplifier 774. The amplifiers 772 and 774 may take the form of a commercially available integrated circuit, Type MC788P.

In this case, the output of the amplifier 774 is connected to one input of a NOR gate 776, which is employed to provide an inverted signal. The other input of the NOR gate 776 is connected to a voltage source, such as −4 volts. The inverted read pulse appears at the output of the gate 776, which is connected to the line 758.

As before, a diode 778 is connected between the line 758 and ground, to prevent the appearance of any substantial positive voltage on the line 758. A diode 780 is preferably connected between the line 758 and a voltage source, such as −4 volts, to limit the negative signal voltage on the line to approximately 4 volts.

A negative signal voltage appears on the line 758 whenever the second storage tube 120 is in the write, prime or erase mode. This negative voltage renders the transistor 756 nonconductive. When this negative signal voltage does not appear, the transistor 756 is conductive, so that the line 716 is effectively short circuited to ground. In this condition, only the read voltage can get to the line 58a.

The remainder of the circuits in FIG. 21 are employed to operate the second storage 120 in the prime and erase modes. The tube is switched manually into these modes, in preparation of normal operation.

As previously mentioned, FIG. 16 shows three start-stop switched 174a, b and c. When the second storage tube 120 is to be switched into the prime mode, these three switches should be in the closed or stop position.

In FIG. 16, the switch 276 is a preparatory switch which should be moved to its continuous write position in preparation for the prime mode. In this position, the line 278 is connected to −4 volts, which is thereby supplied to the input of the NOR gate 734 in FIG. 21, so that the second storage tube 120 is switched to the write mode. The switching transistor 720 is thereby rendered nonconductive, so that the voltage from the emitter of the transistor 706 is supplied to the target 124 of the storage tube 120.

FIG. 21 shows a second preparatory switch 800 which is connected between the emitter and the base of the transistor 706. When the second storage tube 120 is to be switched into the prime mode, the switch 800 is closed. This switch short circuits a portion of the potentiometer 702, so as to raise the voltage on the base of the transistor 706. The voltage supplied to the target 124 of the second storage tube 120 is correspondingly raised to about 140 volts, for example.

FIG. 21 shows a third preparatory switch 802 which is connected to the first grid 130G1 of the second storage tube 120 in FIG. 3. Normally, the switch 802 connects the first grid 130G1 to the output of the video switch 56. For the prime mode, the switch 802 is moved to its prime position, in which the first grid 130G1 is connected to ground. In the prime mode, the target 124 of the second storage tube 120 is operated at a high voltage, such as +140 volts, while the electron beam is operated without modulation. The effect is to spray electrons uniformly over the target mosaic 126. As just indicated, the prime mode is initiated manually and is continued for a short time, such as two or three seconds, at the discretion of the operator. The prime mode is then terminated by opening the switch 800, moving the switch 802 to its normal position, and moving the switch 276 to its automatic position. These operations cause the second storage tube to go to its read mode.

The second storage tube 120 is then usually switched to the erase mode for a brief interval. This may be done either automatically or manually.

The circuits of FIG. 21 are arranged for manual switching to initiate the erase mode. For this purpose, a push-button erase switch 804 is provided. Operating this erase switch 804 causes the second tube to go into the erase mode for a brief timed interval, such as several TV frames.

The closure of the erase switch 804 causes an erase gate pulse to appear on an erase gate line 806. This pulse causes an erase voltage to be applied to the target 124 of the second storage tube 120. The erase voltage may be about +20 volts, for example. As shown in FIG. 21, the erase voltage is derived from a potentiometer 808 connected between ground and a voltage source, such as +30 volts. The slider of the potentiometer 808 is connected through a resistor 810 and a diode 812 to the line 716, which extends through the resistor 718 to the target line 58a.

A switching transistor 814 is provided to switch the erase voltage on and off. It will be seen from FIG. 21 that the collector of the transistor 814 is connected to the junction 816 between the resistor 810 and the diode 812. The emitter of the transistor 814 is grounded. When the transistor 814 is conductive, the erase voltage is effectively short circuited so that it can not get through the diode 812 to the line 716.

The erase gate line 806 is connected to the base of the transistor 814 through a resistor 818. A biasing voltage is supplied to the base by a resistor 820, connected to a voltage source, such as +20 volts. In the absence of a negative pulse on the erase gate line 806, the biasing voltage causes the transistor 814 to be conductive, so that the erase voltage is not supplied to the target 124 of the second storage tube 120.

The circuits will now be described whereby the closure of the push-button switch 804 produces the erase gate pulse on the line 806. It will be seen from FIG. 21 that the erase switch 804 is connected in series with a resistor 822 between a voltage source, such as +5 volts, and ground. A coupling capacitor 824 is connected between the input of a monostable 826 and the junction between the switch 804 and the resistor 822. Thus, the closure of the switch 804 supplies a +5 volt pulse to the input of the monostable 826. A resistor 828 is connected between the input and ground.

The monostable 826 produces a timed pulse, the duration of which is determined by a resistor 830 and a capacitor 832. This pulse is relatively brief, generally less than one TV frame.

The monostable 826 may take the form of a commercially available integrated circuit, Type 74121. The $\overline{Q}$ output of the monostable 826 may be connected to the base of a transistor 834 through a resistor 836. Another resistor 838 is preferably connected between the base and ground. In this case, the emitter of the transistor 834 is grounded, while the collector is connected to a voltage source, such as +5 volts, through a resistor 840. The negative-going monostable output pulse is converted into a positive-going output pulse at the collector of the transistor 834.

This pulse is transmitted over an erase trigger line 842, which extends to the input of erase trigger circuits, beginning with a single shot 844, comprising NOR gates 844a and b. The output of the gate 844b is cross-connected to one input of the gate 844a. A timing capacitor 846 is connected between the output of the gate 844a and one input of the gate 844b. The other input is connected to a voltage source, such as −4 volts. The duration of the pulses produced by the single shot 844 is determined by the capacitor 846, in conjunction with a fixed resistor 848 connected in series with a variable resistor 850, connected between ground and the same input 852 of the gate 844b, to which the capacitor 846 is connected.

The erase trigger line 842 is connected through a coupling capacitor 854 and a resistor 856 to the second input 858 of the gate 844a. As shown, a biasing voltage is supplied to the input 858 by a resistor 860 connected to a voltage source, such as −4 volts. In this case, a capacitor 862 is connected in parallel with the resistor 860.

The brief trigger pulse received over the line 842 causes the single shot 844 to produce an erase control pulse of longer duration, corresponding to the duration of the erase mode, which may extend for one or more TV frames.

In this case, the output of the gate 844b is connected to one input of a NOR gate 864, having its other input connected to a voltage source, such as −4 volts. The output of the gate 864 is connected to one input of another NOR gate 866, having its other input connected to a voltage source, such as −4 volts.

The output of the gate 866 is connected to the line 770, extending to one of the inputs of the triple NOR gate 768. The effect of this connection is to prevent the second storage tube 120 from going into a read mode when the erase gate pulse is generated.

The output of the gate 866 is also connected to the input of an amplifier 868, having its output connected to the erase gate line 806. The amplifier 868 may take the form of a commercially available integrated circuit, Type MC799P.

For the duration of the erase mode, as determined by the single shot 844, the erase gate pulse appears on the line 806 and renders the transistor 814 nonconductive, so that the erase target voltage is supplied through the diode 812 to the line 716, and then through the resistor 718 to the line 58a, extending to the target 124 in FIG. 3.

During the erase mode, the electron beam in the second storage tube 120 writes negatively with no video modulation, so that any residual image from prior operations is wiped out.

Preferably, the control line 210 extends from the erase gate line 806 in FIG. 21 to the circuits of FIG. 16. It will be recalled that the line 210 is coupled to one input of the gate 196. Thus, the erase gate signal is effective to produce a clear trigger pulse on the line 200, which triggers the first storage tube 96 to the clear state, as previously explained.

The erase operation automatically terminates itself by the timing out of the single shot 844, which terminates the erase gate pulse. The first storage tube 96 returns to the write mode, while the second storage tube 120 returns to the read mode. Thus, the circuits are ready for normal operation.

While the operation of the X-ray apparatus 10 will be clear from the forgoing description, it may be helpful to summarize the operation. Prior to commencement of normal operation, the start-stop switches a, b and c are in their stop or closed positions. The closure of these switches prevents the first and second storage tubes 96 and 120 from developing images. The first storage tube 96 is in a passive state, with the low write voltage of 1 to 30 volts on its backplate 110. No video modulation is applied to the first storage tube 96 at this time. The second storage tube 120 is in a passive read mode, with the low read voltage of about 6 volts on its backplate 124.

As previously described, the second storage tube 120 is normally primed and erased prior to normal operation. The tube is switched to the prime mode by operating the three ganged preparatory switches. The switch 276 in FIG. 16 is moved to its continuous write position, so as to switch the second storage tube 120 to the continuous write mode. In FIG. 21, the switch 802 is simultaneously moved to its prime position, so as to remove any video modulation from the second storage tube 120 by grounding the first grid 130G1. Simultaneously, the switch 800 is closed so as to raise the backplate voltage on the second tube 120 to a higher value, such as 140 volts, for example, for the prime mode. In the prime mode, the electron beam sprays electrons uniformly over the target mosaic 126 of the second storage tube 120. Due to the high target voltage, the secondary electron emission is greater than the primary electron beam current, so that the target mosaic 126 is driven in a positive direction to some extent during the prime mode. Generally, the prime mode may be timed manually so that it will last a few seconds. The prime mode is terminated by moving the switch 276 to its automatic position, while moving the switch 802 to its normal position, in addition to opening the switch 800. These operations return the second storage tube 120 to its passive read mode.

The erase mode is triggered by closing the push-button switch 804 in FIG. 21, through the electric circuits involved. This switches the target voltage on the second storage tube 120 to the erase value of about 20 volts, so that the electron beam will write uniformly and in a negative sense on the target mosaic 126. As a result, any residual image is wiped out. The erase mode is timed electronically by the one shot circuit 844 of FIG. 21. The duration of the erase mode may be a few seconds.

Normal operation is started by energizing the motor 26 in FIG. 1, so as to rotate the filter wheel 24, and by opening the three start-stop switches 174a, b and c. When the iodine filter moves into the X-ray beam, the signals from the photocells 88 a and b reset the flip-flop 154 so that it triggers the monostable 170. The brief pulse produced by the monostable 170 triggers the JK flip-flop 186, which thereafter keeps track of the movement of the filter wheel 24. The JK flip-flop 176 produces output signals for alternate filters 24a–d for use in triggering the second storage tube 120 between its two write modes, in which it writes in either a negative or a positive sense. During the use of the iodine and lead filters, the second storage tube 120 may be caused to write in a positive sense. During the use of the cerium filters 24 b and d, the second storage tube 120 may be caused to write in a negative sense. The JK flip-flop 186 triggers the switching transistor 746 in FIG. 21.

The pulse from the monostable 170 also triggers the circuits in FIG. 20 so as to initiate the first clear mode interval in the first storage tube 96. This begins the sequence shown in FIG. 6. The clear mode generally lasts for one TV frame, as timed by the counters 636 and 638. During the clear, the voltage on the target 110 is raised to a higher value, such as about 100 volts. The electron beam is operated without modulation, so that it sprays electrons uniformly over the front surface of the dielectric layer 112. Due to secondary electron emission, which exceeds the primary electron beam current, the voltage on the dielectric layer is driven slightly in a positive direction during the clear operation.

Figure 6:
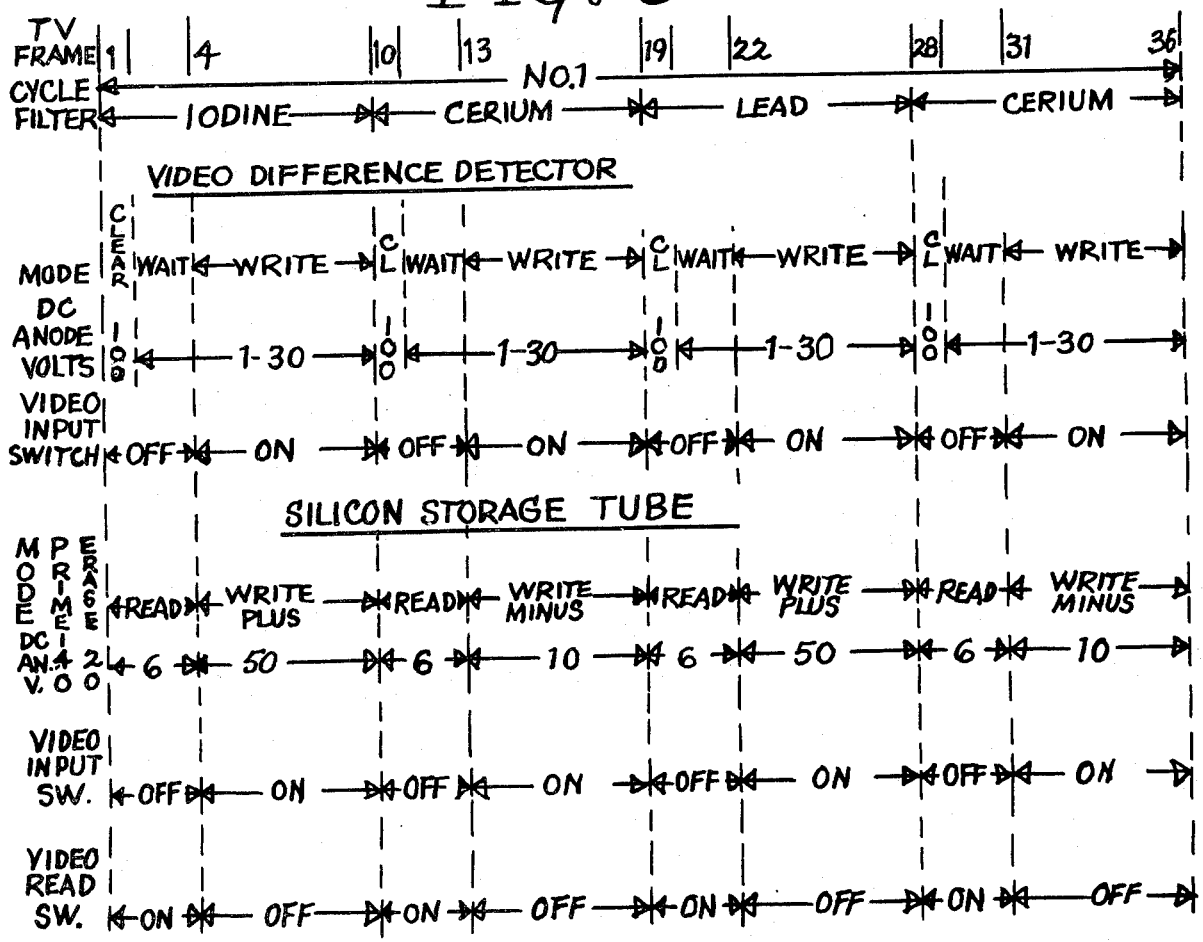
FIG. 6 is a timing diagram to illustrate the operation of the first and second storage tubes in the system of FIG. 1.

The clear pulse from FIG. 20 is applied to the monostable 214 and is effective to trigger the monostable at the end of the clear pulse. The monostable 214 introduces a brief delay or waiting interval generally amounting to two or more TV frames. Two frames are indicated in FIG. 6, but the delay may often be made greater, to allow time for the high voltage on the X-ray tube 14 to stabilize. This delay also allows the TV camera 46 to stabilize as it adjusts to the new X-ray image.

After the monostable 214 of FIG. 16 times out, it sets the flip-flop 228. The next vertical blanking pulse resets the flip-flop, which thereupon triggers the monostable 246.

It will be recalled that the monostable 246 produces the write gate pulse which extends for the duration of the write mode on the first and second storage tubes 96 and 120. A suitable write interval is about six TV frames, for example. This interval is indicated in FIG. 6.

During the write mode, the first storage tube 96 is operated at a low target voltage of 1 to 30 volts, for example. The X-ray image produced with the iodine filter 24a is written on the dielectric layer 112 in the first storage tube 96 during this write interval.

During the write mode on the first storage tube 96, the second storage tube 120 is also switched to the write mode. For the iodine filter, the second storage tube 190 may be operated in the positive write mode, with a target voltage of about 50 volts, for example. The video output signals from the first storage tube 96 are employed to modulate the second storage tube 120.

The write mode is terminated by the end of the timing pulse produced by the monostable 246. The second storage tube 120 goes to the read mode, in which the low read voltage, of about 6 volts, for example, is applied to the target 124 of the second storage tube.

Another cycle is initiated when the cerium filter moves into the X-ray beam. The photocells 88a and b then produce signals which trigger a clear mode for the first storage tube 96. This clear mode is triggered in the same manner as in the first cycle. The X-ray apparatus 10 goes through the same cycle as just described for each of the four filters 24a–d. As long as operation is continued, the apparatus will continue going through the same cycle for each filter.

The circuits of FIGS. 18 and 19 are operated in response to the movement of the filters 24a–d into the X-ray beam. The signals from the photocells 88a and b control these circuits so that the anode voltage or KVP on the X-ray tube 16 is switched to a different value for each of the three different filters. Thus, for example, the anode voltage may be switched to 45 KVP for the iodine filter 24a, 60 KVP for each of the cerium filters 24b and d, and 70 KVP for the lead filter 24c. These voltage changes are brought about by the relays 452a, b and c, which trigger the triacs 544a, b and c. The relays may be in the form of reed relays, for example. The relays 452a–c are operated by the logic circuits of FIG. 18, in response to the signals from the photocells 88a and b.

The circuits of FIG. 19 may also be employed to change the beam current in the X-ray tube 16, so as to change the intensity of the X-rays, as the different filters are moved into the X-ray beam. The beam current is changed by changing the heating current in the filament 16b, which changes the electron emission.

The circuits of FIG. 17 are employed to change the gain in the video amplifier for the first storage tube 96, as the filters are changed. The relays 326a, b and c are employed to do the gain switching. These relays are controlled by the logic circuits of FIG. 18.

The video amplifier circuits of FIG. 17 feature logarithmic amplification by the logarithmic amplifier 334. Logarithmic amplification is highly advantageous, because the exponential contributions to the video images due to soft tissue and bone are thereby rendered linear, so that the image elements due to soft tissue and bone can be largely cancelled out by subtracting the average of the first and third images from the second image, as represented by the graphs of FIGS. 14 and 15. Logarithmic amplification has the further advantage that difference images representing a small percentage of the unsubtracted video images will have a magnitude independent of the overall scale factor or gray shade of the unsubtracted video images.

As the four X-ray spectra are successively produced by moving the four X-ray filters 24a–d successively into the X-ray beam, the resulting X-ray images are written on the dielectric screen 112 of the first storage tube 96. During the writing of each image, the storage tube 96 moves toward equilibrium as the electrostatic image builds up on the dielectric screen 112. The clear mode shifts the entire image on the dielectric screen 112 in a positive direction by a small amount, such as about 1 volt, for example.

Figure 10:
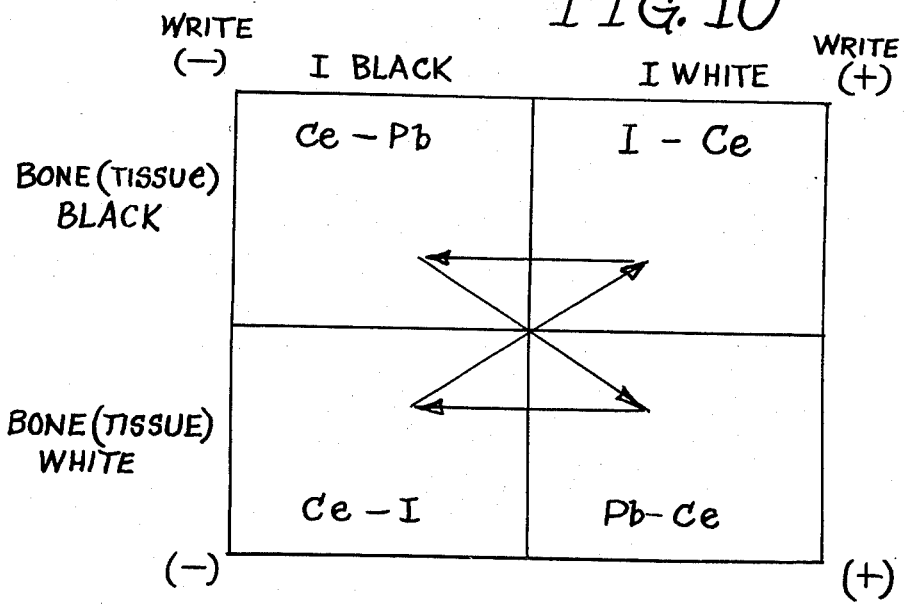
FIG. 10 is a diagram illustrating the manner in which the four X-ray images are combined by the first and second storage tubes.

During the writing of the second and subsequent images on the first storage tube 96, the tube makes a subtractive comparison between the new image and the previously written images. Thus, the video output from the first storage tube 96 is in the form of four difference images, representing the differences between the images in the successive pairs of images written on the first storage tube. This series of operations is illustrated in the diagram of FIG. 10, in which the four difference images are indicated as iodine minus cerium, cerium minus lead, lead minus cerium and cerium minus iodine. The directional arrows represent this sequence of the four difference images.

The four difference images are written and integrated on the target mosaic 126 of the second storage tube 120. The alternate difference images are written in a negative sense and in a positive sense so that the image elements due to the contrast medium, iodine in this case, are enhanced, while the image elements due to soft tissue and bone are largely cancelled out. The image elements due to the contrast medium receive a contribution from each of the four difference images, and thus are multiplied by four. On the other hand, the image elements due to soft tissue and bone are combined subtractively so that the net contribution is close to zero.

The four difference images are arranged in a matrix in FIG. 10, in accordance with whether the image elements for iodine, bone and soft tissue are written black or white. Thus, if the difference image I minus Ce is displayed, the contrast medium, iodine, appears white, while the bone and soft tissue appear black. In the difference image Ce minus Pb, the contrast medium appears black, while the bone and soft tissue appear black. In the difference image Pb minus Ce, the contrast medium, iodine, appears white, while bone and soft tissue also appear white. In the difference image Ce minus I, the contrast medium appears black, while soft tissue and bone appear white.

By writing the four difference images on the second storage tube 120 alternately in a positive and a negative sense, the image components due to the contrast medium can be written in the same direction for all four difference images, while the components for soft tissue and bone are alternately written in opposite directions and thus are largely cancelled out.

As indicated in the diagram of FIG. 10, the two difference images, I minus Ce and Pb minus Ce, in which the iodine appears white, may be written in a positive sense, indicated by the plus signs, while the other two difference images, Ce minus Pb and Ce minus I, are written in a negative sense, indicated by the minus signs, so that the four image elements due to the contrast medium, iodine, are mutually additive and thus are enhanced by a factor of four.

On the other hand, the two difference images I minus Ce and Ce minus Pb, in which bone and soft tissue appear black, are written in opposite senses, positively and negatively, so that the image elements due to bone and soft tissue tend to cancel out. The two difference images Pb minus Ce and Ce minus I in which the bone and soft tissue appear white are written in opposite senses, positively and negatively, so that the bone and soft tissue image elements tend to cancel out.

The alternate writing in positive and negative senses by the second storage tube 120 also largely cancels out any direct current offset in the signals from the first storage tube 96.

It is the usual practice to operate the X-ray apparatus through several revolutions of the filter wheel 24, while continuing to write the differential image on the second storage tube 120. As previously indicated, the second storage tube stores and integrates the differential image from cycle to cycle of the filter wheel, so that the degree of enhancement of the image elements due to the contrast medium increases from cycle to cycle.

During the read intervals of the second storage tube, the integrated differential image can be observed on the TV monitor. When the operator observes that an optimum differential image has been achieved, he can stop the operation of the television system by closing the start-stop switches 174a, b and c.

By changing the writing sequence in the second storage tube 120, the contrast medium, iodine in this case, can be written either white or black on the TV monitor 62. The iodine will be written in white if the I minus Ce and Pb minus Ce difference images are written in a positive sense, while the Ce minus Pb and Ce minus I difference images are written in a negative sense, as shown in FIG. 10. The iodine will be written in black if the I minus Ce and Pb minus Ce difference images are written in a negative sense, while the Ce minus Pb and Ce minus I difference images are written in a positive sense.

As previously indicated, logarithmic amplification has the advantage that difference images representing a small percentage of the unsubtracted video images will have a magnitude independent of the overall scale factor or gray shade of the unsubtracted video images.

Thus, two slightly different image elements I and I' may be represented by the following expodential functions:

$$I = I_0 e^{-\mu x}$$
$$I' = I_0 e^{-\mu' x}$$

In these equations $\mu$ and $\mu'$ represent the two slightly different absorption coefficients, while $x$ represents the thickness. If the logarithms are taken before subtraction, the equations become as follows:

$$\log I = \log I_0 - \mu x$$
$$\log I' = \log I_0 - \mu' x$$

The difference between the two logarithms is as follows:

$$\log I' - \log I = \log I_0 - \mu' x - \log I_0 + \mu x = (\mu - \mu') x$$

It will be seen that the constant term $\log I_0$ cancels out so that it is not a factor in the difference image.

Those skilled in the art will be able to assign specific values to the electronic components. However, it may be helpful to provide the following tables of suitable values:

| INTEGRATED CIRCUITS | TYPE NO. | TRANSISTORS | TYPE NO. |
|---|---|---|---|
| 154a, b | 7400 | 274 | 2N5134 |
| 170 | 74121 | 294 | 2N3568 |
| 186 | 7473 | 310a, b, c | 2N3568 |
| 194 | 7400 | 366 | 2N3568 |
| 196 | 7400 | 376 | 2N3568 |
| 214 | 74122 | 386 | 2N3568 |
| 230a, b | 7400 | 400 | 2N3568 |
| 246 | 74121 | 410 | 2N5134 |
| 264 | 7400 | 414 | 2N3568 |
| 334 | SN76502 | 420 | 2N3568 |
| 354 | 733 | 428 | 2N5140 |
| 470 | 7400 | 440 | 2N2102 |
| 474 | 7400 | 462 | 2N3568 |
| 478a, b | 7400 | 600 | 2N3440 |
| 488 | 74122 | 614 | 2N3440 |
| 490a, b | 7400 | 678 | 2N3440 |
| 496 | 7400 | 706 | 2N3440 |
| 506 | 7400 | 720 | 2N3440 |
| 508 | 7400 | 746 | 2N2102 |
| 510a, b | 7400 | 756 | 2N3440 |
| 514 | 7400 | 814 | 2N4400 |
| 518 | 7400 | 834 | 2N5134 |
| 520 | 7400 | | |
| 522 | 7410 | | |
| 524 | 7400 | | |
| 526a, b | 7400 | | |
| 528 | 7400 | | |
| 532 | 7400 | | |
| 534 | 7410 | | |
| 536a, b | 7400 | | |
| 538 | 7400 | | |
| 544a, b, c | GE SC142D | | |
| 630a, b | MC724P | | |
| 636 | MC790P | | |
| 638 | MC790P | | |
| 654 | MC788P | | |
| 658 | MC788P | | |
| 660 | MC788P | | |
| 668 | MC724P | | |

-continued

| INTEGRATED CIRCUITS | TYPE NO. | TRANSISTORS | TYPE NO. |
|---|---|---|---|
| 670 | MC788P | | |
| 672 | MC788P | | |
| 674 | MC788P | | |
| 676 | MC724P | | |
| 734 | MC788P | | |
| 738 | MC788P | | |
| 740 | MC788P | | |
| 766 | MC724P | | |
| 768 | MC788P | | |
| 772 | MC788P | | |
| 774 | MC788P | | |
| 776 | MC724P | | |
| 826 | 74121 | | |
| 844a, b | MC724P | | |
| 864 | MC724P | | |
| 866 | MC724P | | |
| 868 | MC799P | | |

| CAPACITORS | MICROFARADS OR PICOFARADS (pf.) |
|---|---|
| 156a, b | .1 |
| 166a, b | .01 |
| 182 | .1 |
| 208 | .01 |
| 216 | .1 |
| 224 | .1 |
| 232 | 2. |
| 240 | .01 |
| 248 | .01 |
| 258 | 2. |
| 272 | 175. |
| 292 | 10. |
| 312a, b, c | 4.7 |
| 344 | 100. |
| 364 | 100. |
| 374 | 100. |
| 460 | 6. |
| 468 | .1 |
| 482 | .1 |
| 494 | 1. |
| 500 | .1 |
| 570a, b, c | .1 |
| 574a, b, c | .1 |
| 626 | 1000. pf. |
| 632 | .001 |
| 648 | .001 |
| 686 | 1000. pf. |
| 732 | 1000. pf. |
| 762 | 1000. pf. |
| 824 | 8. |
| 832 | .22 |
| 846 | 200. |
| 854 | .001 |
| 862 | 1000. pf. |

| RESISTORS | OHMS | RESISTORS | OHMS |
|---|---|---|---|
| 160a, b | 1K | 402 | 820 |
| 166a, | 12K | 404 | 2.2K |
| 166b | 15K | 406 | 10.K |
| 172a, b | 2.2K | 408 | 39K |
| 180 | 50K | 412 | 2.2K |
| 188 | 10K | 416 | 100 |
| 188 | 39K | 418 | 2.2K |
| 206 | 22K | 422 | 680 |
| 218 | 15K | 424 | 20K |
| 220 | 10K | 426 | 1K |
| 234 | 4.3K | 430 | 10K |
| 236 | 50.K | 432 | 10K |
| 244 | 18.K | 438 | 8.2 |
| 252 | 10K | 444 | 50 |
| 254 | 10K | 446 | 820 |
| 260 | 620 | 456 | 250K |
| 262 | 50K | 458 | 27K |
| 266 | 1K | 464 | 3.3K |
| 268 | 20K | 466 | 50K |
| 280 | 300K | 472 | 30K |
| 282 | 27K | 484 | 270 |
| 284 | 91 | 486 | 690 |
| 296 | 500 | 496 | 10K |
| 298 | 1K | 502 | 220 |
| 300 | 470 | 516 | 3K |
| 302 | 62 | 530 | 2K |

| RESISTORS | OHMS | -continued RESISTORS | OHMS |
|---|---|---|---|
| 304 | 500 | 540 | 3K |
| 306 | 62 | 552 a, b, c | 1 |
| 308 | 1K | 566 a, b, c | 270 |
| 314 a, b, c | 25K | 568 a, b, c | 470 |
| 316 a, b, c | 1K | 576 a, b, c | 2.5 |
| 318 a, b, c | 1K | 582 a, b, c | 25 |
| 320 a, b, c | 1K | 590 | 5K |
| 348 | 1.8K | 594 | 33K |
| 350 | 500 | 596 | 500K |
| 352 | 1.8K | 598 | 56K |
| 356 a, b | 2.2K | 604 | 120K |
| 358 | 20K | 606 | 47K |
| 360 | 2.K | 612 | 330K |
| 362 | 2.2K | 613 | 1MEG. |
| 368 | 100K | 618 | 39K |
| 370 | 2K | 624 | 4.7K |
| 372 | 1.2K | 634 | 1K |
| 378 | 100K | 642 | 3.9K |
| 380 | 1.2K | 644 | 1.8K |
| 382 | 1.0K | 650 | 1.0K |
| 384 | 470K | 656 | 3.9K |
| 388 | 600 | 680 | 39K |
| 390 | 1.2K | 684 | 4.7K |
| 392 | 50K | 694 | 5K |
| 394 | 2.2K | 700 | 39K |
| 396 | 22K | 702 | 500K |
| 398 | 3.3K | 704 | 56K |
| 710 | 20K | | |
| 712 | 4.7K | | |
| 718 | 330K | | |
| 724 | 39K | | |
| 726 | 1 MEG. | | |
| 730 | 4.7K | | |
| 736 | 3.9K | | |
| 748 | 100K | | |
| 750 | 82K | | |
| 752 | 22K | | |
| 760 | 4.7K | | |
| 764 | 39K | | |
| 808 | 5K | | |
| 810 | 4.7K | | |
| 818 | 4.7K | | |
| 820 | 47K | | |
| 822 | 47K | | |
| 828 | 1K | | |
| 830 | 33K | | |
| 836 | 13K | | |
| 838 | 56K | | |
| 840 | 1K | | |
| 848 | 1K | | |
| 850 | 25K | | |
| 856 | 1K | | |
| 860 | 820 | | |

FIGS. 22–27 illustrate additional improvements in the method and apparatus of the present invention. As before, the improved method uses three independent X-ray spectra generated with three separate filters and X-ray tube voltages. The new technique also includes improved logarithmic treatment of the three different video signals. The storage tube subtraction scheme is similar to that already described herein. The improved method maintains a high order of sensitivity to iodine, or any other suitable contrast medium, but provides images which are much less sensitive to tissue and bone. The improved apparatus is of a fairly complex character, but is highly advantageous in that once optimum operating conditions have been found, no additional tuning will ordinarily be required to accommodate patient variations.

It will be helpful to set forth a brief theoretical analysis, involving the solution of the transmission equations for the improved method and apparatus represented by FIGS. 22–27.

Consider three filtered beams with effective energies $E_i$, ($i = 1, 2,$ or $3$) for spectra similar to those sketched in FIG. 7. Such spectra may be produced with the use of three different filters, containing iodine, cerium and lead in this case, using different values of X-ray tube voltage. Energy $E_1$ is just below the k-edge of the element of interest, which we will assume to be iodine for the purpose of this discussion, but may be any other suitable contrast medium. The other spectra are designed to have as little overlap as possible with energies chosen to satisfy approximately the condition that $$2\mu_2{}^t = \mu_1{}^t + \mu_3{}^t \quad 2\mu_2{}^B = \mu_1{}^B + \mu_3{}^B \tag{1}$$

where $\mu_i{}^t$ and $\mu_i{}^B$ are the absorption coefficients for tissue and bone. In practice the various absorption coefficients are linearly weighted, as described below, so that condition (1) is used only as an initial aid in the choice of spectra. Since the dependence of X-ray detection on the effective energy can be absorbed into the various constants which appear in the solution of the equations we will temporarily assume for simplicity that no such dependence exists and consider the number of transmitted photons $N_i(x,y)$ at point $(x,y)$ and assume a uniform incident flux $N_o$ for each beam. For the purpose of the present discussion we will also neglect beam hardening effects which will be treated below. We will assume that at point $(x,y)$ the beam passes through thickness $t(x,y)$, $t_B(x,y)$ and $t_I(x,y)$ of tissue, bone and iodine, expressed in gms/cm$^2$.

The number of transmitted photons is then given by the three equations $$N_i(x,y) = N_o e^{-\mu_i{}^B t_B(x,y) - \mu_i{}^t t(x,y) - \mu_i{}^I t_I(x,y)} \tag{2}$$

Our goal is to isolate the iodine image $t_I(x,y)$ which we wish to display without contributions from $t(x,y)$ or $t_B(x,y)$. In the interest of apparatus simplicity it is desirable to restrict the solution to a series of linear operations to be performed by the subtraction apparatus. Since it is not possible to construct a linear combination of exponentials to insure cancellation of bone and tissue contributions for all values of the bone and tissue thickness, it is desirable to deal with logarithmically amplified signals. After passing the fluoroscopic television signals through such an amplifier the following equations are obtained $$L_i = -ln\left(N_i/N_o\right) = \mu_i{}^B t_B + \mu_i{}^t t + \mu_i{}^I t_I \tag{3}$$

where the $x,y$ dependences of $L_i$, $t_B$, $t$ and $t_I$ are assumed, but no longer explicitly written. This set of three linear equations in three unknowns can be solved at each point by taking an appropriate linear combination of the $L_i$. The iodine image, $t_I(x,y)$, representing a two dimensional display of the iodine distribution, is obtained by constructing a linear combination which cancels the coefficients of $t_B$ and $t$ at all points and has the form $$t_I(x,y) = \alpha L_1 - 2\beta L_2 + \gamma L_3 \tag{4}$$

where the linear form chosen, $\alpha = \beta = \gamma = 1$, would be an appropriate solution if equations (1) could be simultaneously satisfied. In general, however, this is only approximately true and the image $t_I(x,y)/\alpha$ is a linear combination of three logarithmic images obtained by appropriate settings of the amplifications of images $L_2$ and $L_3$.

To maximize the sensitivity of the image storage and linear combination process it is desirable to construct the solution in such a way that all images presented to the image processing equipment are nearly equal in amplitude. This is true whether the apparatus is analog or digital. Therefore, a more practical, mathematically equivalent form for the solution is the following expression, in which $\alpha$ means "is proportional to":

$$t_i(x,y) \alpha (L_1 - k_2 L_2) + k_4(k_3 L_3 - k_2 L_2) \qquad (5)$$

The constants $k_2$ and $k_3$ are chosen so that, in the presence of tissue along $L_1 = k_2 L_2 = k_3 L_3$. This implies that $$k_2 = \mu_1{}^t/\mu_2{}^t \quad k_3 = \mu_1{}^t/\mu_3{}^t \qquad (6)$$

In addition, the $L_2$ image is used twice in order to separately cancel the tissue contributions to $L_1$ and $L_3$. The solution is then reduced to the weighted sum of two difference images which have zero tissue contributions. Since the absorption coefficient of bone is a monotonically decreasing function of bone in this energy region, the two difference images have bone contributions of opposite sign and, in general, unequal size. Since the tissue is cancelled in each image the constant $k_4$ can be chosen to cancel bone also. This occurs for $$k_4 = \frac{\mu_1{}^B - k_2 \mu_2{}^B}{k_3 \mu_3{}^B - k_2 \mu_2{}^B} \qquad (7)$$

Multiplication by $k_4$ is achieved by appropriate gain multiplying during the second stage of subtraction and integration, which is performed by the second storage tube.

Using equation 5 the final image is seen to be $$t_i(x,y) \alpha \Delta\mu_I t_I + \Delta\mu_t t + \Delta\mu_B t_B$$

$$\Delta\mu_i = \left[ \left( \mu_i' - \frac{\mu_i' \mu_2'}{\mu_2'} \right) + \frac{(\mu_i{}^B - \mu_i' \mu_2{}^B/\mu_2')}{(\mu_3{}^B - \mu_3' \mu_2{}^B/\mu_2')} \left( \frac{\mu_3' - \mu_3' \mu_2'}{\mu_2'} \right) \right] \qquad (8)$$

where $$\Delta\mu_t = 0 \quad \Delta\mu_B = 0$$

The absorption coefficient discontinuity at the K-edge is $(36-6) = 30 \text{cm}^2/\text{gm}$. For spectra formed at tube voltages of 45, 60 and 70 kVp with filters of 150 mg/cm² of Iodine, 200 mg/cm² of Cerium and 400 mg/cm² of Pb, respectively, our computer calculations estimate absorption coefficient of $$\mu_1{}^t = .36 \quad \mu_2{}^t = .29 \quad \mu_3{}^t = .22$$
$$\mu_1{}^B = .93 \quad \mu_2{}^B = .61 \quad \mu_3{}^B = .32$$
$$\mu_1{}^I = 9.6 \quad \mu_2{}^I = 23.7 \quad \mu_3{}^I = 10.3$$

at 15 cm tissue, 0 bone, which combine to yield the effective absorption coefficients, $$\Delta\mu_I = -11.4 \quad \Delta\mu_B = 0 \quad \Delta\mu_t = 0$$

The mathematical solution described in the form of equation (5) can be implemented by means of the rotating four-segment filter wheel shown in FIG. 9.

The corresponding $N_i$ are $N_1$ for the iodine filter, $N_2$ for the cerium filters and $N_3$ for the lead filters. As the filter rotates, phototransistors viewing timing marks on the wheel alternately trigger three triacs tapped into the primary side of the kVp control circuit, in the same manner as discussed in connection with FIG. 19. The position of the filter wheel also selects one of three channels on the multiplexed amplifier chain shown in FIG. 22. The input amplifiers prepare the signals for presentation to the logarithmic amplifier. The output amplifiers determine the coefficients $k_2$ and $k_3$. These are chosen by aligning a continuous plexiglass wedge so that its slope provides continually increasing absorber thickness along either the $x$ or $y$ axis of the television scan. The exponentially decreasing transmitted intensity produces a straight line at the output of the logarithmic amplifier as shown in the oscilloscope trace in FIG. 23. The constants $k_2$ and $k_3$ are adjusted so that the three straight lines associated with each of the spectra are identical in amplitude and slope.

As the four filter segments pass through the X-ray beam, the first storage tube generates four successive images, each of which represents the difference between successive images stored on the target of the first tube. These images are then integrated on the second storage tube which weights them by factors of $\pm 1$ or $\pm k_4$ in order to integrate iodine information and cancel bone and unwanted dc image components.

The tissue and bone cancellation conditions described by equations (5), (6), and (7) can be assumed to be valid only at one combination of bone and tissue thicknesses. It is necessary to study how well this cancellation is maintained as $t$ and $t_B$ are varied. This was done using a computer analysis which studied the effects of hardening on the spectra measured by Waggener, et al., as reported in RADIOLOGY 105:169–175, October 1975, and Epp and Weiss, as reported in PHYS. MED. BIOL., Vol. II. No. 2, pp 225–238, 1966. The hardening appears as an approximately linear decrease in absorption coefficients with tissue thickness.

FIG. 14 shows $\mu_i{}^t$ as a function of $t$ for $t_b = 0$ while FIG. 15 shows the same for $\mu_i{}^B$. Each figure also displays the average of the Iodine and Lead coefficients at 0 gm/cm² bone. The comparison of this average to the Cerium coefficient roughly suggests that the image balance conditions can be maintained away from some chosen balance point. However, these graphs do not include the effects of the various linear coefficients and are not the most sensitive method for predicting the ratio of desired signal to undesired tissue and bone effects.

A better method of checking how well the balance condition is maintained is to study the actual contributions of bone, tissue and Iodine over a range of bone and tissue thicknesses. At the thickness where the chosen solution forces the tissue and bone residuals to be zero, only an Iodine residual is present. Away from the equilibrium condition (e.g. 15 cm tissue, 0 cm bone), the tissue and bone contributions increase. Ideally, the residuals from Iodine should always be greater than from tissue or bone for all values between 10 and 20 gm/cm² tissue and 0 and 2 gm/cm² bone.

The principle behind choosing proper filters is that the decrease in $\mu$ with thickness can be approximated by a straight line. One must therefore choose spectra which harden in such a way that the following condition is approximated $$\frac{\mu_1'(t)}{\mu_1'(t_o)} = \frac{\mu_2'(t)}{\mu_2'(t_o)} = \frac{\mu_3'(t)}{\mu_3'(t_o)} \qquad (9)$$

with similar conditions for the bone coefficients.

Since the lowest energy (iodine-filtered) beam tends to harden faster than those of higher energy, the condition of equation (5) can only be realized by using increasing filtration for decreasing $k$Vp. A near ideal condition is shown in FIG. 24. Note, that a very thick Iodine filter and low $k$Vp are needed. These conditions require the use of a special X-ray tube having unusually high intensity. The use of a standard fluoroscopic tube does not usually afford sufficient intensity to allow for heavy Iodine filtration. With the use of a standard fluoroscopic X-ray tube, the conditions shown in FIG. 25, can be achieved.

A correction which allows incresed flexibility in the choice of spectra by approximately maintaining the condition of equation (8) involves the use of a $t$ dependent amplifier gain which can be achieved by feeding back a correction factor $\gamma$ involving the first power of the logarithmic output signal. It can be shown that the gain correction factor can be approximated by $$\gamma_i(t) = \left\{ 1 - a_i{}^t/<\mu_i{}^t> [L_i{}^{(t)} - L_i{}^{(to)}] \right\} \qquad (10)$$

where $a_i{}^t$ is the slope of the lines in FIG. 14 and $<\mu_i{}^t>$ is the average tissue absorption coefficient in the tissue range of interest.

In practice, this correction factor may be represented by a tuning control which is adjusted along with amplification and dc level controls in the various amplifiers until the straight line shown in FIG. 23 is obtained at the input to the storage tube. Any effects of scatter buildup which might tend to alter the transmission properties of the three spectra are tuned out at this point. Because of the convenient end-point check we have not found it necessary to study the details of the scatter field thus far in our work. Such studies should be done in the future to determine the extent of contrast degradation by scatter as a function of patient thickness, field size, etc.

Consideration should be given to the requirements on system accuracy. In this connection, we will consider the size of the differential absorption edge signal and the size of competing contributions to the final image due to television system nonlinearities and errors in the logarithmic amplifier.

Let us first consider the percentage of the video dynamic range occupied by a typical iodine signal. Assume that the logarithmic amplifier has a form given by $$V_{out} = a \log V_{in} + b \qquad (11)$$

Assuming that the input video $V_{in}$ is proportional to the transmitted X-ray intensity $$V_{in} \propto e^{-\mu_t t - \mu_B t_B - \mu_I t_I} \qquad (12)$$

In the unsubtracted logarithmic video signal the iodine contribution is negligible and the video dynamic range is given by $$\Delta V \propto <\mu_t{}^t> (t_{max} - t_{min}) + <\mu_t{}^B> (t_{B\ max} - t_{B\ min}) \qquad (13)$$

where the absorption coefficients are the average coefficients of the lowest energy spectrum in the tissue range of interest. Using equation (8) the iodine signal $\Delta V_I$ is on the order of $$\Delta V_I = \Delta \mu_I t_I \cong 11\ t_I \qquad (14)$$

For a 5 cm variation of tissue and a 2 gm/cm² variation of bone, in the case of 45 kVp —175 mg/cm²I, 60 kVp —400 mg/cm² Ce and 70 kVp 400 mg/cm² Pb, the fraction of the total dynamic range occupied by the iodine difference signal is given by $$\Delta V_I/\Delta V = 0.3\% \qquad (15)$$

Therefore, each milligram of iodine provides a signal which is approximately 0.3% of the full scale video range, assuming the worst case of bone over the thickest tissue. For clinical situations where the thickness variations are larger or smaller than those of this example, the percent signal varies approximately as the inverse of the total intensity variation as long as logarithmic amplification is used.

Now consider the size of difference signals due to nonuniformities in the imaging system up to and including the logarithmic amplifier. Such effects tend to distort the shape of the lines such as that of FIG. 23. Because the X-ray transmission is different for the three spectra used, nonuniformities may not propagate through the system in exactly the same way. On the other hand, a large part of the nonlinearity is shared by all three channels and cancels out. In order to quantitate this we have calculated the contributions to the final image due to two known effects.

1. Areal nonuniformity in the system. This was modeled by a sinusoidal variation across the image with zero % on the edges and 5% in the middle.
2. Deviations of the logarithmic amplifier from true logarithmic behavior. This was also assumed to be a sinusoidal error taken to be zero at the maximum and minimum of the video range with a ± 1db$_V$ error in 30db$_V$ ($\simeq$3%).

With these assumptions the logarithmic signal associated with a continuous wedge phantom deviated from that of FIG. 23 as shown in FIG. 26. The calculated output signals for spectra 1 and 3 are shown. Most of the error, which is on the order of 0.5%, is due to lack of field flatness. The deviations from logarithmic behavior are coupled in only through the field flatness effect and, in the absence of this effect, would be shared in common, giving rise to zero difference signals.

Therefore, the requirements on system performance are not unreasonable for iodine concentration on the order of 1 mg/cm² for thickness variation on the order of 5 cm tissue and 2 mg/cm² bone or equivalently for 10 cm of tissue in the absence of bone. Obviously for greater variation or smaller concentrations of iodine, greater care must be taken.

Consideration should also be given to beam intensity requirements. Because of the heavy filtration and low X-ray energies involved in the absorption edge imaging method the beam intensity requirements must be calculated for any clinical imaging situation which is considered. In this connection, we will calculate the exposure needed before filtration, at the patient's skin, and at the detector. For the purpose of this calculation we will calculate the exposures needed to provide a three standard deviation contrast difference between an area of iodine and its surroundings.

The logarithmic image will be assumed for simplicity to be $$L = (\ln N_1 - \ln N_2) + (\ln N_3 - \ln N_2) \qquad (16)$$

in accordance with the approximation of eq. (4). We will also assume that the filters have been chosen so that $$\Delta N_1/N_1 \simeq \Delta N_2/N_2 \simeq \Delta N_3/N_3 = \sqrt{N/N} \qquad (17)$$

where N is the number of transmitted photons. Then, adding the statistical errors in quadrature we obtain $$\Delta L \simeq \sqrt{4N/N} \qquad (18)$$

Now consider two rays A and B through the patient. Ray A passes through no iodine and the differential logarithmic image is $$L_A \simeq 0 \qquad (19)$$

Assume that Ray B passes through an area of iodine which absorbs x percent more X-rays for the cerium filtered beam than for the other two beams. Then $$N_1 \simeq N_3 = (1 + 0.01\%) N_2 \qquad (20)$$

and $$L_B = 2 \ln (1 + 0.01\%) N_2 - 2 \ln N_2 \simeq 0.02x \qquad (21)$$

The three standard deviation criterion is then equivalent to $$.02x = 3 \frac{\sqrt{4N}}{N} \text{ OR } N = \frac{9 \times 10^4}{x^2} \text{ detected photons} \qquad (22)$$

To convert this to exposure assume a detection efficiency of 30% and consider a square object of side $d$ mm. Then the exposure required at the detector can be approximated using the 35 keV relationship, $1 mR = 2 \times 10^5$ photons/mm$^2$, so $$\left(\frac{E}{4}\right) = \frac{N}{d^2} \times \frac{1 mA}{2 \times 10^5} \times \frac{1}{.3}$$

where (E/4) is the exposure associated with each of the four filter segments. The total exposure is then given by $$E = 6.8 \ mR/x^2 d^2 \qquad (23)$$

For 1mg/cm$^2$, $x \simeq 1.5$ and $E \simeq 3$ mR for a 1 mm object. The patient skin exposure is given by $$E_s = EAp \qquad (24)$$

where Ap is a factor to account for the attenuation due to the patient and a slight decrease in beam intensity due to the inverse square law. For an attenuation factor of 200 (15 cm tissue or 10 cm tissue + 2 gm/cm$^2$ bone) an exposure of 600 mR would be required for 1 mm$^2$, 1 mgm/cm$^2$ Iodine object. The exposure requirements for 1 and 2 mgm/cm$^2$ Iodine are plotted in FIG. 27 as a function of object size using the attenuation factor and detection efficiency assumed above.

Having established that the required exposures are not prohibitively high we must examine the requirements placed on the X-ray generator. The exposure which would occur at the patient in the absence of filtration is related to the actual skin exposure by $$E = E_s A_f \qquad (25)$$

where $A_f$ is the filter attenuation factor, typically about a factor of 15. Thus, the generator would need to deliver an unfiltered exposure of 9R for the above example. Present X-ray tubes operated in radiographic mode can deliver such an exposure in several seconds. We have previously reported on Iodine images taken with the two filter technique using a beam current of 100 mA for times of two to five seconds and phantom thickness between 15 and 20 cm. Whether the present technique can be applied in clinical situations requiring sub-second imaging times will depend upon the spatial resolution required, the iodine concentration present and the patient thickness.

In order to test the limit of iodine sensitivity in the presence of tissue variations and bone, a Picker thyroid phantom was filled with a solution giving iodine concentrations of 4 mgm/cm$^2$ in the left lobe and 2 mg/cm$^2$ in the right lobe. This phantom was placed over a plastic wedge giving a phantom thickness varying between 6 and 10 cm. A vertebral bone was also placed on top of the thyroid phantom. Both lobes of the thyroid phantom were clearly visible in the final difference image, while the images of the wedge and the bone were scarcely visible.

With the method and apparatus of the present invention, it is felt that 1 mg/cm$^2$ iodine concentrations will be measureable in the presence of most bone and tissue variations found in the body.

It may be helpful to describe additional details of the apparatus shown in FIG. 22. Such apparatus constitutes an illustrative embodiment of the modified form of the present invention, as referred to in the preceding general and theoretical discussion, directed to FIGS. 22–27.

More specifically, FIG. 22 illustrates a differential X-ray system or apparatus 910, comprising a television camera 920 for converting the X-ray images into signals, adapted to be displayed as television images. The television camera 920 may be the same as the television camera 46 of FIG. 1. Moreover, the X-ray images may be produced in the same manner as described in connection with FIG. 1. Thus, the X-rays from the X-ray tube 16 may be directed through the filter wheel 24 and the patient 12 to the intensifier screen 22, which converts the X-ray to visible light so that the visible images can be presented to the television camera 920.

The filter wheel 24 may be the same as described in connection with FIGS. 1 and 9, so that successive X-ray images are produced using the iodine (I) filter 24b, the cerium (Ce) filter 24b, the lead (Pb) filter 24c, and the second cerium (Ce) filter 24d. The lead filter 24c may utilize lead foil as the filtering medium, while the iodine and cerium filters 24a, 24b and 24d may comprise liquid filled cells containing solutions of iodine and cerium compounds.

It has been found that brass foil may be substituted for the lead foil in the filters section 24c. Brass foil has an advantage that the thickness of the foil generally has a greater degree of uniformity then in the case of lead foil.

It is possible to provide three individual channels 922a, b and c for transmitting the output signals of the television camera 920 to the input of a logarithmic amplifier 924, which may be the same as the logarithmic amplifier 334 described in connection with FIG. 16. The channels 922a, b and c are operative individutive, when the iodine, cerium and lead filters are operative, respectively.

The channels 922a, b and c are rendered operative in sequence by relays or control switches 926a, b and c, which may be essentially the same as the relays 326a, b and c described in connection with FIG. 17. The relays may be operated in sequence in the manner described in connection with the circuits of FIG. 18. Such circuits are designated sequence control circuits 928 in FIG.

Provision is made in the individual channels 922a, b and c for adjusting the video signals fed to the log amplifier 924 when the iodine, cerium and lead filters are operative. As shown in FIG. 22, the channels 922a, b and c include direct current level controls 930a, b and c, gain controls 932a, b and c, and amplifiers 934a, b and c. In the usual operation of the X-ray system, the dc level controls 930a, b and c and the gain controls 932a, b and c are generally adjusted so that closely similar video signals are supplied to the log amplifier 924 when the iodine, cerium and lead filters are operative. The amplifier 924 is in the circuit for all of the filters, so that the logarithmic amplification is always the same. It is possible to provide three individual channels 936a, b and c for transmitting the output signals from the logarithmic amplifier 924 to the input of a video switch 938 which has its output connected to the input of a video difference detector 940. The video switch 938 and the video difference detector 940 may be the same as the video switch 52 and the video difference detector 54, described in connection with FIGS. 1 and 2. As before, the video difference detector 940 preferably utilizes a storage tube which may be the same as the storage tube 96 described in connection with FIG. 2.

The channels 936a, b and c are rendered operative when the iodine, cerium and lead filters are operative. This may be accomplished by utilizing control relays or switches 942a, b and c which may be essentially the same in construction and operation as the relays 326a, b and c, described in connection with FIGS. 17 and 18. The relays 942a, b and c may be operated by the sequence control circuits 928, which also operate the relays 926a, b and c and may be essentially the same as the control circuits of FIG. 18.

Provision is preferably made for adjusting the direct current level and the amplification of the signals supplied from the output of the log amplifier 924 to the video difference detector 940. As shown in FIG. 22, the individual channels 936a, b and c preferably incorporate direct current level controls 944a, b and c, gain controls 946a, b and c, and amplifiers 948a, b and c. In the usual operation of the X-ray system, the dc level controls 944a, b and c and the gain controls 946a, b and c will be adjusted to provide the requisite values of $k_2$ and $k_3$, as described above in connection with equations (5) and (6). This adjustment can easily be accomplished by positioning a continuous wedge in the X-ray field, to simulate a range of patient thicknesses. The slope of the wedge provides a continuously increasing absorber thickness along with the x or y axis of the television scan. The exponentially decreasing transmitted intensity of the X-rays for each filter produces a straight line at the input of the video difference detector 940 due to the action of the logarithmic amplifier 924. Such straight line can be displayed on an oscilloscope connected to the input of the video difference detector 940. A representative oscilloscope trace is shown in FIG. 23. The dc level controls 944a, b and c and the gain controls 946a, b and c are adjusted so that the three straight lines, associated with the X-ray spectra produced by the use of the iodine, cerium and lead filters, are identical in amplitude and slope.

By thus adjusting the coefficients $k_2$ and $k_3$, the video signals presented to the first storage tube in the video difference detector 940 are closely similar, so that effective cancellation of the background signals due to soft tissue can be achieved easily and accurately.

As described in connection with FIG. 1, the output of the video difference detector 940 is transmitted through a video switch 950 to an integrating subtraction and storage device 952, which may be the same as the device 58 of FIG. 1. The video switch 950 may be the same as the video switch 56 of FIG. 1. The storage device 952 may employ a second storage tube, which may be the same as the silicon storage tube 120, described in connection with FIG. 3.

However, an additional gain control circuit 954 is preferably connected to the storage device 952 of FIG. 22, to obtain the requisite value of the coefficient $k_4$, as described in connection with equation (7). The effective gain can readily be controlled by changing the biasing voltage supplied to a control grid G1 of the second storage tube. Such control grid was designated 130G1 in the description of the silicon storage tube 120 of FIG. 3, which may also be used in the system of FIG. 22. The gain control circuit 954 is connected to the sequence control circuit 928, which is arranged so that a first gain adjustment prevails when the iodine filter 24a and the first cerium filter 24b are operative, while a second gain adjustment prevails when the lead filter 24c and the second cerium filter 24d are operative. In the sequence diagram of FIG. 6, which is applicable to the system of FIG. 22, the first gain level may be utilized during television frames 1–18, while the second gain level is employed during television frames 19–36. The cycle is then repeated. These gain levels are adjusted to produce cancellation of the video signals due to the presence of bone in the patient. The gain levels can readily be adjusted by using a bone phantom in the X-ray field scanned by the television camera. By thus adjusting the gain levels, it is possible to achieve cancellation of the background image elements due to both soft tissue and bone in the patient, so that the remaining image elements on the second storage tube will be due solely to the contrast medium, such as iodine.

As before, the output signals from the integrating subtraction and storage device 952 are transmitted through a video switch 956 to a television monitor 958 which displays the differential X-ray image due to the contrast medium. The video switch 956 and the television monitor 958 may be the same as the corresponding components 60 and 62, described in connection with FIG. 1.

In FIG. 22, the operating connections between the sequence control circuit 928 and the relays 926a, b and c are represented by control lines 960a, b and c. The control lines between the sequence control circuit 928 and the relays 942a, b and c are designated 962a, b and c.

The system of FIG. 22 may utilize the KVP control circuits 18 which were previously described in connection with FIGS. 1 and 18. However, the control circuits 20 for regulating the milliamperes in the X-ray tube are not needed in the system of FIG. 22, because of the provision of the individually adjustable channels 922a, b and c and 936a, b and c, along with the gain control circuit 954.

As discussed in connection with equation (10), the system of FIG. 22 preferably provides means for feeding back a correction factor involving the first power of the logarithmic output signal, to provide increased flexibility in the choice of X-ray spectra. In FIG. 22, such means comprises a linearity control circuit 964 which receives the output signal from the log amplifier 724. The linearity control circuit develops a control signal of the form represented by equation (10) and supplies such control signal to the gain control circuits 946a, b and c. This control signal produces improved linearity over a wider range of patient thickness variations. The control signal could also be supplied to the gain control circuits 932a, b and c.

We claim:

1. A method of producing differential X-ray images to improve the visibility of a contrast medium having a K absorption edge at a predetermined X-ray energy, comprising the steps of producing first, second and third X-ray images using first, second and third X-ray spectra at first, second and third X-ray energy levels;

said first energy level being below said K edge energy;

said second energy level being above said K edge energy;

said third energy level being above said second energy level;

and subtractively combining said second X-ray image with the average of said first and third X-ray images to produce a differential X-ray image in which any image elements due to background soft tissue and bone are largely cancelled out while image elements due to said contrast medium are enhanced.

2. A method according to claim 1,
in which said second X-ray image is combined subtractively with the average of said first and third X-ray images by additively considering said second X-ray image twice and subtracting said first and third X-ray images to produce the differential X-ray image.

3. A method according to claim 1,
in which said second X-ray image is subtractively combined with the average of said first and third X-ray images by multiplying said second X-ray image by two and subtracting said first and third X-ray images to produce said differential X-ray image.

4. A method according to claim 1,
in which said second X-ray image is subtractively combined with the average of said first and third X-ray images by producing two versions of said second X-ray image,
combining said two versions additively,
and subtracting said first and third images to produce a differential X-ray image.

5. A method according to claim 1,
in which four X-ray images are produced,
including two versions of said second X-ray image alternating with said first and third X-ray images,
said two versions being combined additively while said first and third X-ray images are combined subtractively therewith to produce a differential X-ray image.

6. A method according to claim 1,
in which said first, second and third X-ray spectra are produced by using a single X-ray source with first, second and third X-ray filters.

7. A method according to claim 6,
in which said first, second and third filters contain iodine, cerium and lead, respectively.

8. A method according to claim 6,
in which said X-ray source is used with first, second and third anode voltages with said first, second and third filters.

9. A method according to claim 8,
in which said second voltage is greater than said first voltage,
while said third voltage is greater than said second voltage.

10. A method according to claim 6,
in which said X-ray source is operated at first, second and third intensity levels with said first, second and third filters.

11. A method according to claim 10,
in which said second intensity level is greater than said first intensity level,
while said third intensity level is greater than said second intensity level.

12. A method according to claim 10,
in which said second filter is denser than said first filter,
while said third filter is denser than said second filter,
said second intensity level being greater than said first intensity level,
while said third intensity level is greater than said second intensity level.

13. Apparatus for producing differential X-ray images to improve the visability of a contrast medium having a K absorption edge at a predetermined K edge X-ray energy, comprising means for successively producing first, second and third X-ray spectra at first, second and third X-ray energy levels;

said first energy level being below said K edge energy;

said second energy level being above said K edge energy;

said third energy level being above said second energy level;

means for producing first, second and third X-ray images using said first, second and third X-ray spectra;

and combining means for subtractively combining the average of said first and third X-ray images with said second X-ray image to produce a differential X-ray image in which any image elements due to soft tissue and bone are largely cancelled out while image elements due to said contrast medium are enhanced.

14. Apparatus according to claim 13,
in which said combining means comprises means for additively doubling said second X-ray image and subtracting said first and third X-ray images to produce the differential X-ray image.

15. Apparatus according to claim 13,
including means for producing first and second versions of said second X-ray spectrum,
and means for using said first and second versions of said second X-ray spectrum to produce first and second versions of said second X-ray image,
said combining means including means for additively combining the first and second versions of said second X-ray image while subtracting said first and third X-ray images therefrom to produce the differential X-ray image.

16. Apparatus according to claim 13,
including means for producing first and second versions of said second X-ray spectrum alternately with said first and third X-ray spectra,
and means for using said first and second versions of said second X-ray spectrum to produce first and second versions of said second X-ray image alternately with said first and third X-ray images,
said combining means including means for additively combining said first and second versions of said second X-ray image while subtracting said first and third X-ray images to produce the differential X-ray image.

17. Apparatus according to claim 13,
in which said means for producing first, second and third X-ray spectra comprise an X-ray source for producing an X-ray beam,
and first, second and third X-ray filters movable into said beam for producing said first, second and third X-ray spectra.

18. Apparatus according to claim 17,
in which said first, second and third filters contain iodine, cerium and lead, respectively.

19. Apparatus according to claim 17,
in which said X-ray source includes an X-ray tube having an anode and a cathode,
and means for producing first, second and third anode voltages between said anode and said cathode in timed relationship to the movement of said first, second and third filters into said X-ray beam.

20. Apparatus according to claim 17,
in which said X-ray source includes an X-ray tube having an anode and a cathode,
and means for producing first, second and third progressively greater anode voltages between said anode and said cathode in timed relationship to the movement of said first, second and third filters into said X-ray beam.

21. Apparatus according to claim 13,
including means for varying the intensity of said X-ray spectra to first, second and third intensity levels for said first, second and third X-ray spectra.

22. Apparatus according to claim 17,
in which said X-ray source includes means for varying the electron current between said cathode and said anode to first, second and third levels in timed relationship to the movement of said first, second and third filters into said X-ray beam.

23. A method of producing differential X-ray images to improve the visibility of a contrast medium having a K absorption edge at a predetermined K edge X-ray energy,
comprising the steps of successively producing first, second, third and fourth X-ray images using first, second, third and fourth X-ray spectra at first, second, third and fourth X-ray energy levels;
said first energy level being below said K edge energy;
said second energy level being above said K edge energy;
said third energy level being above second energy level;
said fourth energy level being the same as said second energy level;
said fourth X-ray image being a duplicate of said second X-ray image;
subtractively combining each successive pair of images to produce four difference images;
and combining said four difference images by alternately writing said difference images in a negative and a positive sense;
whereby image elements due to soft tissue and bone are largely cancelled out while image elements due to the contrast medium are enhanced.

24. A method according to claim 23,
including the additional step of logarithmically amplifying said first, second, third and fourth X-ray images.

25. A method according to claim 23,
in which a plurality of cycles of said first, second, third and fourth X-ray images are produced,
said differential image being integrated by writing and storing said four difference images over said cycles.

26. A method of producing differential X-ray images to improve the visibility of a contrast medium having a K absorption edge at a predetermined K edge X-ray energy,
comprising the steps of producing first, second, third and fourth X-ray images using first, second, third and fourth X-ray spectra at first, second, third and fourth X-ray energy levels;
said first energy level being below said K edge energy;
said second energy level being above said K edge energy;
said third energy level being above second energy level;
said fourth energy level being the same as said second energy level;
said fourth X-ray image being a duplicate of said second X-ray image;
converting said X-ray images into successive first, second, third and fourth television images;
subtractively combining successive pairs of said television images to produce four difference images;
and combining said four difference images by writing said difference images alternately in a negative sense and in a positive sense to produce a differential image in which image elements due to soft tissue and bone are largely cancelled out while image elements due to the contrast medium are enhanced.

27. A method according to claim 26,
including the additional step of logarithmically amplifying said first, second, third and fourth television images whereby the amplified images include terms proportional to the absorption coefficients of soft tissue and bone.

28. A method according to claim 26,
including the production of a plurality of cycles of said first, second, third and fourth X-ray images,
the differential image being integrated by successively writing and storing said four difference images over said cycles.

29. Apparatus for producing differential X-ray images to improve the visibility of a contrast medium having a K absorption edge at a predetermined K edge X-ray energy,
comprising means for successively producing first, second, third and fourth X-ray spectra at first, second, third and fourth energy levels;

said first energy level being below said K edge energy;

said second energy level being above said K edge energy;

said third energy level being above said second energy level;

said fourth energy level being the same as said second energy level;

said fourth X-ray spectrum being a duplicate of said second X-ray spectrum;

means for using said first, second, third and fourth X-ray spectra to produce successive first, second, third and fourth X-ray images;

said fourth X-ray image being a duplicate of said second X-ray image;

first combining means for subtractively combining the successive pairs of said X-ray images to produce four successive difference images;

and second combining means for combining said four difference images by alternately writing said difference images in a negative sense and a positive sense to produce a differential image in which the image elements due to the contrast medium are enhanced while the image elements due to soft tissue and bone are largely cancelled out.

30. Apparatus according to claim 29,
including means for logarithmically amplifying said first, second, third and fourth X-ray images for presentation to said first combining means.

31. A method according to claim 29,
in which said second combining means include storage means for storing and integrating the four difference images as written over a plurality of cycles of said X-ray images.

32. Apparatus for producing differential X-ray images to improve the visibility of a contrast medium having a K absorption edge at a predetermined K edge X-ray energy.

comprising X-ray source means for successively producing first, second, third and fourth X-ray spectra at first, second, third and fourth X-ray energy levels;

said first energy level being below said K edge energy;

said second energy level being above said K edge energy;

said third energy being above said second energy level;

said fourth energy level being the same as said second energy level;

said fourth X-ray spectrum being a duplicate of said second X-ray spectrum, means for producing first, second, third and fourth X-ray images using said first, second, third and fourth X-ray spectra;

said fourth X-ray image being a duplicate of said second X-ray image;

television means for converting said X-ray images into first, second, third and fourth television images;

first combining means for subtractively combining the successive pairs of television images to produce four difference images;

and second combining means for combining said four difference images by alternately writing said difference images in a negative sense and a positive sense to produce a differential image in which the image elements due to the contrast medium are enhanced while the image elements due to soft tissue and bone are largely cancelled out.

33. Apparatus according to claim 32,
including means for logarithmically amplifying said television images for presentation to said first combining means, whereby exponential contributions to the television images due to soft tissue and bone are rendered linear and whereby difference images representing a small percentage of the unsubtracted television images will have a magnitude independent of the overall scale factor or gray shade of the unsubtracted television images.

34. Apparatus according to claim 32,
in which said second combining means include storage means for storing and integrating said difference images written alternately in a negative sense and a positive sense, to produce additional enhancement of the image elements due to the contrast medium.

35. Apparatus according to claim 32,
in which said X-ray source means include an X-ray tube for producing an X-ray beam;

and first, second, third and fourth X-ray filters movable successively into said beam for producing said first, second, third and fourth X-ray spectra.

36. Apparatus according to claim 35,
in which said X-ray tube includes an anode and a cathode, said X-ray source means including means for providing changeable anode voltage between said anode and said cathode to afford first, second, third and fourth anode voltages while said respective first, second, third and fourth X-ray filters are in said X-ray beam.

37. Apparatus according to claim 35,
in which said X-ray source means includes means for changing the electron current in said X-ray tube to provide first, second, third and fourth electron current levels while said respective first, second, third and fourth X-ray filters are in said X-ray beam.

38. Apparatus according to claim 32,
in which said television means include gain changing means for providing first, second, third and fourth levels of gain while said respective first, second, third and fourth X-ray spectra are being produced.

39. Apparatus according to claim 32,
in which said television means included means for converting said X-ray images into first, second, third and fourth video signals, and means for logarithmically amplifying said video signals for presentation to said first combining means, whereby exponential contributions to the video signals due to soft tissue and bone are rendered linear.

40. Apparatus according to claim 39,
in which said television means includes gain changing means for providing adjustable levels of gain while said respective X-ray spectra are being produced to afford similar signal levels for all of said spectra at the input of said means for logarithmically amplifying said video signals.

41. Apparatus according to claim 32,
in which said television means includes a television camera for converting said X-ray images into first, second, third and fourth video signals, a logarithmic amplifier for amplifying said video signals for presentation to said first combining means, and gain and level changing controls in circuit with said logarithmic amplifier for modifying the amplitude level of the video signals at the output of said logarithmic amplifier for each of said X-ray spectra.

42. Apparatus according to claim 41, including additional gain control means for modifying the action of said second combining means for said difference images.

43. Apparatus according to claim 41, including linearity control means for utilizing an output signal from said logarithmic amplifier for supplying a correction factor to said gain and level control means to extend the range of patient thickness compensation.

44. Apparatus according to claim 43, in which said correction factor is a decreasing function of the first power of the output of said logarithmic amplifier.

45. A method according to claim 23, including the additional step of converting said X-ray images into video images, logarithmically amplifying said video images, subtractively combining said logarithmically amplified video images, and selectively modifying the logarithmically amplified images to improve the cancellation of image elements due to soft tissue and bone.

46. A method according to claim 45, including the additional step of selectively modifying the combining of said four difference images to improve the cancellation of image elements due to bone.

47. A method according to claim 45, including the additional step of selectively modifying the logarithmic amplification by a correction factor which is a decreasing function of the first power of the logarithmically amplified video images.

48. A method according to claim 1, including the additional step of logarithmically amplifying said first, second and third X-ray images prior to combining said images.

49. Apparatus according to claim 13, including means for logarithmically amplifying said first, second and third X-ray images for presentation to said combining means.

* * * * *

PO-1050
(5/69)

UNITED STATES PATENT OFFICE
CERTIFICATE OF CORRECTION

Patent No. 3,974,386　　　　　　　　Dated August 10, 1976

Inventor(s) Mistretta & Kelcz　　　　　Page 1 of 4

It is certified that error appears in the above-identified patent and that said Letters Patent are hereby corrected as shown below:

Column 9, line 27, "element" should be "elements".

Column 20, line 36, "-5" should be "+5".

Column 21, line 43, "Q" should be "$\bar{Q}$".

Column 23, line 2, "Q" should be "$\bar{Q}$".

Column 23, line 4, "Q" should be "$\bar{Q}$".

Column 29, line 11, "outer" should be "other".

Column 40, following line 6, Equation (1) should appear as follows:

$$2\mu_2^t = \mu_1^t + \mu_3^t \qquad 2\mu_2^B = \mu_1^B + \mu_3^B$$

Column 41, following line 8, Equation (6) should appear as follows:

$$k_2 = \frac{\mu_1^t}{\mu_2^t} \qquad k_3 = \frac{\mu_1^t}{\mu_3^t}$$

Column 41, line 33, insert "where".

Column 41, line 38, delete "where".

Column 43, line 34, "the" should be "this".

UNITED STATES PATENT OFFICE
CERTIFICATE OF CORRECTION

Patent No. 3,974,386   Dated August 10, 1976

Inventor(s) Mistretta & Kelcz

It is certified that error appears in the above-identified patent and that said Letters Patent are hereby corrected as shown below:

Column 45, line 5, in the last term of Equation (17),

"$\sqrt{N/N}$" should be "$\sqrt{N}/N$".

Column 45, line 10, in the last term of Equation (18),

"$\sqrt{4N/N}$" should be "$\sqrt{4N}/N$".

Column 47, in which the entire left hand portion of the column is chopped off, should read as follows:

" ally, when the iodine, cerium and lead filters are operative, respectively.

The channels 922a, b and c are rendered operative in sequence by relays or control switches 926a, b and c, which may be essentially the same as the relays 326a, b and c described in connection with Fig. 17. The relays may be operated in sequence in the manner described in connection with the circuits of Fig. 18. Such circuits are designated sequence control circuits 928 in Fig. 22.

"Provision is made in the individual channels 922a, b and c for adjusting the video signals fed to the log amplifier 924 when the iodine, cerium and lead filters are operative. As shown in Fig. 22, the channels 922a, b and c include direct current level controls 930a, b and c, gain controls 932a, b and c, and amplifiers 934a, b and c. In the usual operation of the X-ray system, the dc level controls 930a, b and c and the gain controls 932a, b and c are generally adjusted so that closely similar video signals are supplied to the log amplifier 924 when the iodine, cerium and lead filters are operative. The log amplifier 924 is in the circuit for all of the filters, so that the logarithmic amplification is always the same.

UNITED STATES PATENT OFFICE
CERTIFICATE OF CORRECTION

Patent No. 3,974,386          Dated  August 10, 1976

Inventor(s) Mistretta & Kelcz          Page 3 of 4

It is certified that error appears in the above-identified patent and that said Letters Patent are hereby corrected as shown below:

"It is possible to provide three individual channels 936a, b and c for transmitting the output signals from the logarithmic amplifier 924 to the input of a video switch 938 which has its output connected to the input of a video difference detector 940. The video switch 938 and the video difference detector 940 may be the same as the video switch 52 and the video difference detector 54, described in connection with Figs. 1 and 17. As before, the video difference detector 940 preferably utilizes a storage tube which may be the same as the storage tube 96 described in connection with Fig. 2.

"The channels 936a, b and c are rendered operative when the iodine, cerium and lead filters are operative. This may be accomplished by utilizing control relays or switches 942a, b and c which may be essentially the same in construction and operation as the relays 326a, b and c, described in connection with Figs. 17 and 18. The relays 942a, b and c may be operated by the sequence control circuits 928, which also operate the relays 926a, b and c and may be essentially the same as the control circuits of Fig. 18.

"Provision is preferably made for adjusting the direct current level and the amplification of the signals supplied from the output of the log amplifier 924 to the video difference detector 940. As shown in Fig. 22, the individual channels 936a, b and c preferably incorporate direct current level controls 944a, b and c, gain controls 946a, b and c, and amplifiers 948a, b and c. In the usual operation of the X-ray system, the dc level controls 944a, b and c and the gain controls 946a, b and c will be adjusted to provide the requisite values of $k_2$ and $k_3$, as described above in connection with equations (5) and (6). This adjustment can easily be accom-

PO-1050
(5/69)

UNITED STATES PATENT OFFICE
CERTIFICATE OF CORRECTION

Patent No. 3,974,386      Dated August 10, 1976

Inventor(s) Mistretta & Kelcz      Page 4 of 4

It is certified that error appears in the above-identified patent and that said Letters Patent are hereby corrected as shown below:

plished by positioning a continuous wedge in the X-ray field, to simulate a range of patient thicknesses. The slope of the wedge provides a continuously increasing absorber thickness along with the x or y axis of the television scan. The exponentially decreasing transmitted intensity of the X-rays for each filter produces a straight line at the input of the video difference detector 940 due to the action of the logarithmic amplifier 924. Such straight line can be displayed on an oscilloscope connected to the input of the video difference detector 940. A representative oscilloscope trace is".

Column 54, line 50, "included" should be "includes".

Signed and Sealed this

Twenty-eighth Day of December 1976

[SEAL]

Attest:

RUTH C. MASON
*Attesting Officer*

C. MARSHALL DANN
*Commissioner of Patents and Trademarks*